United States Patent
Takahashi et al.

(10) Patent No.: US 10,966,590 B2
(45) Date of Patent: Apr. 6, 2021

(54) SURGICAL SYSTEM, INFORMATION PROCESSING DEVICE, AND METHOD

(71) Applicant: SONY CORPORATION, Tokyo (JP)

(72) Inventors: Yasuaki Takahashi, Kanagawa (JP); Tomoyuki Hirayama, Kanagawa (JP); Hiroshi Ichiki, Kanagawa (JP); Masahito Yamane, Kanagawa (JP); Yuki Sugie, Kanagawa (JP); Hisakazu Shiraki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 579 days.

(21) Appl. No.: 15/535,206

(22) PCT Filed: Mar. 15, 2016

(86) PCT No.: PCT/JP2016/001454
§ 371 (c)(1),
(2) Date: Jun. 12, 2017

(87) PCT Pub. No.: WO2016/152087
PCT Pub. Date: Sep. 29, 2016

(65) Prior Publication Data
US 2017/0367559 A1    Dec. 28, 2017

(30) Foreign Application Priority Data
Mar. 26, 2015 (JP) .............. JP2015-063824

(51) Int. Cl.
A61B 1/00 (2006.01)
A61B 5/00 (2006.01)
(Continued)

(52) U.S. Cl.
CPC ...... *A61B 1/00009* (2013.01); *A61B 1/00055* (2013.01); *A61B 5/01* (2013.01);
(Continued)

(58) Field of Classification Search
CPC .... A61B 1/00009; A61B 1/043; A61B 1/0125
See application file for complete search history.

(56) References Cited

U.S. PATENT DOCUMENTS 5,647,368 A * 7/1997 Zeng .................. A61B 1/00009
                                                    600/476
5,769,792 A * 6/1998 Palcic .................. A61B 5/0071
                                                    356/318
(Continued)

FOREIGN PATENT DOCUMENTS

EP      2 057 934 A1    5/2009
JP      7-500757 A      1/1995
(Continued)

OTHER PUBLICATIONS

Combined Chinese Office Action and Search Report dated Dec. 19, 2018 in Patent Application No. 201680016388.1 (with English translation).

(Continued)

*Primary Examiner* — Aaron B Fairchild
(74) *Attorney, Agent, or Firm* — Xsensus, LLP

(57) ABSTRACT

There is provided a surgical system including a monitoring sensor configured to sense a characteristic of a surgical site within a body, in a sensing region of the surgical site which includes at least a part of a region outside a display field of an endoscope, and circuitry configured to detect an occurrence of a medical abnormality in the region outside the display field of the endoscope based on a result of the sensing by the monitoring sensor, and generate notification information regarding the detected medical abnormality.

27 Claims, 30 Drawing Sheets

(51) Int. Cl.
*A61B 5/01* (2006.01)
*A61B 1/313* (2006.01)
*A61B 1/05* (2006.01)
*A61B 1/06* (2006.01)

(52) U.S. Cl.
CPC .......... *A61B 5/743* (2013.01); *A61B 1/00016* (2013.01); *A61B 1/00018* (2013.01); *A61B 1/05* (2013.01); *A61B 1/0661* (2013.01); *A61B 1/313* (2013.01); *A61B 5/0036* (2018.08); *A61B 5/4836* (2013.01)

(56) References Cited

U.S. PATENT DOCUMENTS

| | | | |
|---|---|---|---|
| 6,148,227 A * | 11/2000 | Wagnieres | A61B 1/043 348/77 |
| 2002/0026099 A1* | 2/2002 | Adachi | A61B 1/00009 600/178 |
| 2002/0093563 A1* | 7/2002 | Cline | A61B 1/045 348/65 |
| 2002/0161282 A1* | 10/2002 | Fulghum | A61B 1/00009 600/160 |
| 2011/0301414 A1 | 12/2011 | Hotto et al. | |
| 2013/0289348 A1 | 10/2013 | Hotto et al. | |
| 2014/0135595 A1 | 5/2014 | Powell et al. | |
| 2014/0206951 A1 | 7/2014 | Deppmeier et al. | |
| 2015/0032008 A1 | 1/2015 | Landesman | |
| 2015/0073217 A1 | 3/2015 | Powell et al. | |

FOREIGN PATENT DOCUMENTS

| | | |
|---|---|---|
| JP | 9-149876 A | 6/1997 |
| JP | 10-328136 A | 12/1998 |
| JP | 2001-104246 A | 4/2001 |
| JP | 2006-187385 A | 7/2006 |
| JP | 2006-187385 A5 | 7/2006 |
| JP | 2007-151594 A | 6/2007 |
| JP | 2007-151594 A5 | 6/2007 |
| JP | 2008-132321 A | 6/2008 |
| JP | 2011-10841 A | 1/2011 |
| JP | 5499426 B2 | 5/2014 |
| JP | 2015-24330 A | 2/2015 |
| WO | WO 2011/142189 A1 | 11/2011 |
| WO | WO 2016/072237 A1 | 5/2016 |

OTHER PUBLICATIONS

International Search Report dated Jun. 13, 2016 in PCT/JP2016/001454 filed Mar. 15, 2016.
Office Action dated Feb. 8, 2018 in Japanese Patent Application No. 2015-063824 (with English language translation), 23 pages.
Office Action dated Jul. 31, 2018 in corresponding Japanese Patent Application No. 2015-063824 (with English Translation), 10 pages.

* cited by examiner

[Fig. 1]
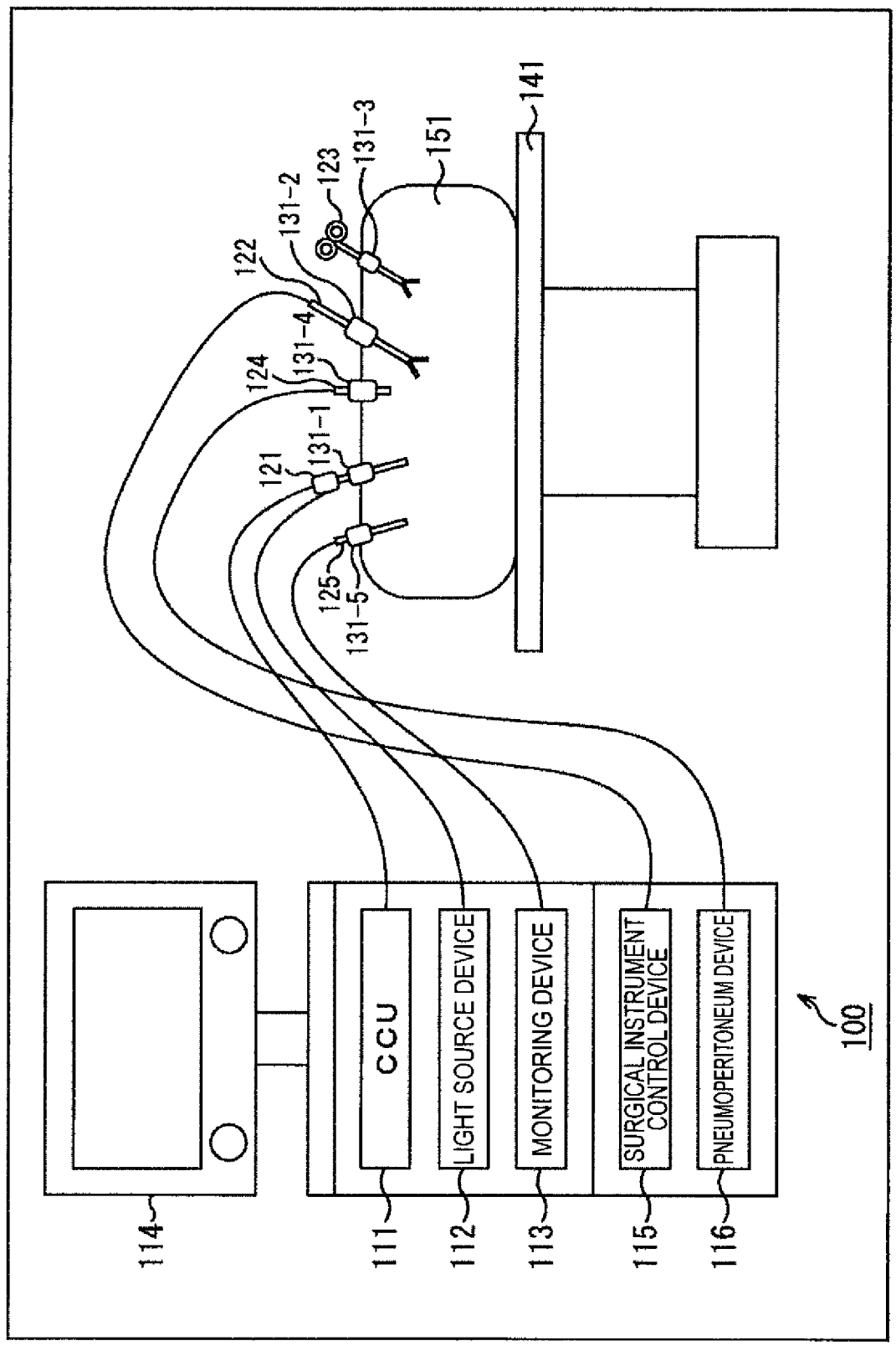

[Fig. 2]
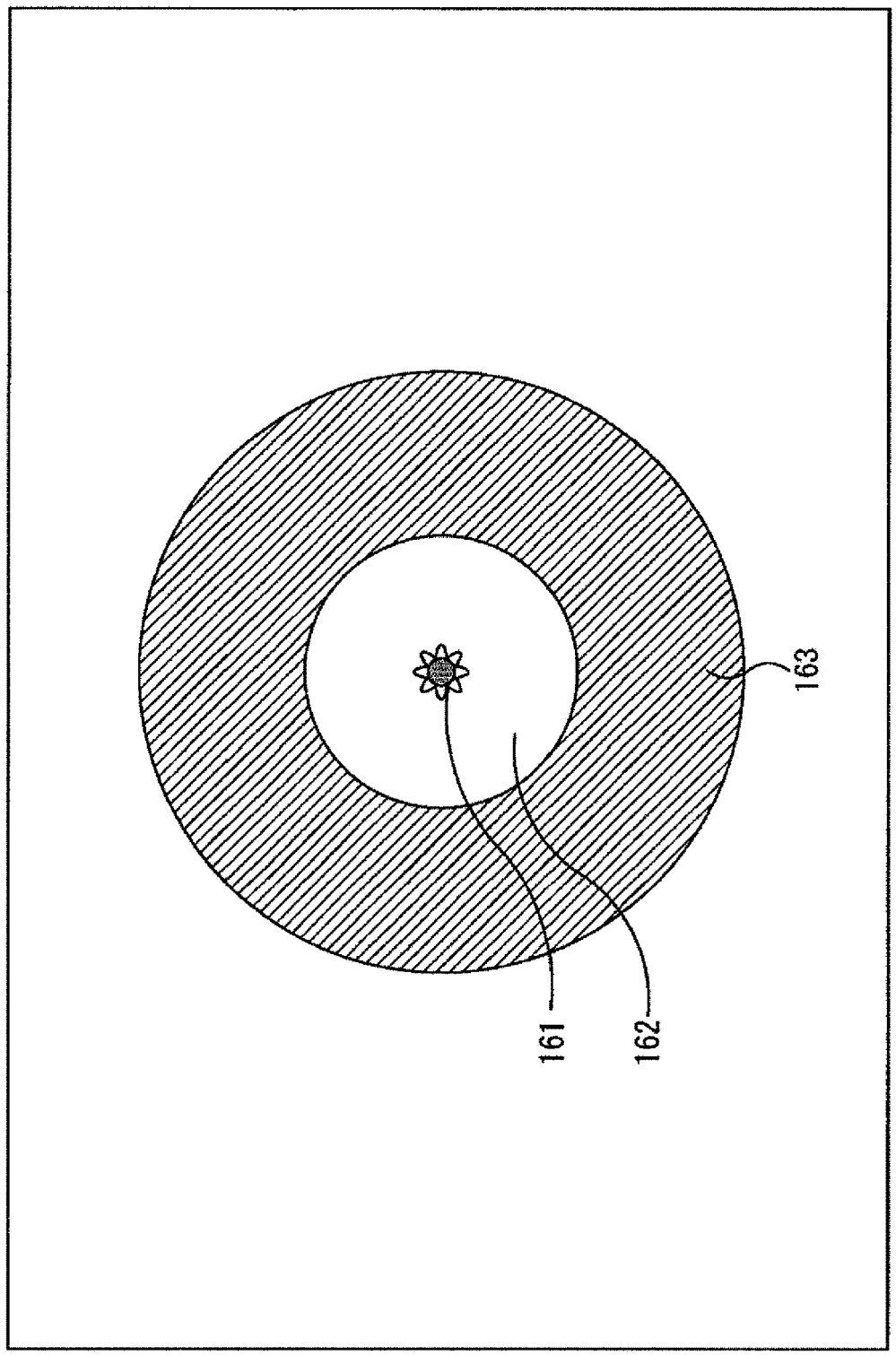

[Fig. 3]
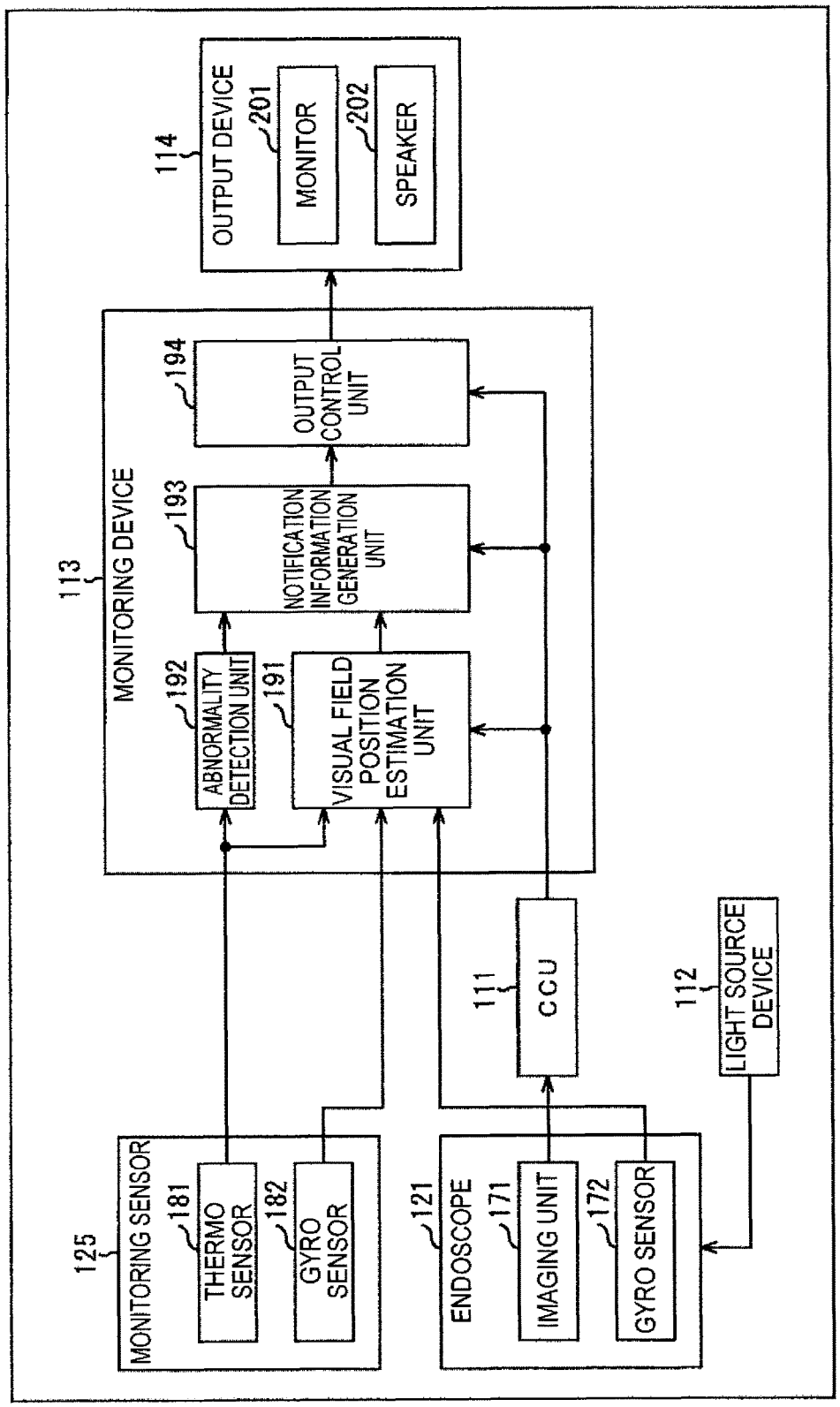

[Fig. 4]
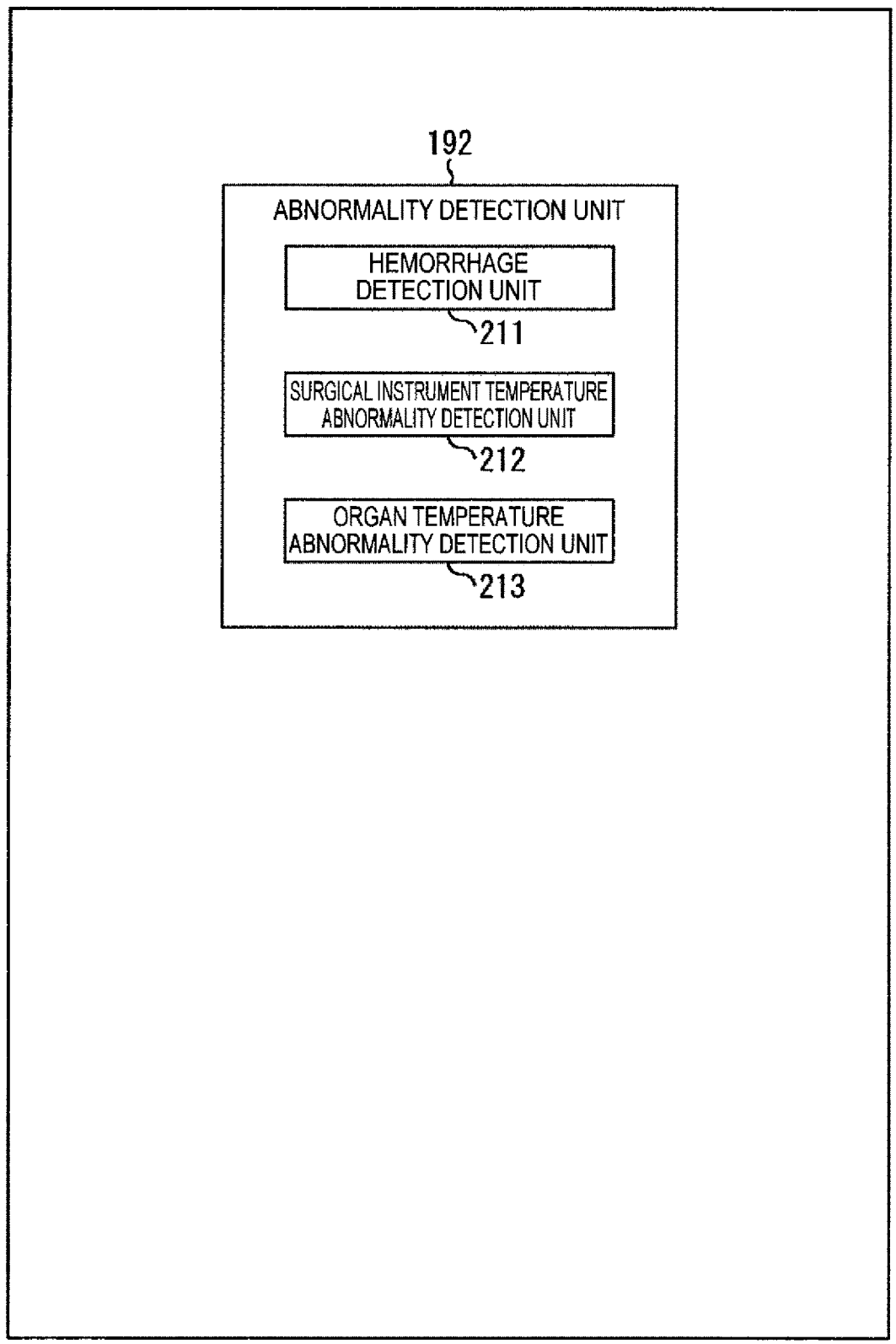

[Fig. 5]
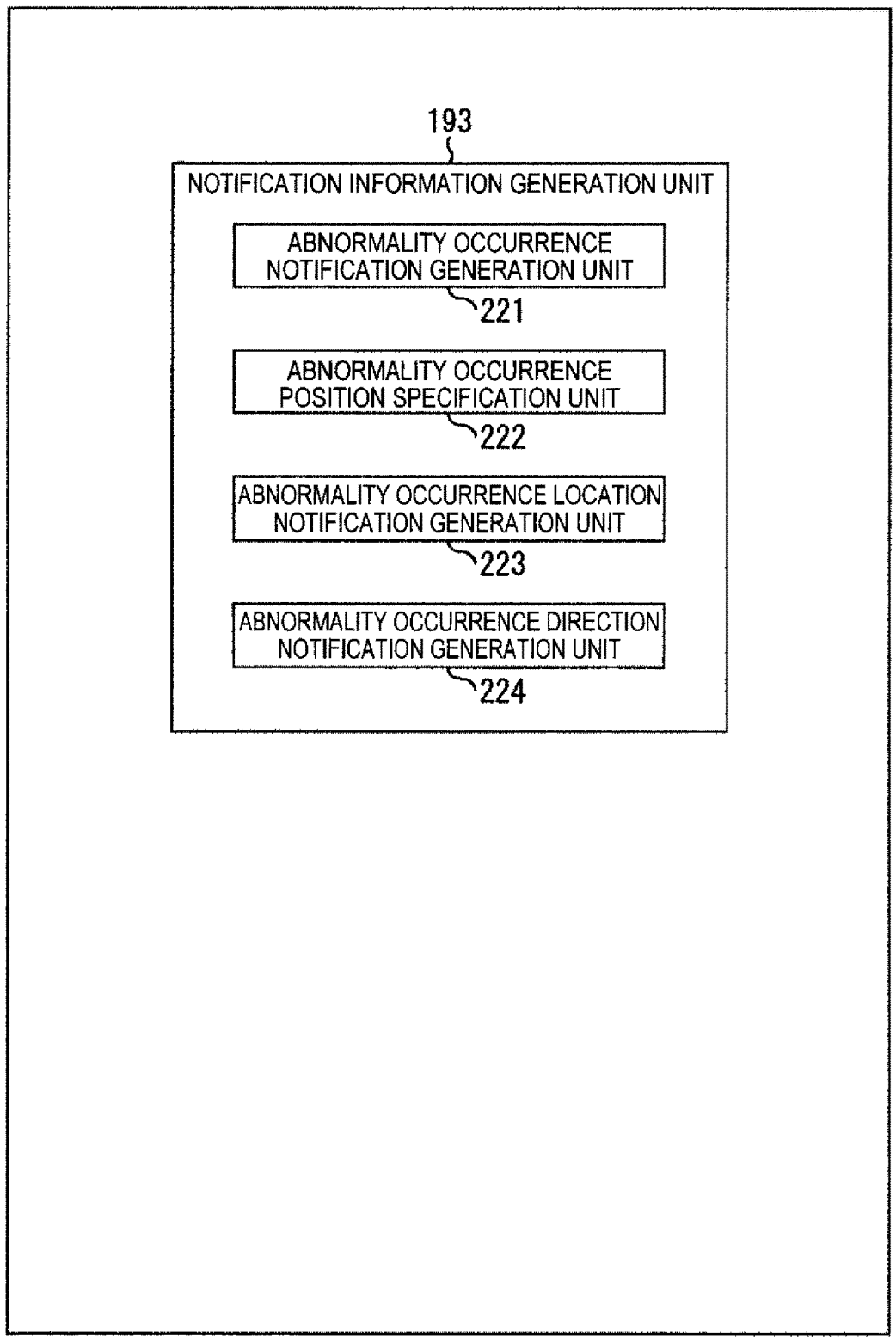

[Fig. 6]
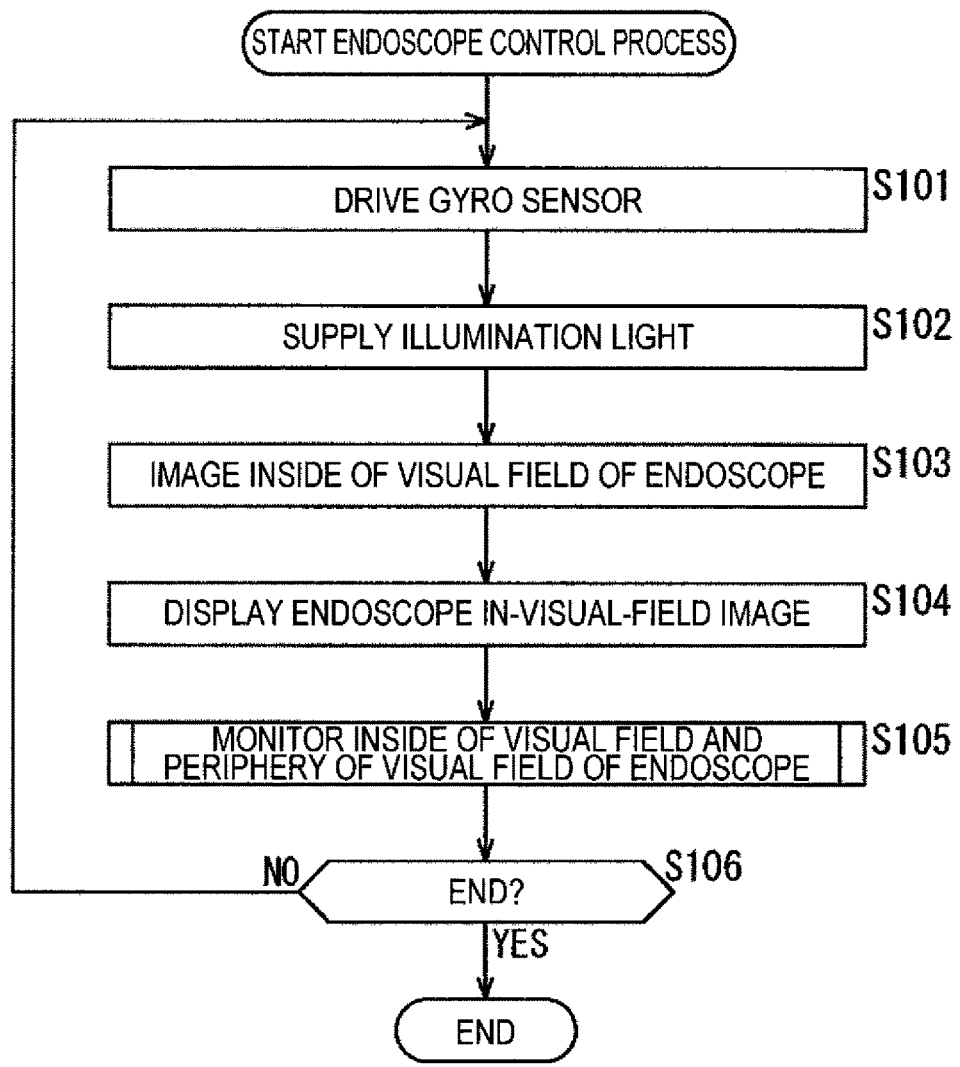

[Fig. 7]
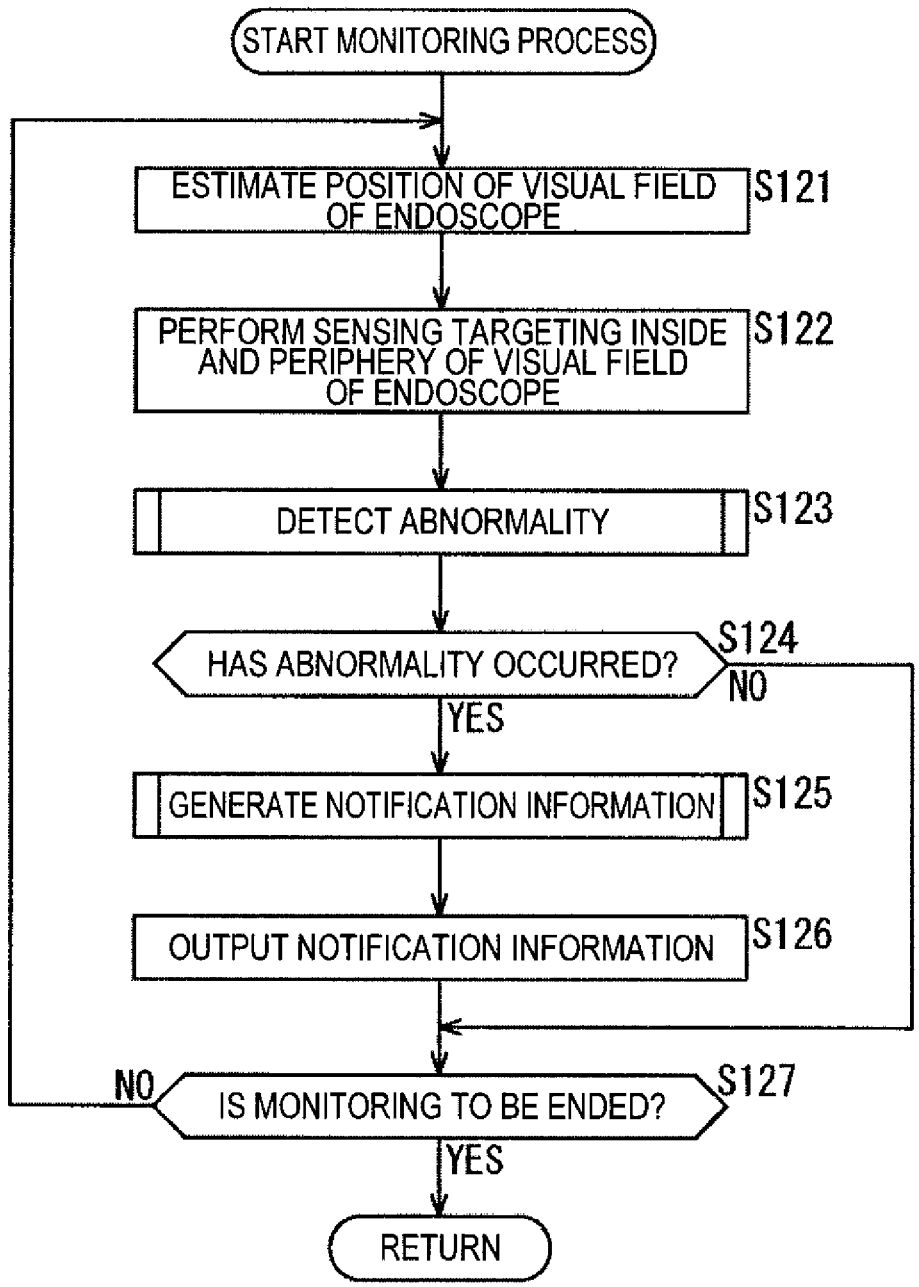

[Fig. 8]
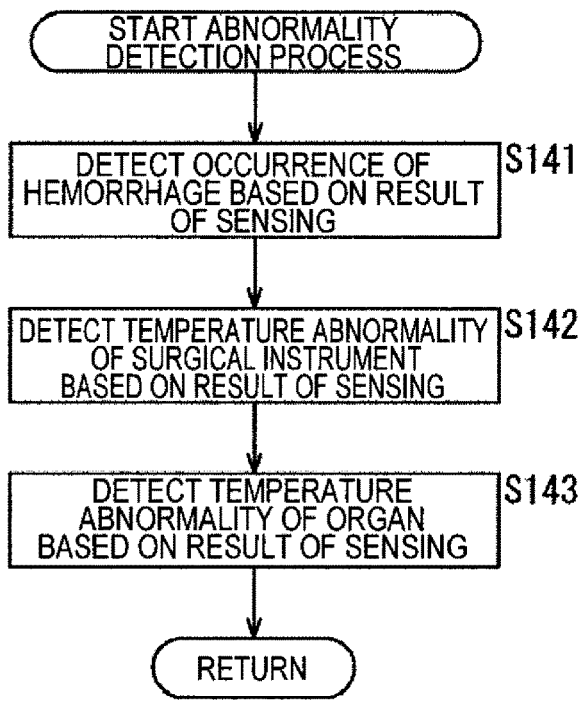
[Fig. 9]
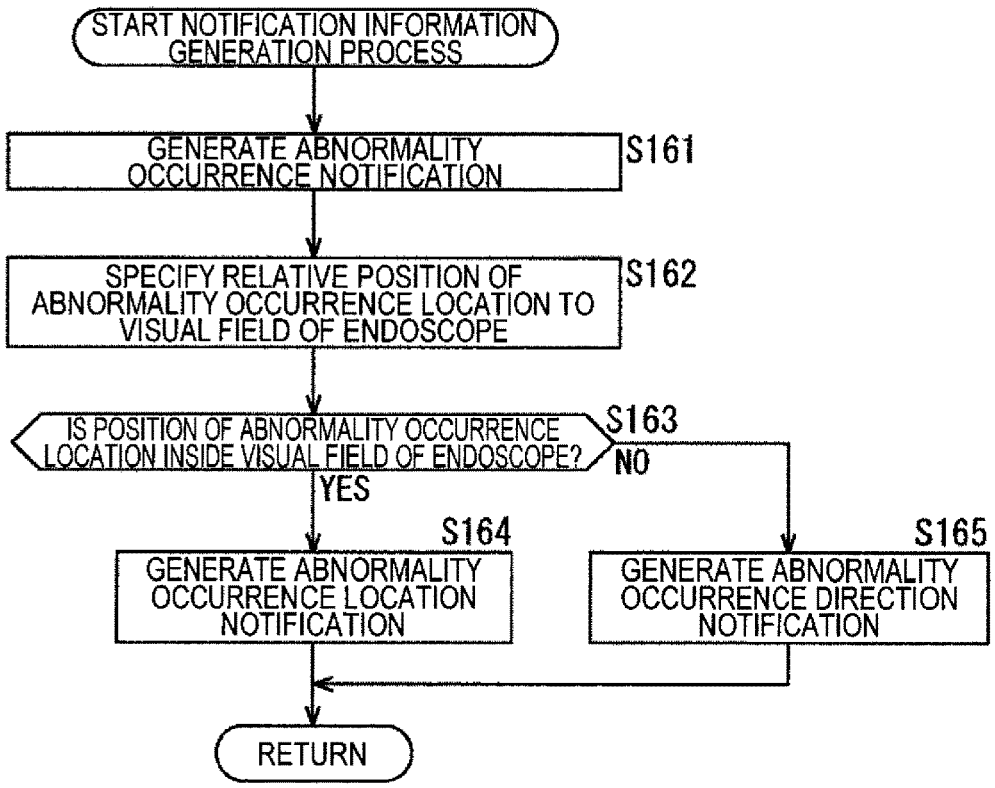

[Fig. 10]
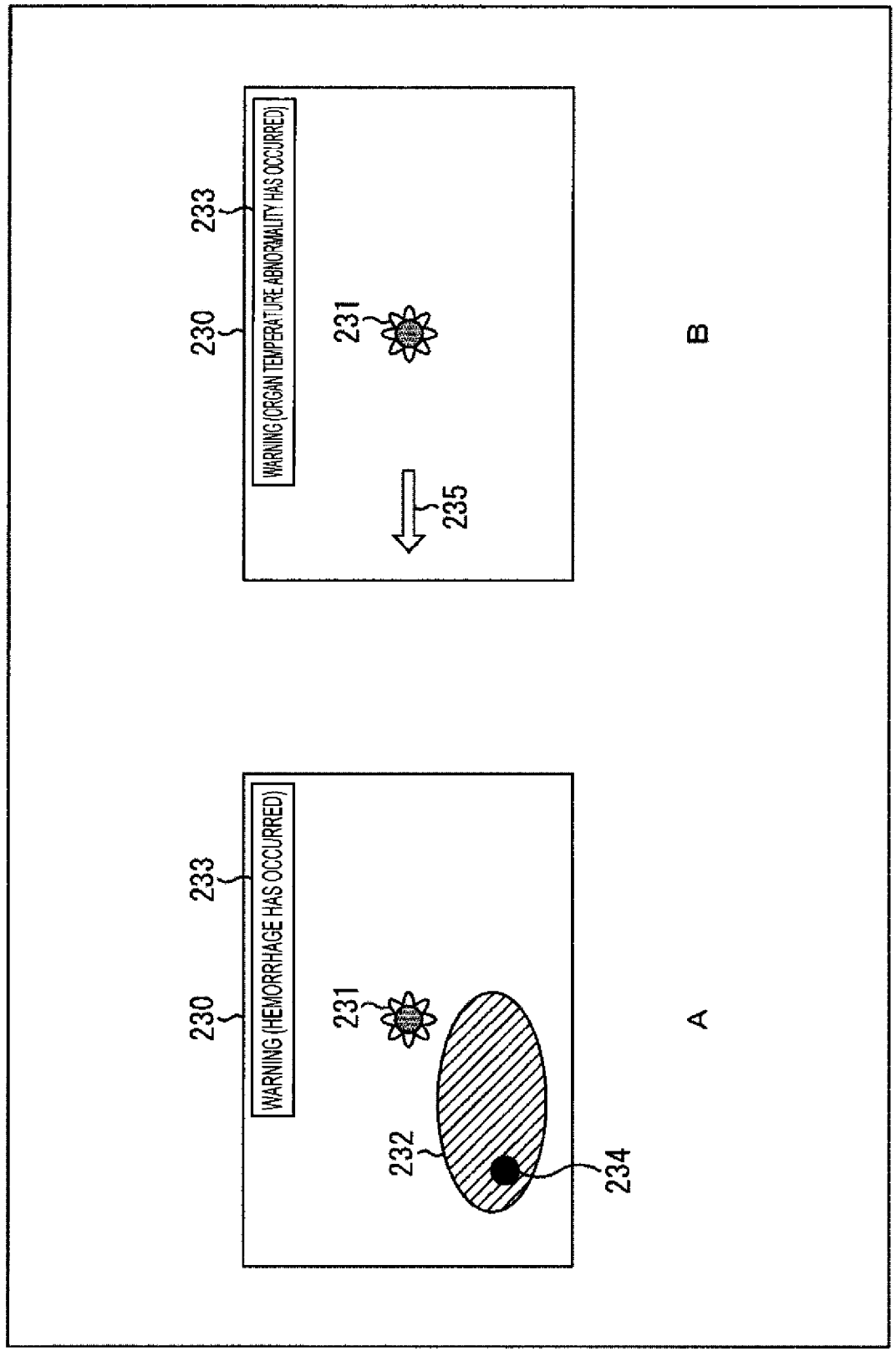

[Fig. 11]
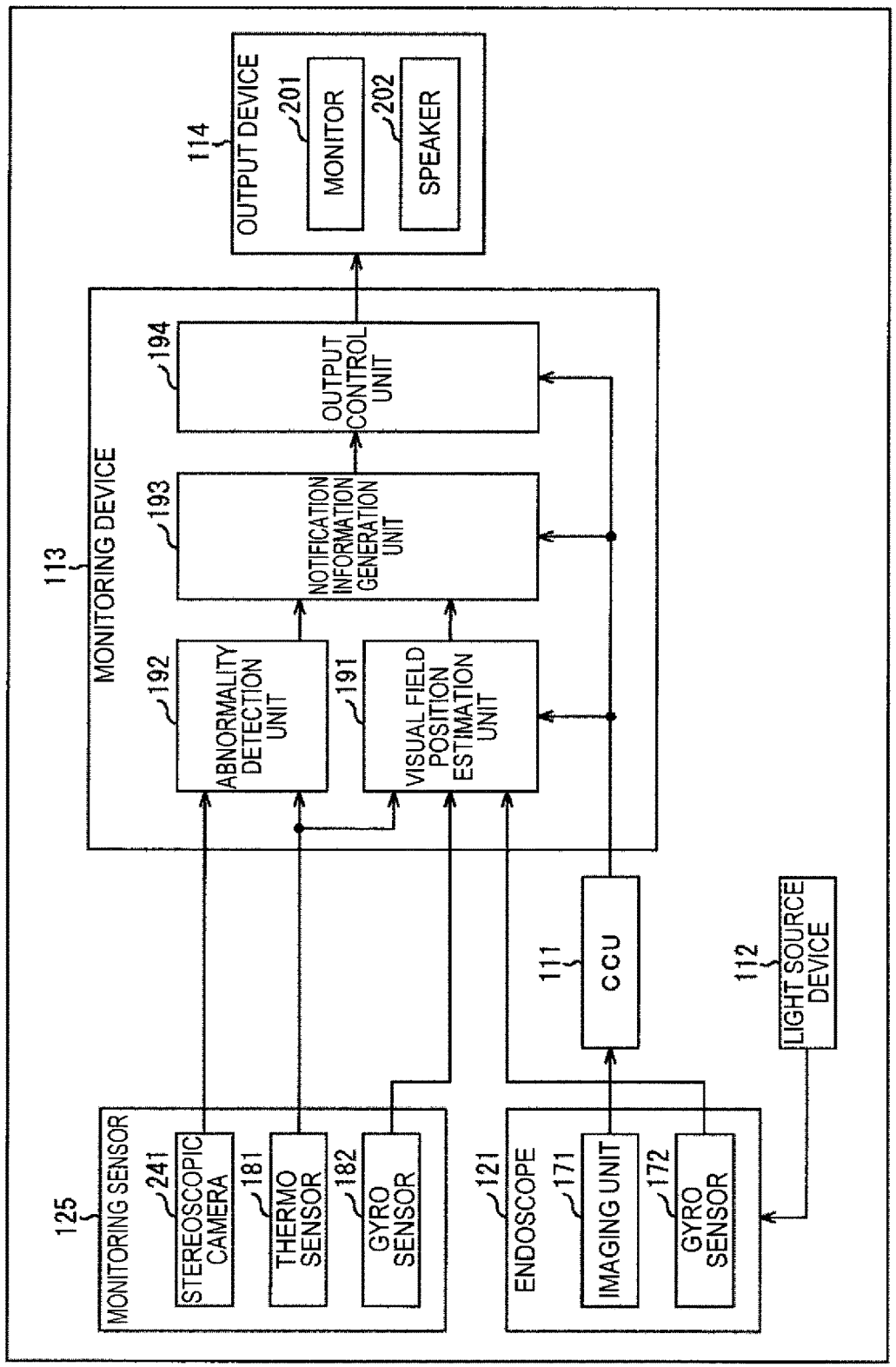

[Fig. 12]
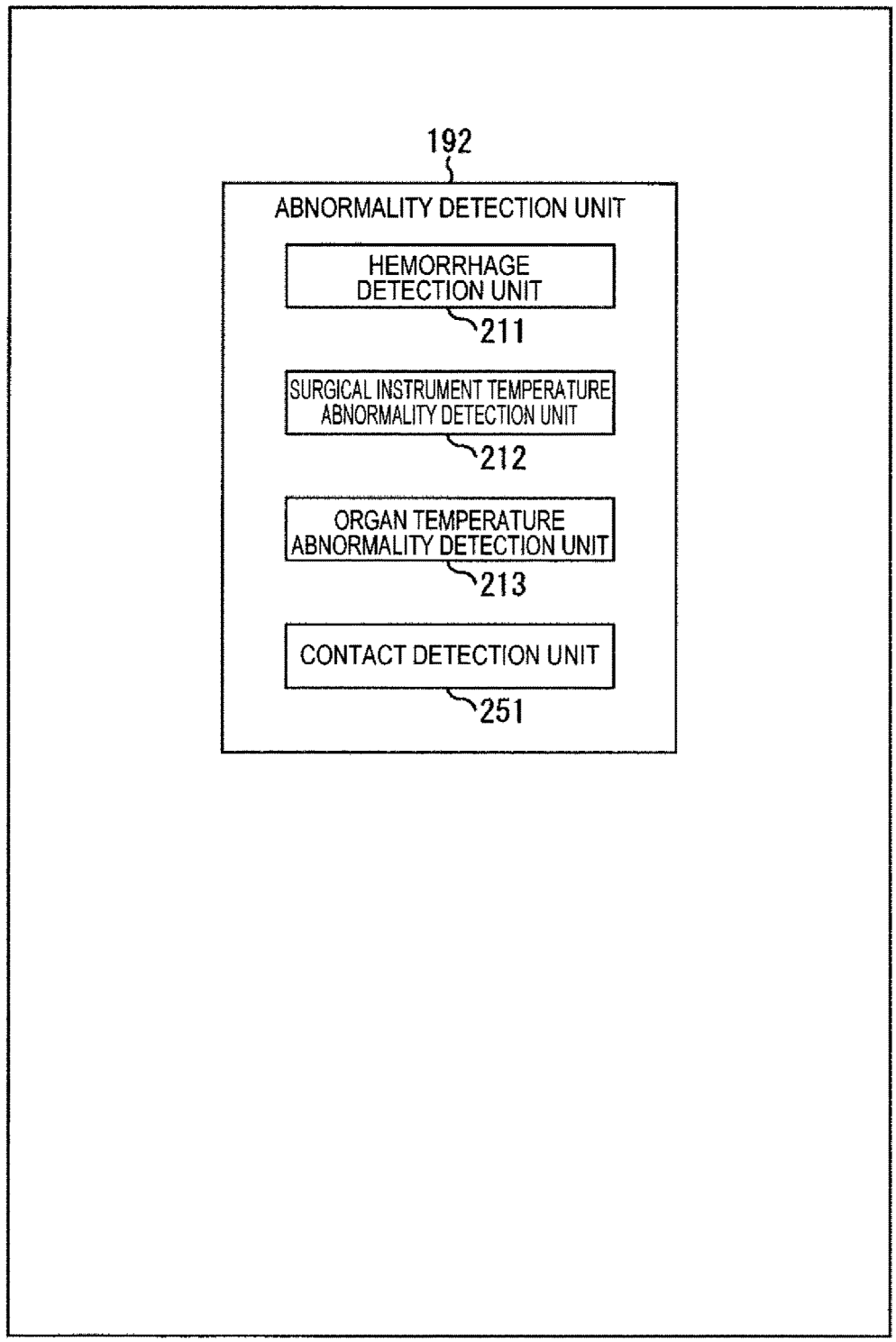

[Fig. 13]
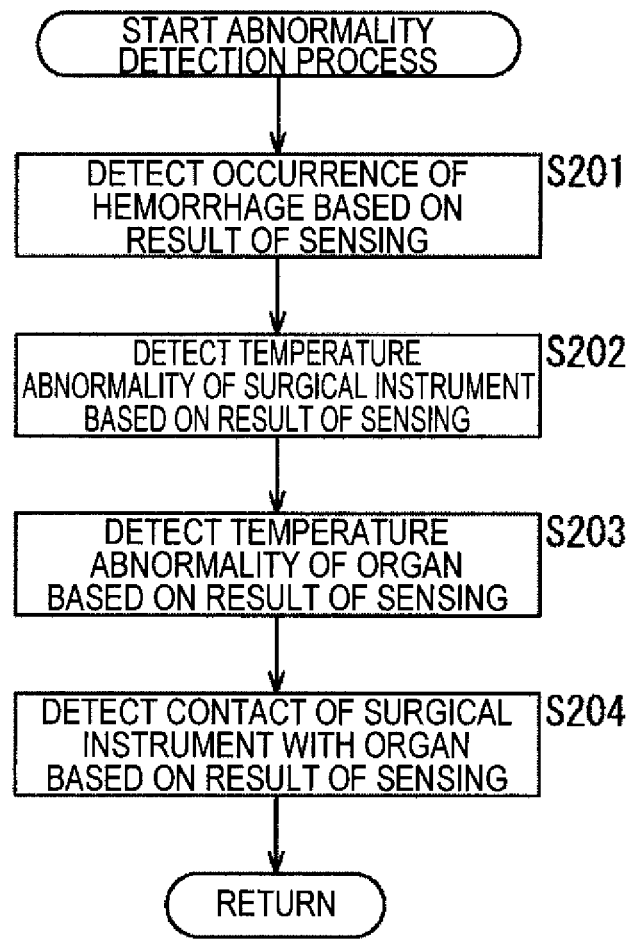

[Fig. 14]
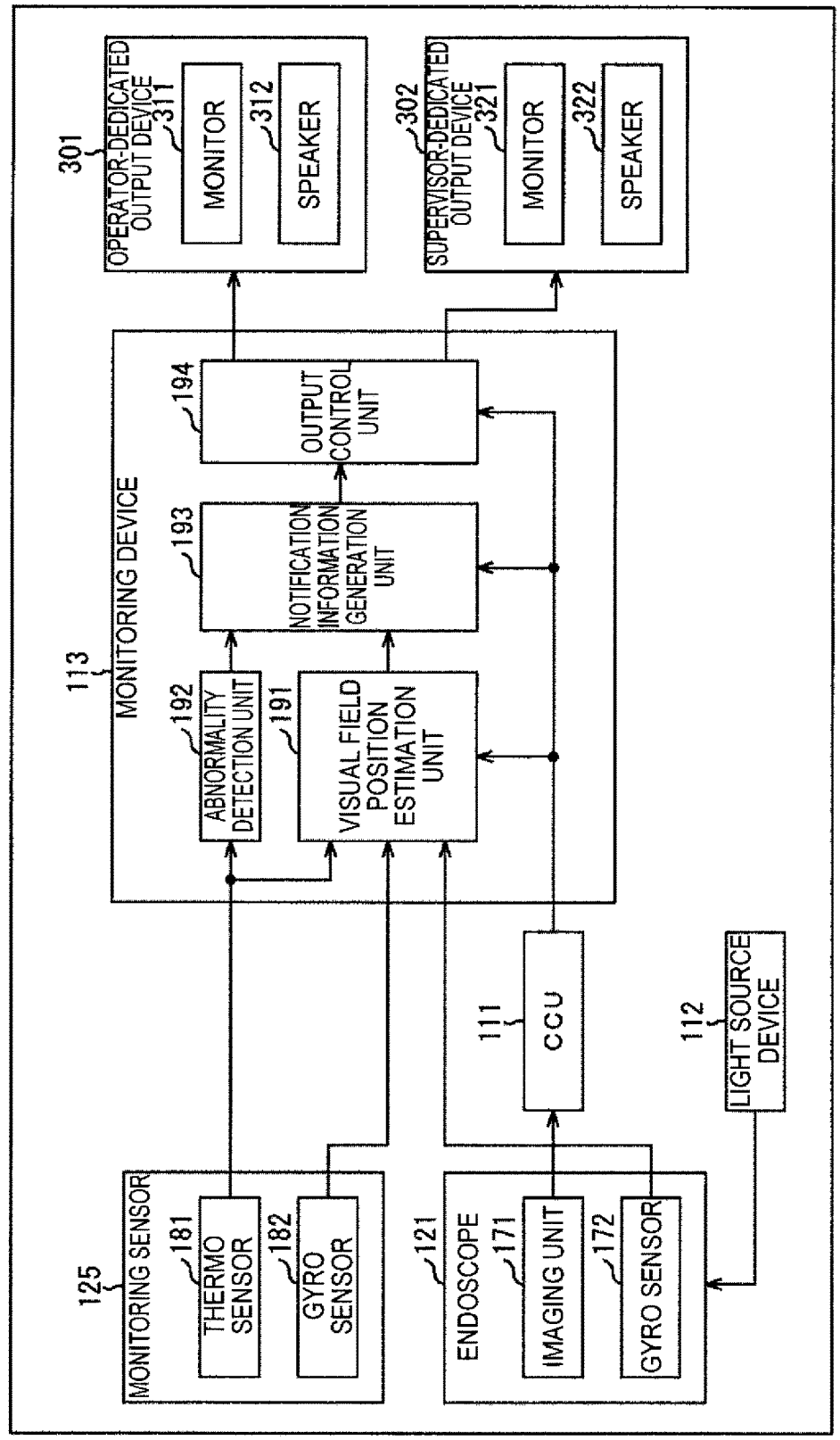

[Fig. 15]
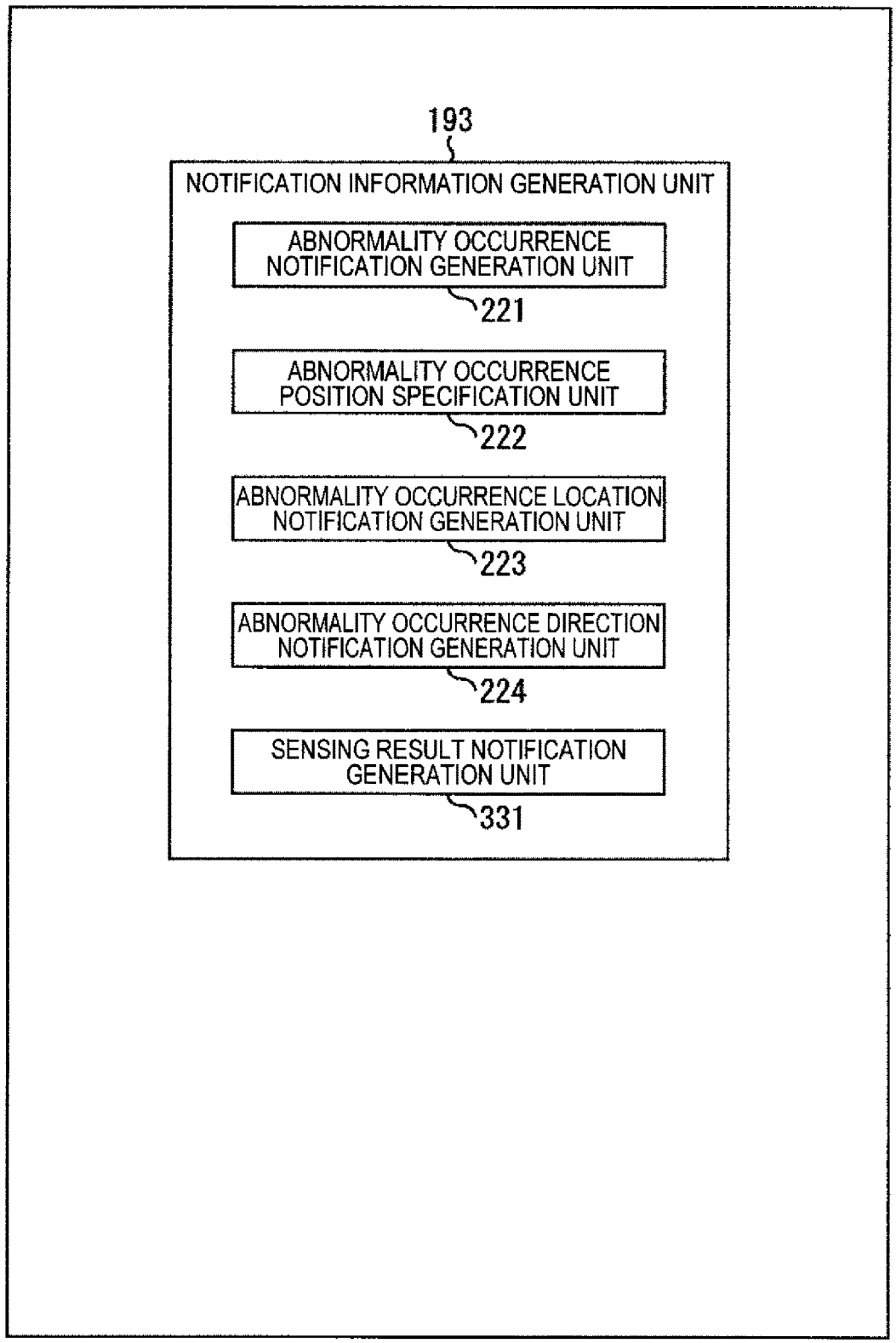

[Fig. 16]
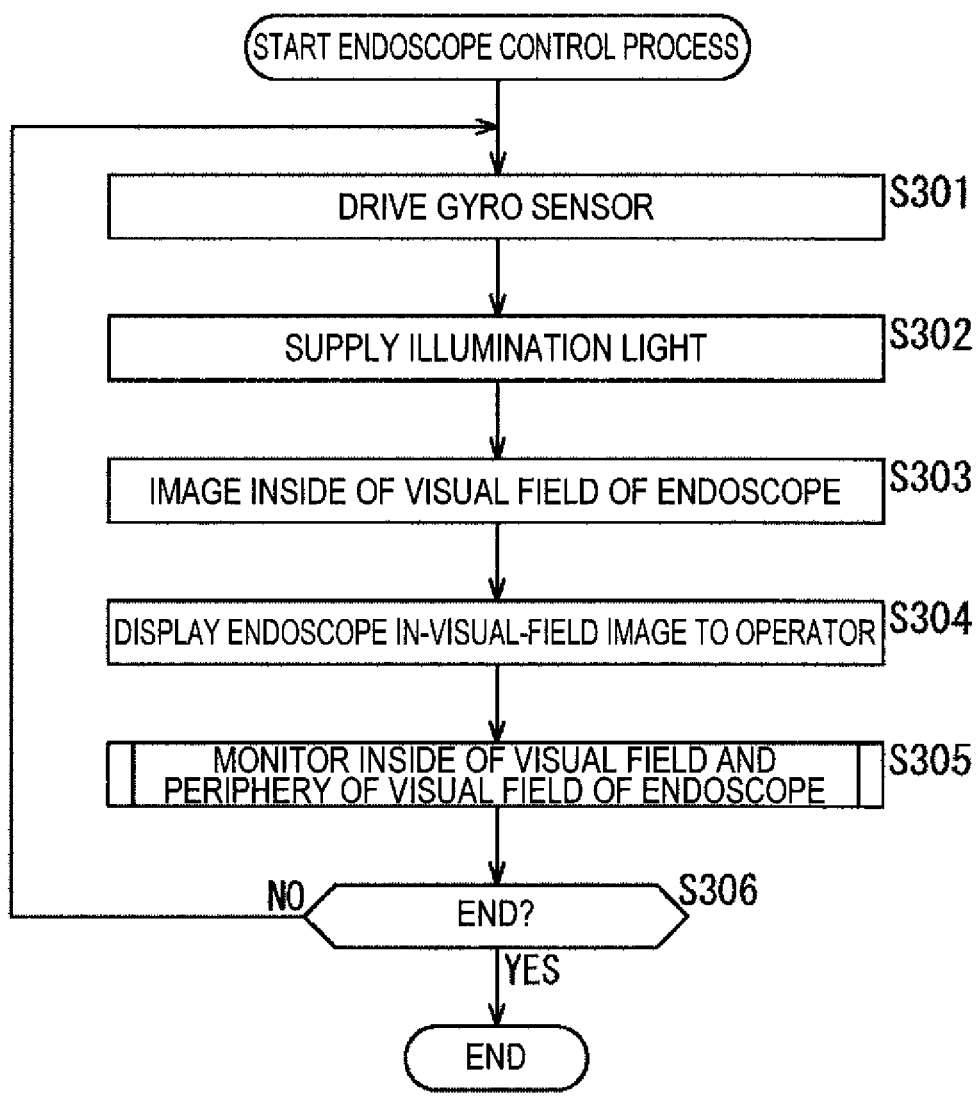

[Fig. 17]
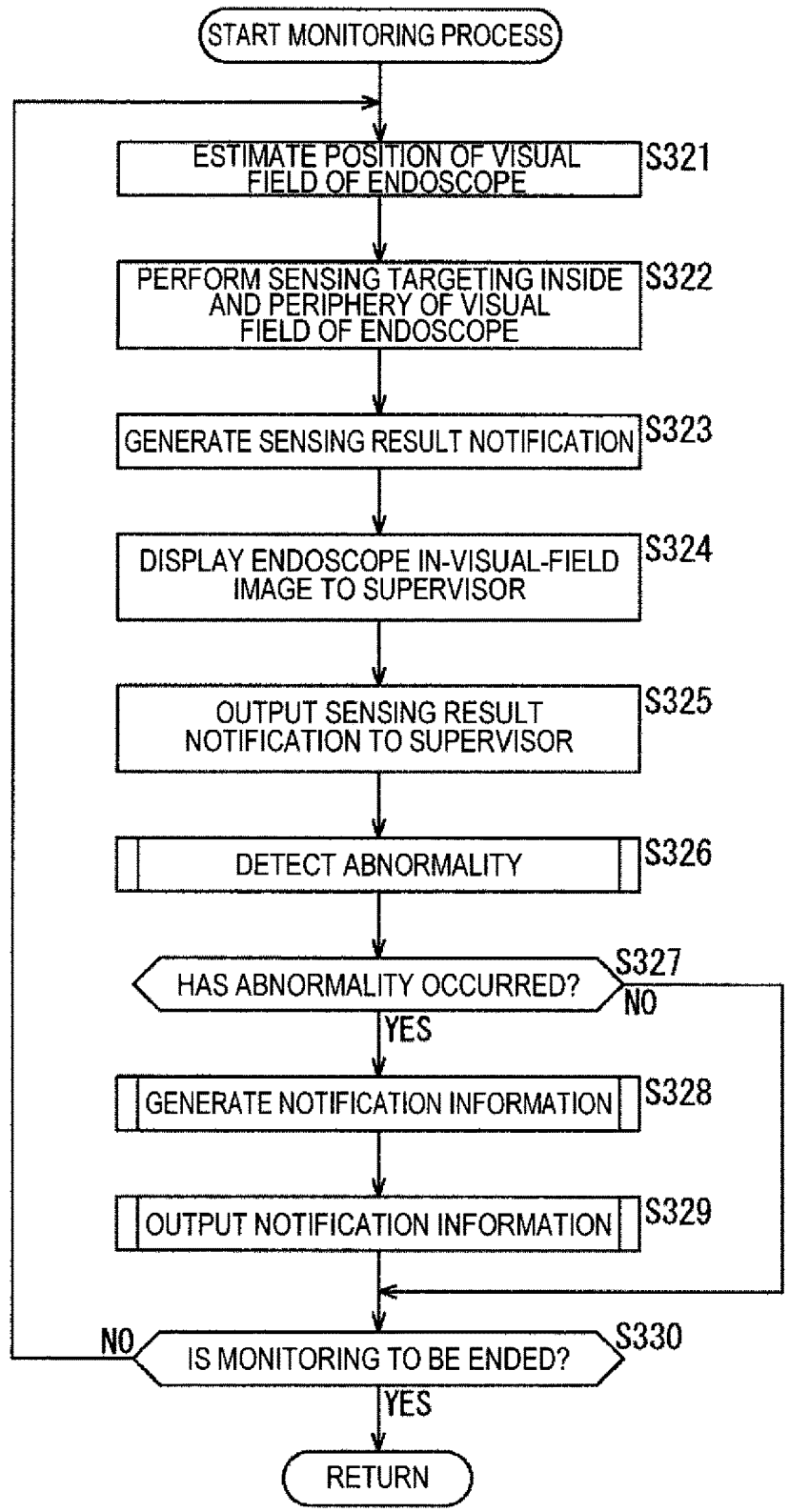

[Fig. 18]
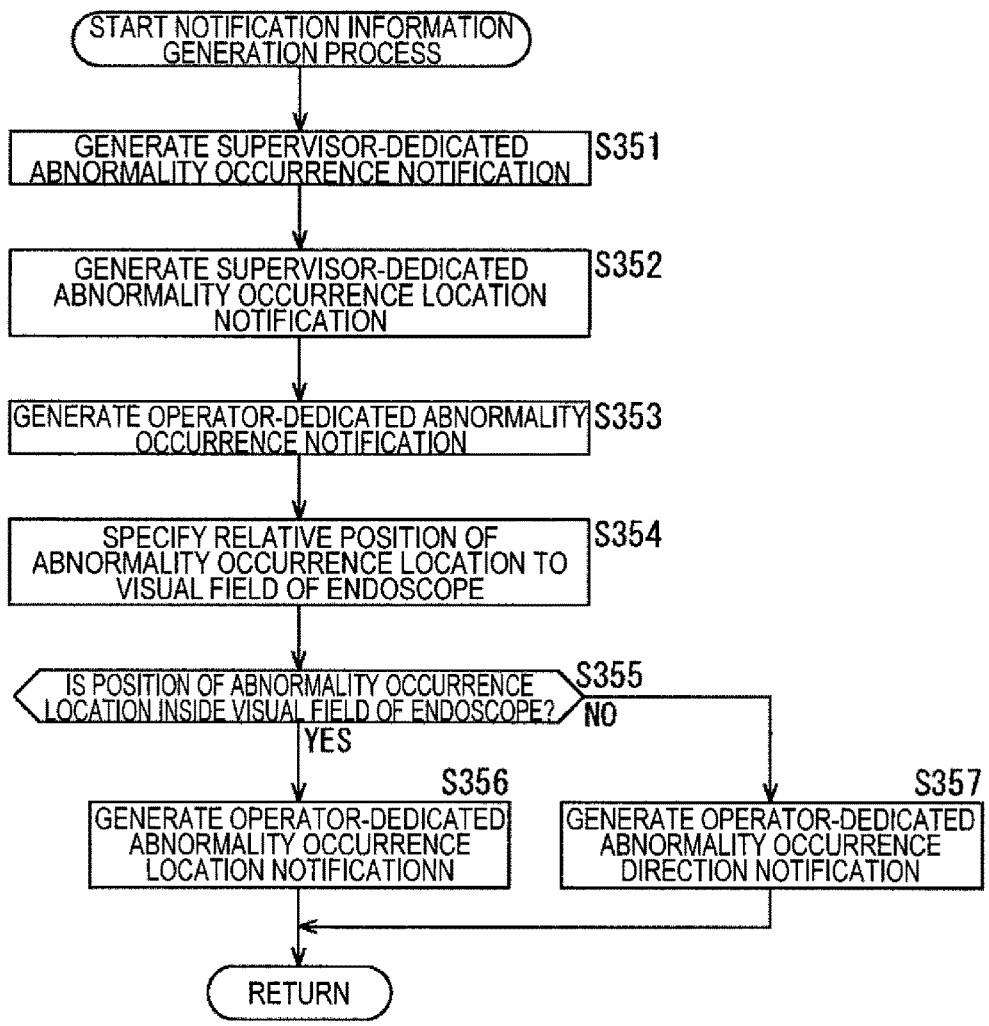

[Fig. 19]
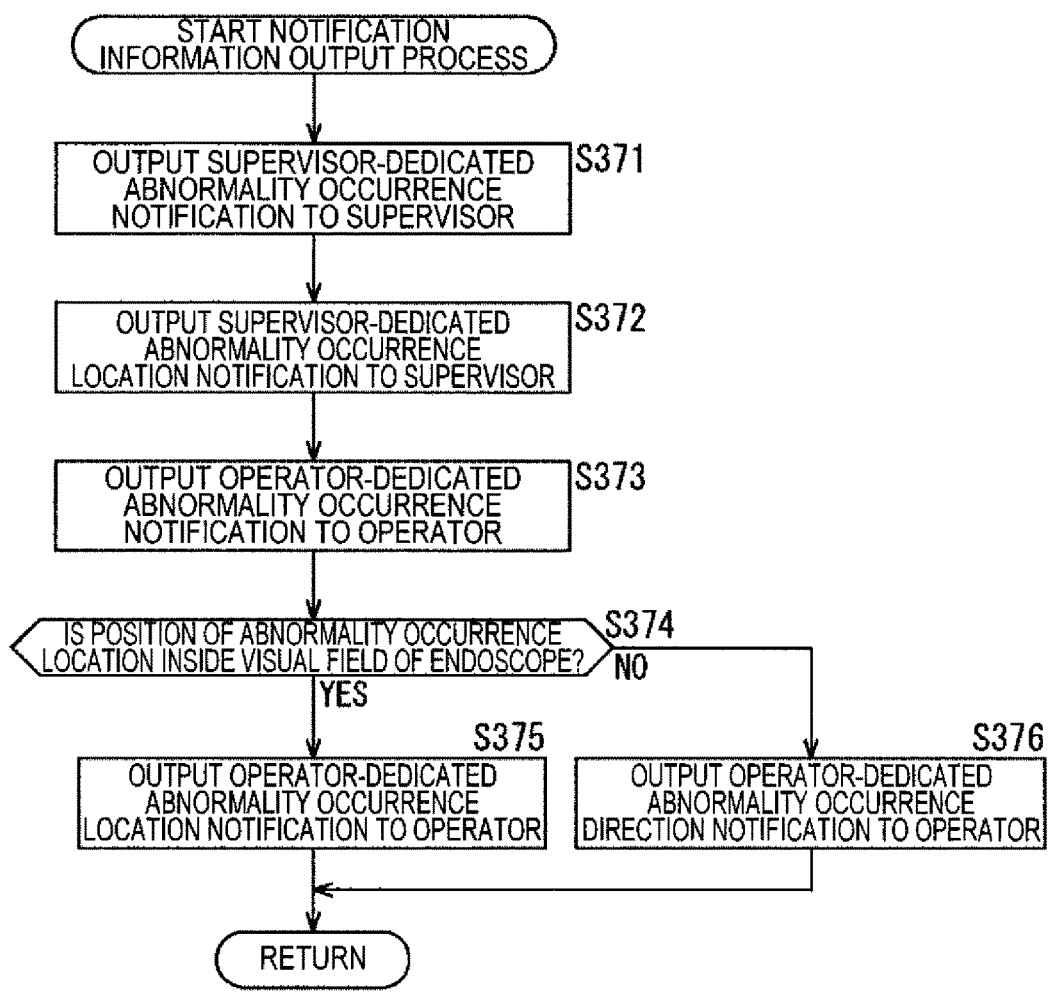

[Fig. 20]
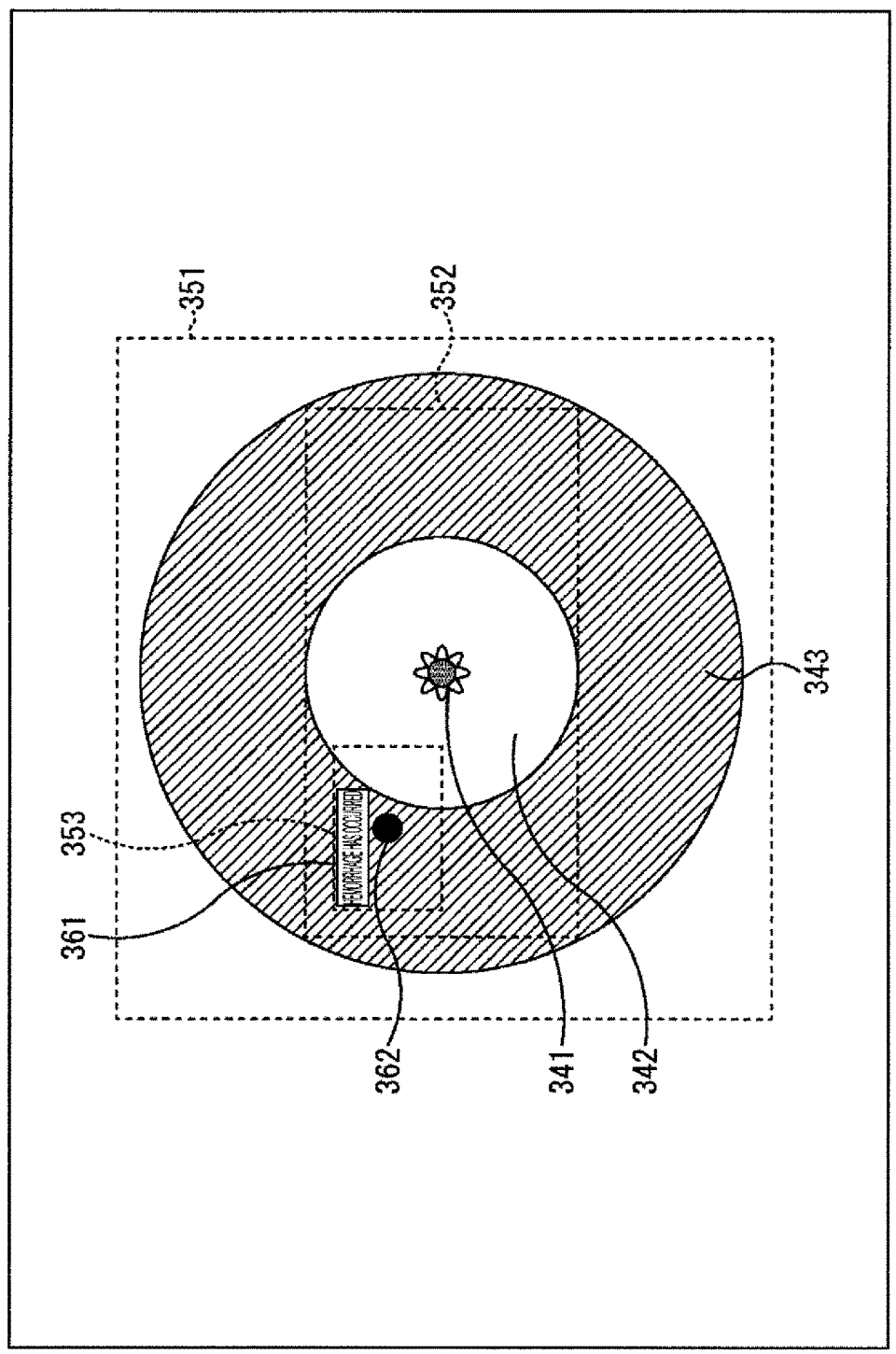

[Fig. 21]
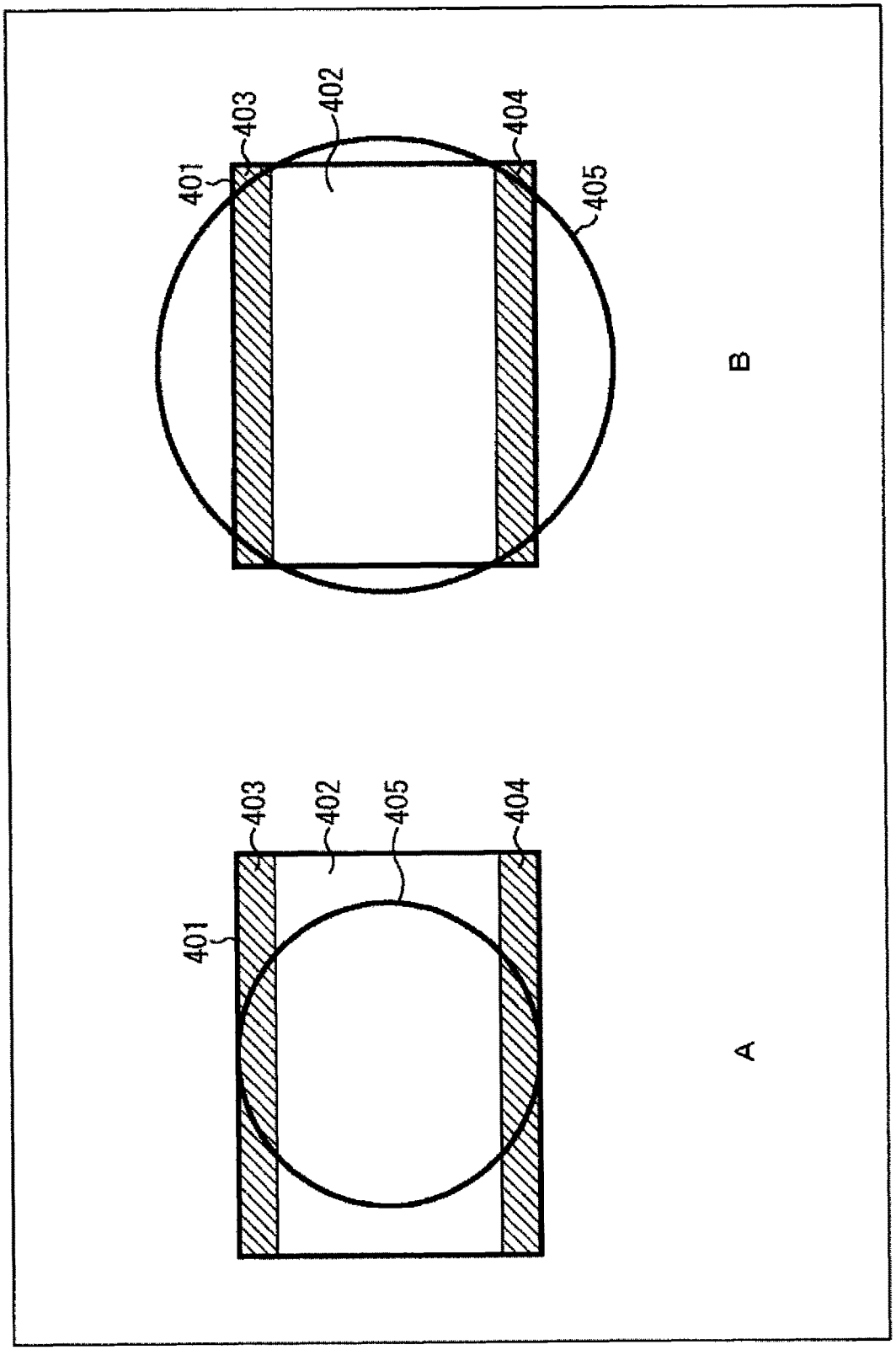

[Fig. 22]
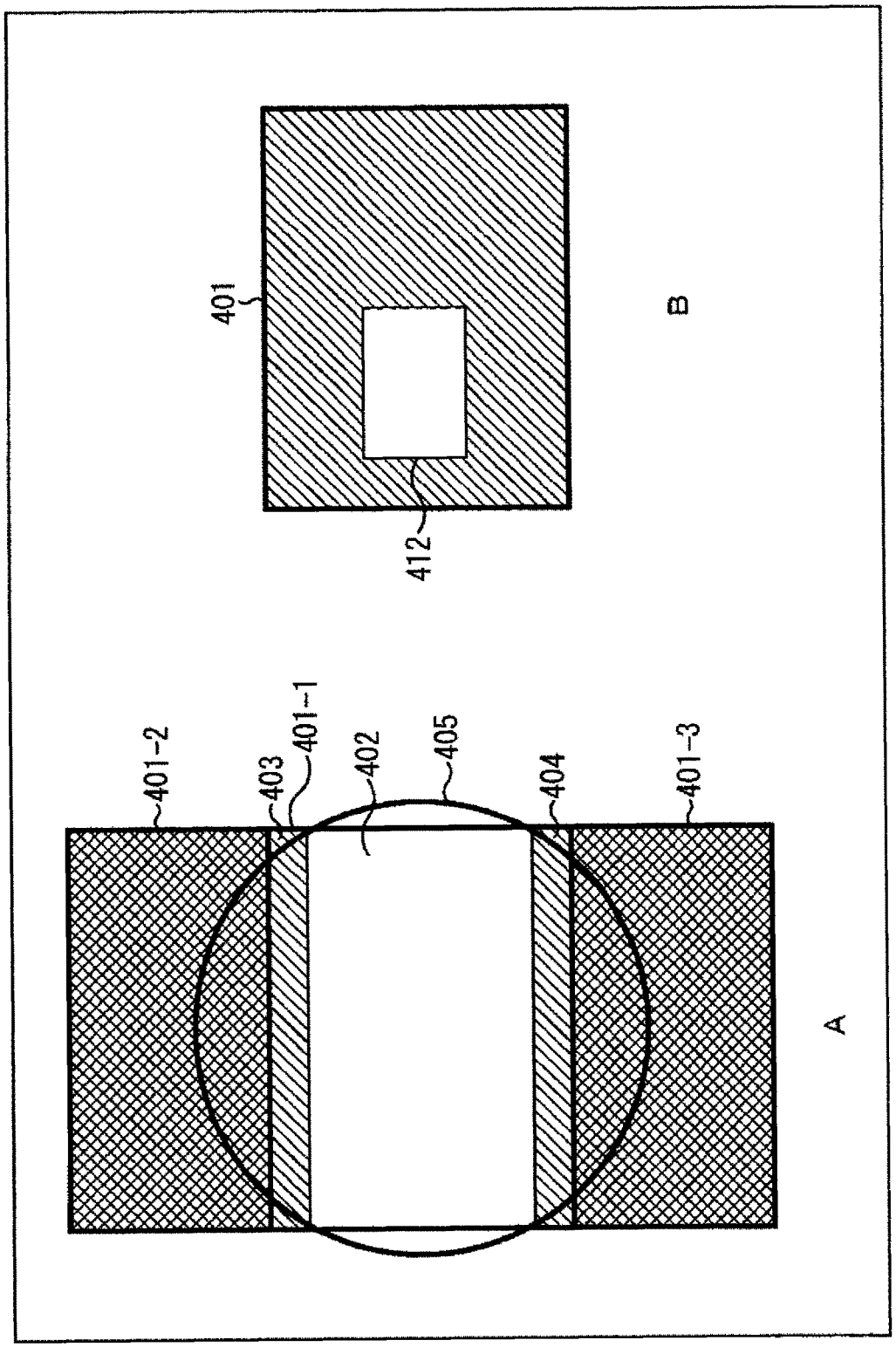

[Fig. 23]
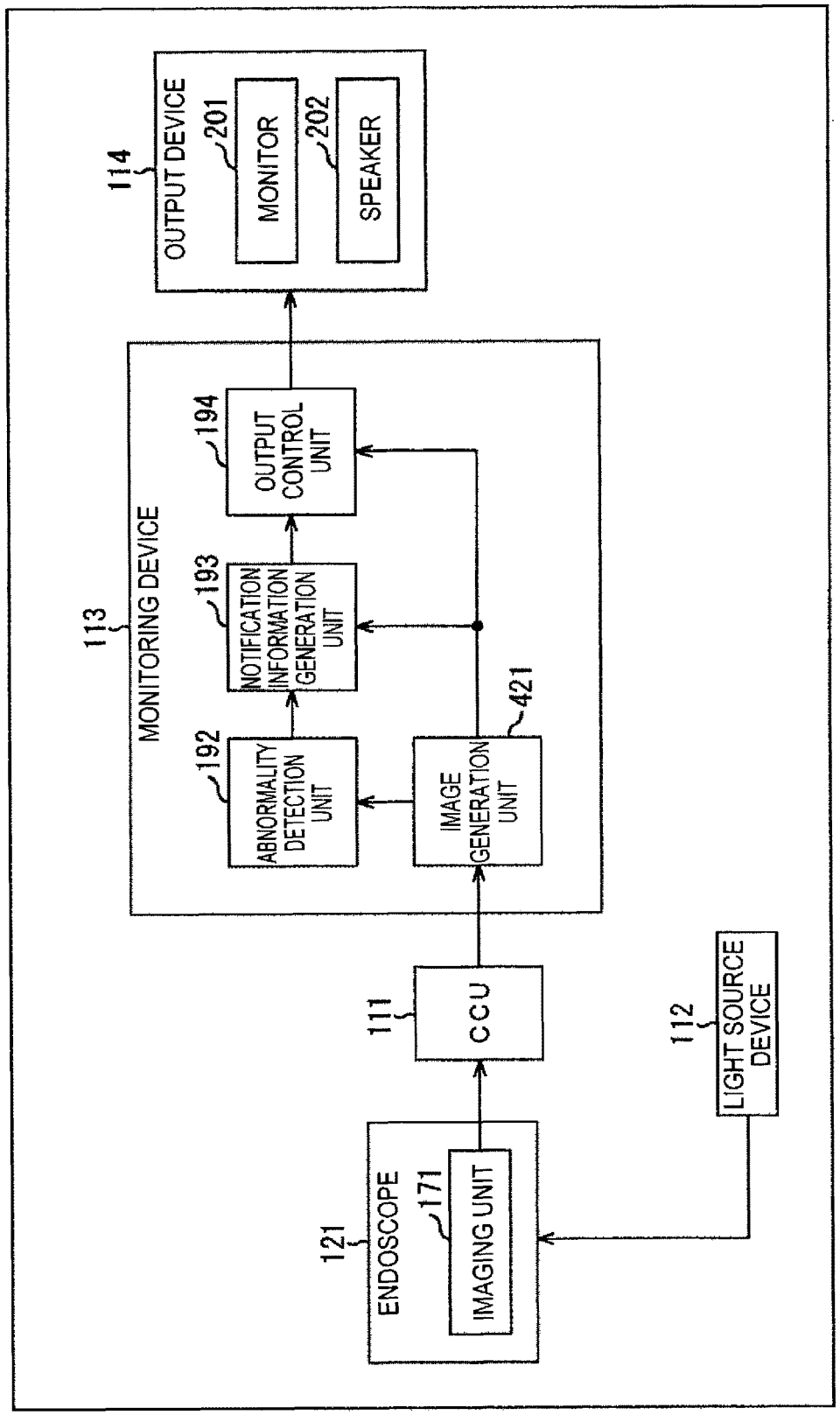

[Fig. 24]
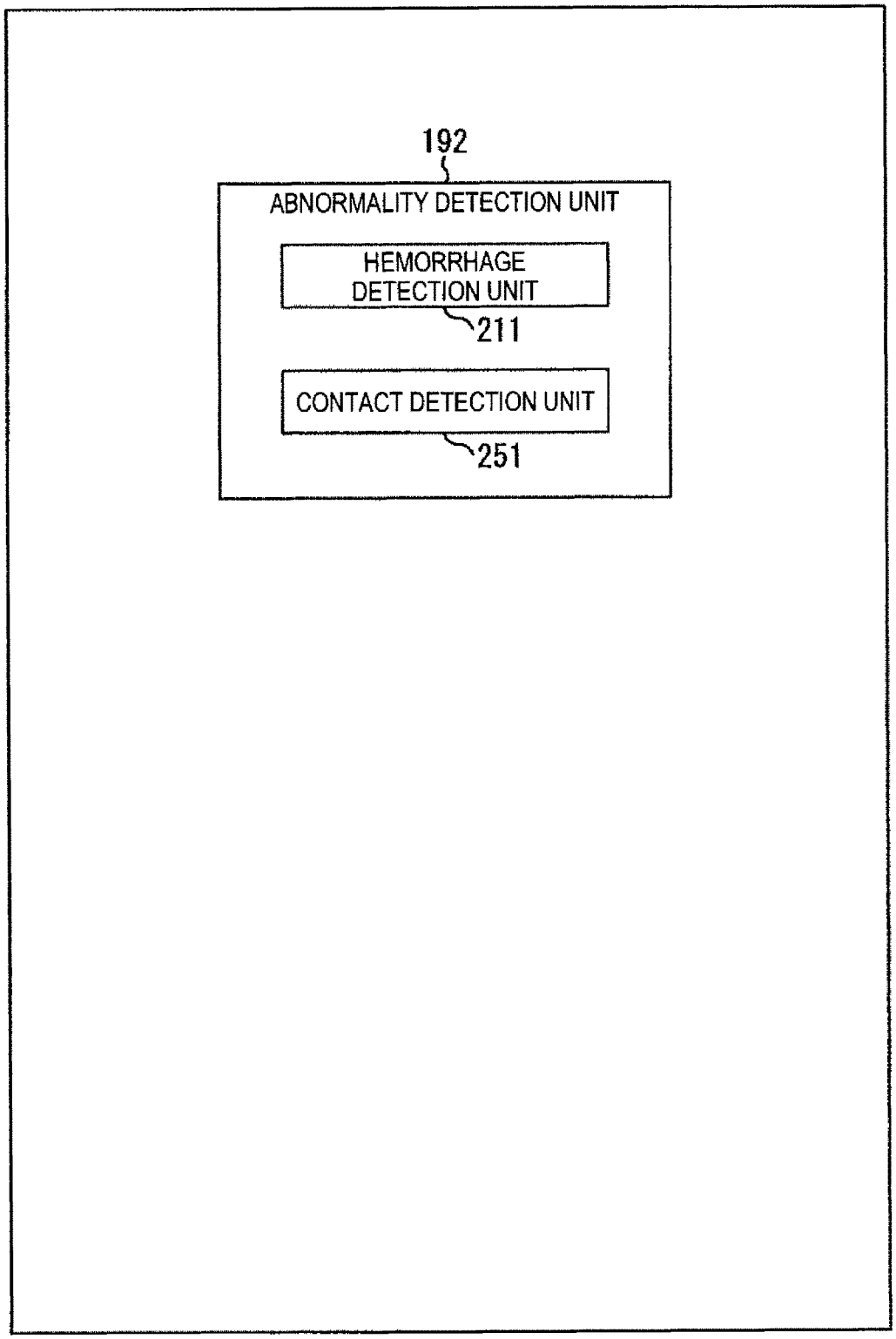

[Fig. 25]
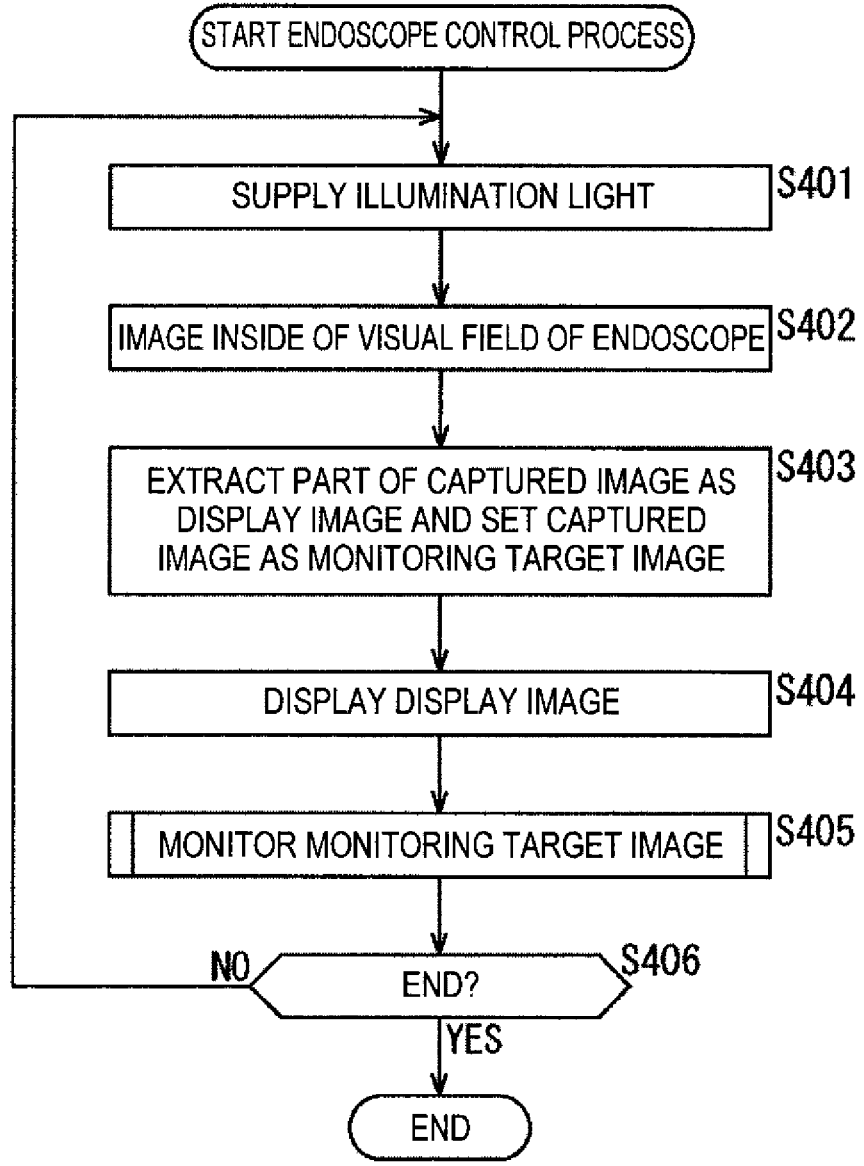

[Fig. 26]
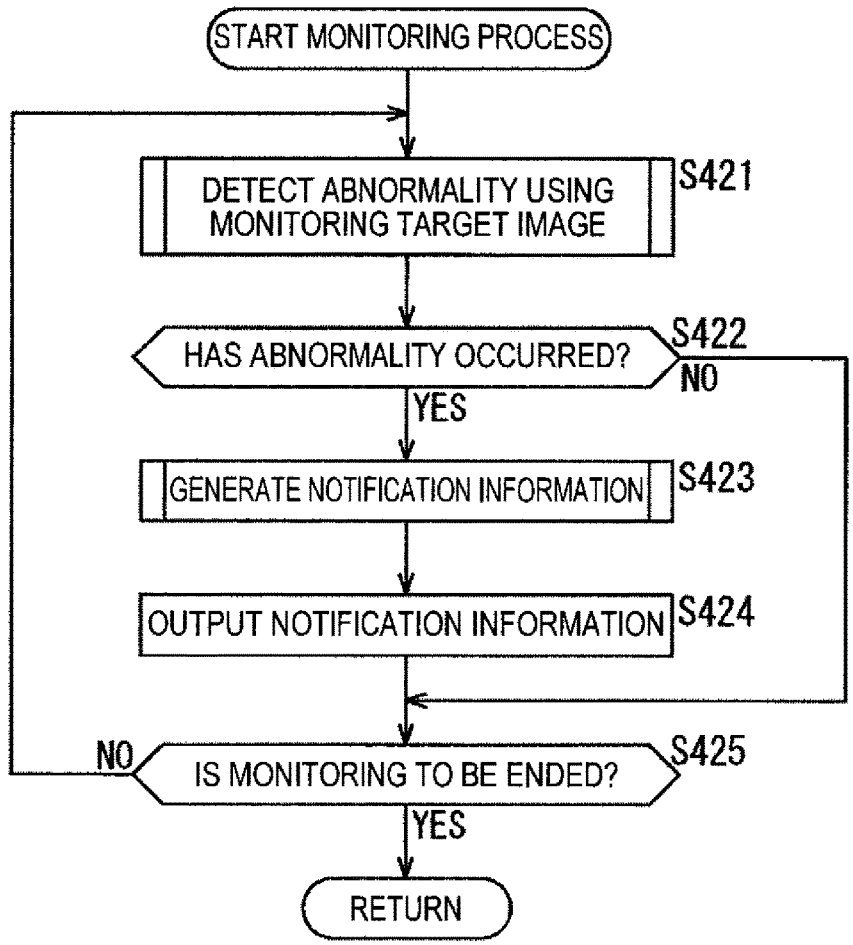
[Fig. 27]
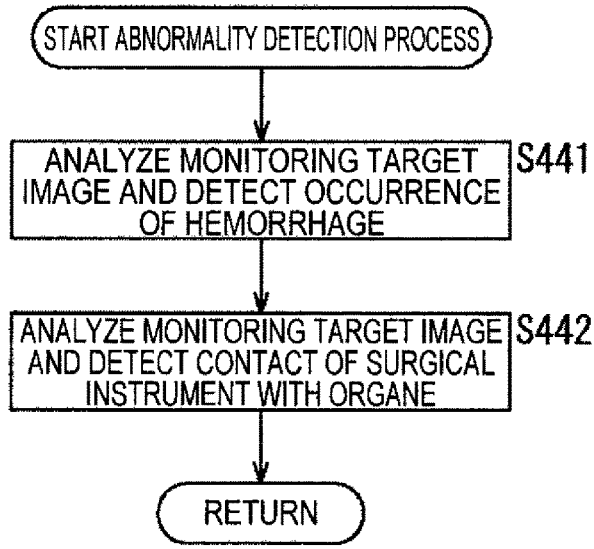

[Fig. 28]
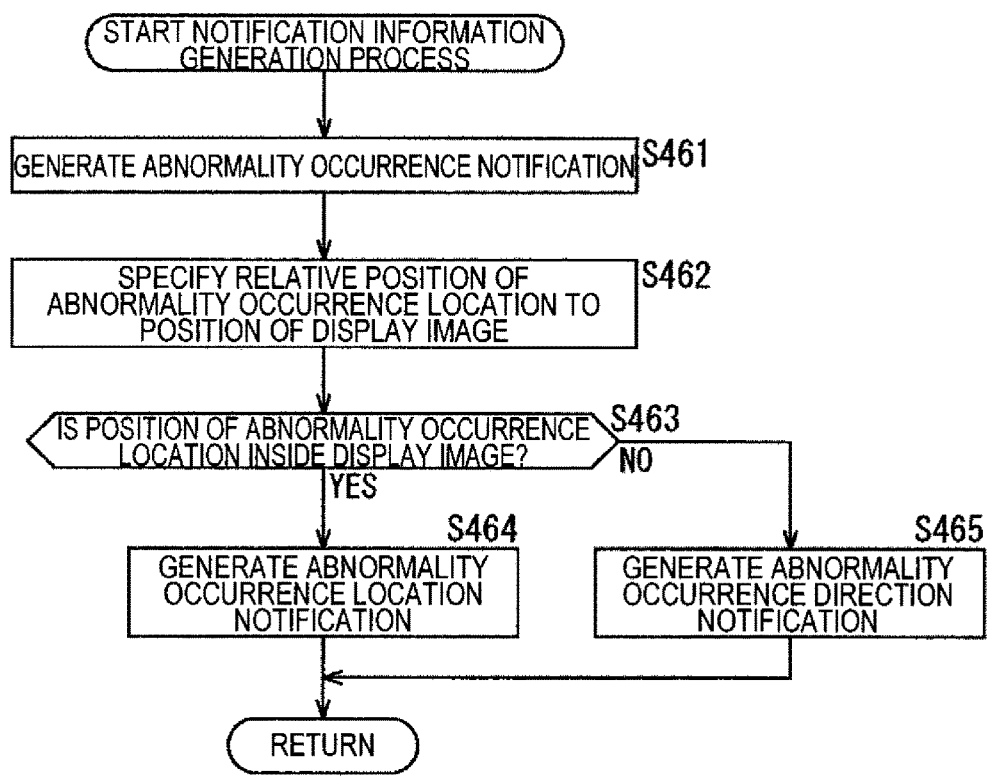

[Fig. 29]
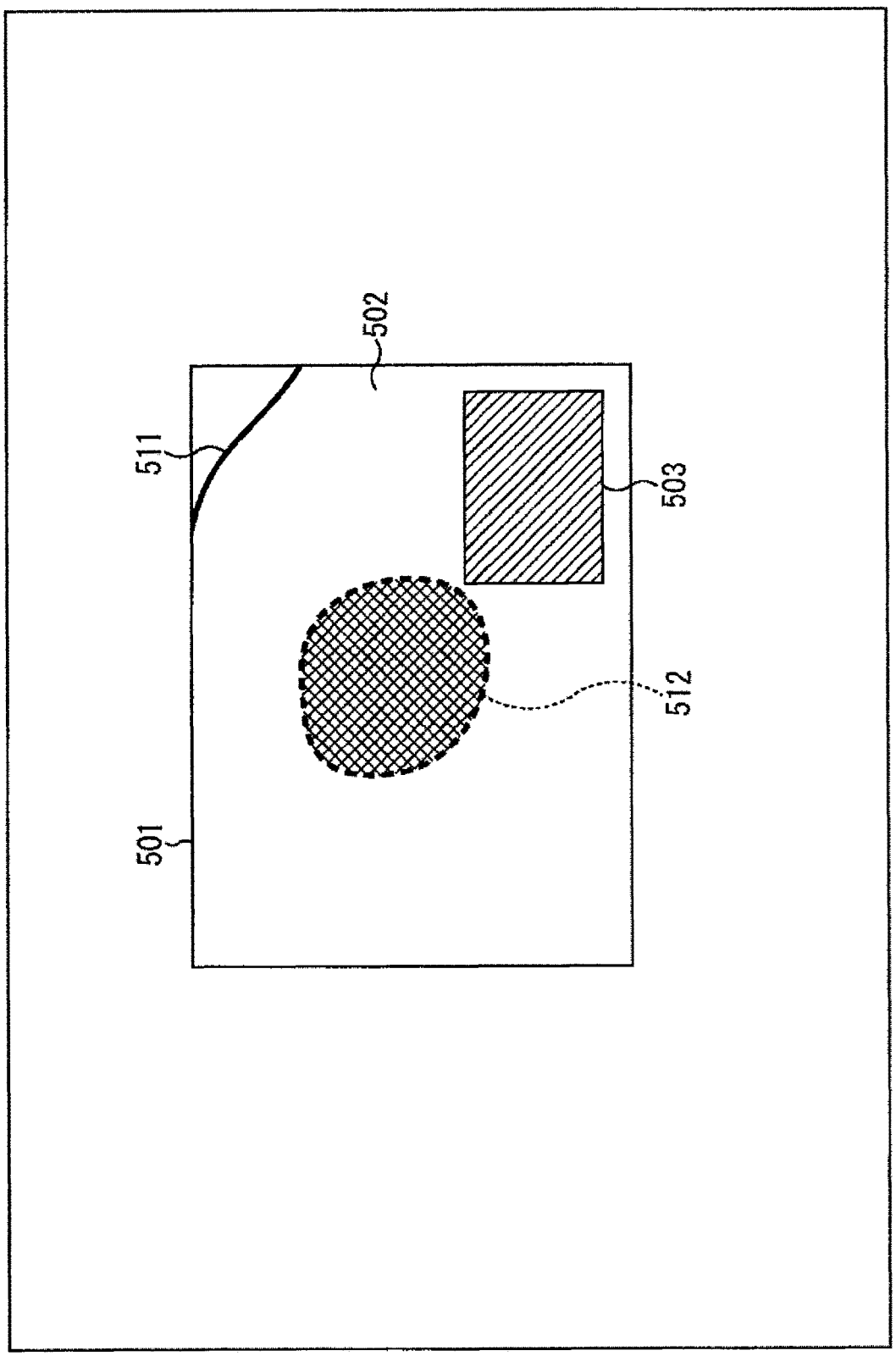

[Fig. 30]
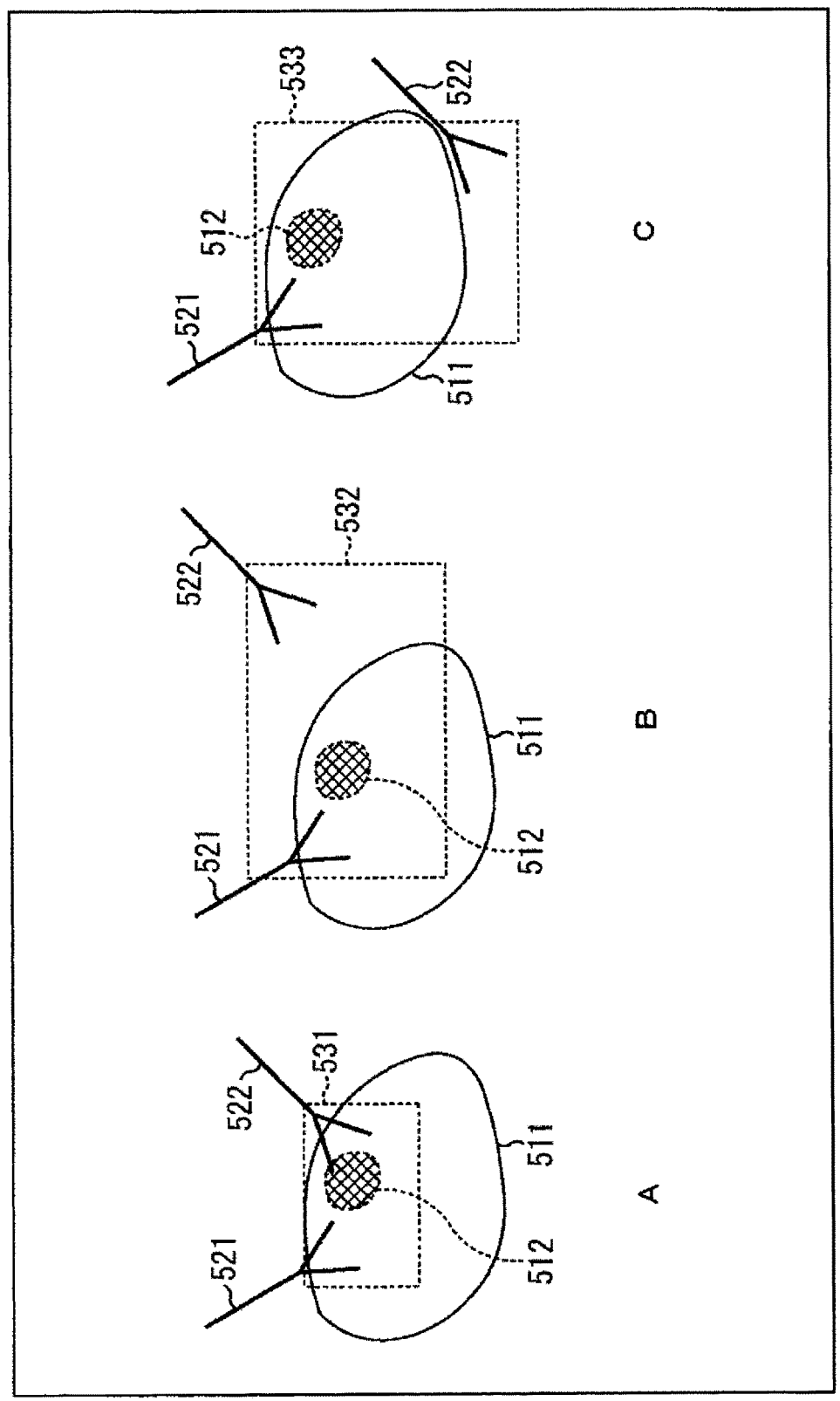

[Fig. 31]
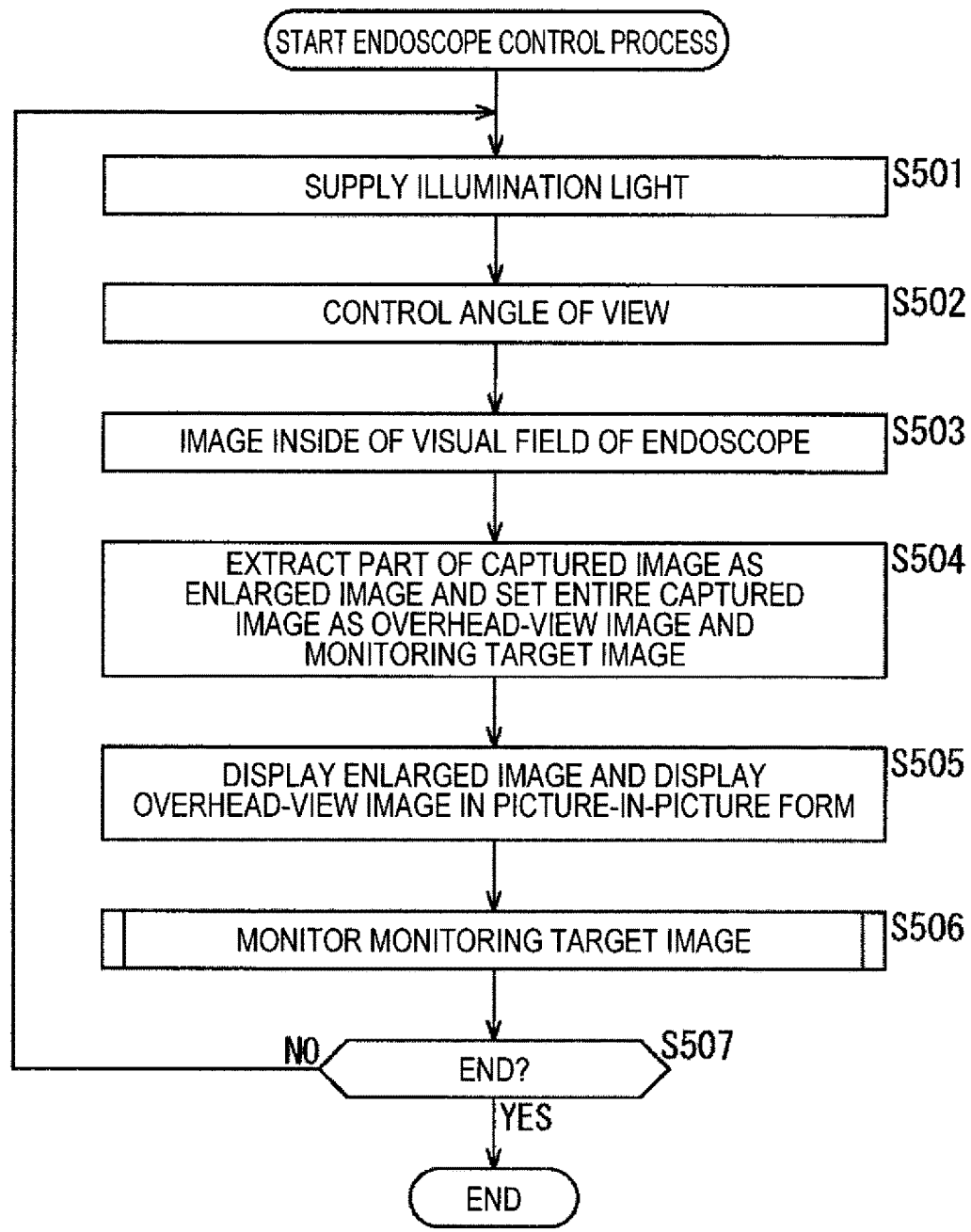

[Fig. 32]
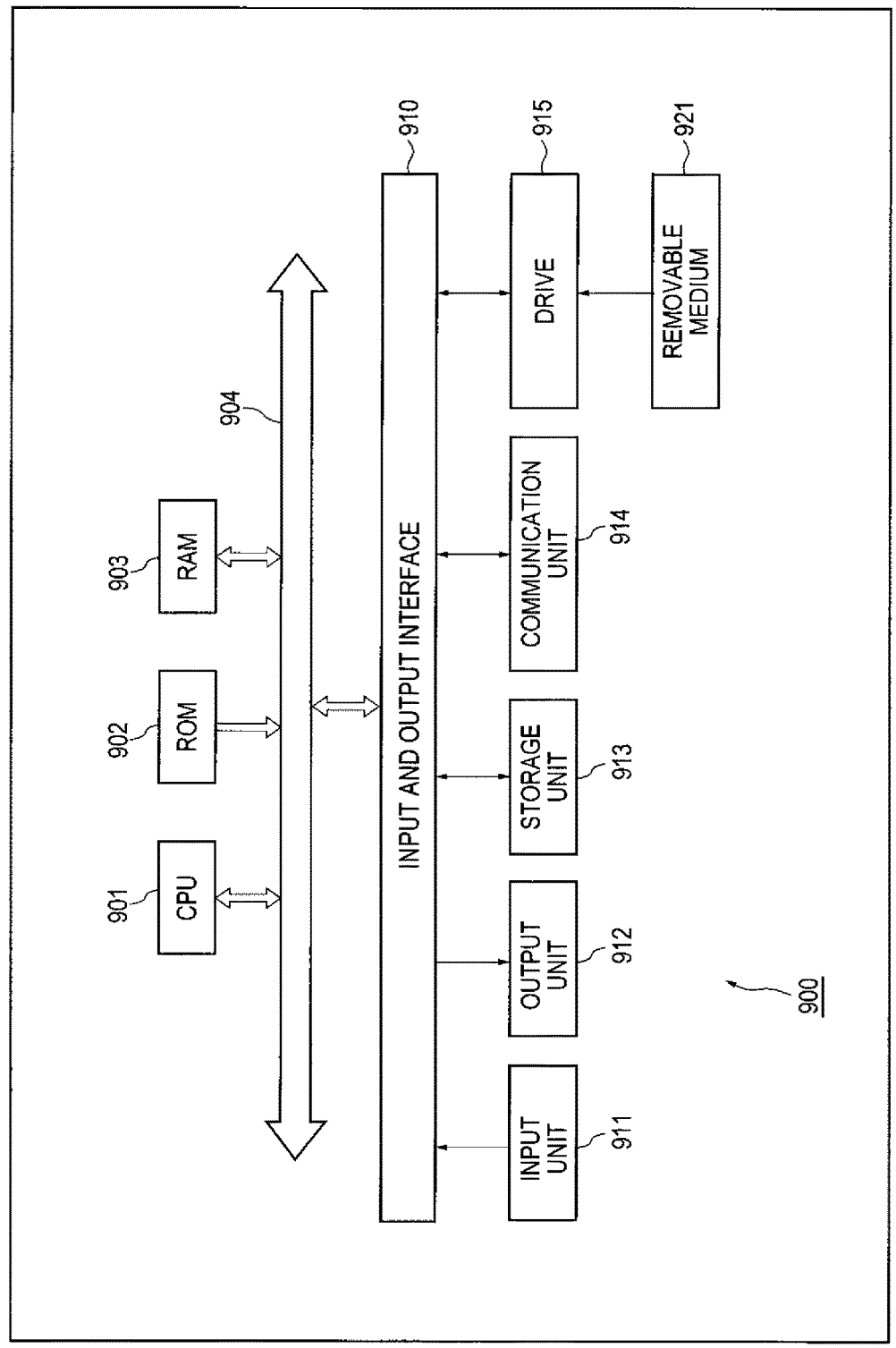

SURGICAL SYSTEM, INFORMATION PROCESSING DEVICE, AND METHOD

TECHNICAL FIELD

The present technology relates to a surgical system, an information processing device, a method, and particularly to an information processing device and a method which enable an abnormality occurring in a region inside the visual field of an endoscope or a region outside the visual field of the endoscope to be ascertained more easily.

CROSS REFERENCE TO RELATED APPLICATIONS

This application claims the benefit of Japanese Priority Patent Application JP 2015-063824 filed Mar. 26, 2015, the entire contents of which are incorporated herein by reference.

BACKGROUND ART

Endoscopic surgeries in which surgical operations are performed using an endoscope have been performed since the past. In endoscopic surgeries, an operator performs tasks while checking images of an operative field imaged by an endoscope on a monitor. For such an endoscope, various types of innovations to enable operators to easily perform tasks have been considered (for example, refer to PTL 1).

For example, PTL 1 discloses a method for reducing mismatch between the axis on which an endoscope camera acquires videos and the axis of a screen display unit of a monitor and thereby enabling an operator to perform tasks intuitively by performing positioning and holding the housing of the endoscope camera with respect to a target using protrusions provided on an outer surface of the housing.

CITATION LIST

Patent Literature

PTL 1: JP 5499426B

SUMMARY OF INVENTION

Technical Problem

However, monitoring occurrence of abnormalities is not performed with endoscopes of the related art including the endoscope disclosed in PTL 1. For this reason, when an abnormality such as a hemorrhage occurs in the periphery of a surgical site, for example, an operator merely visually finds the occurrence of the abnormality on an image of the operative field displayed on a monitor.

In general, however, since surgical sites are very small and a task to be performed by an operator is intricate, there are many cases in which an image of an operative field imaged by an endoscope is enlarged and displayed on a monitor to help an operator perform his or her task more easily. Consequently, the range of the visual field of the operator through the endoscope is limited to a very narrow range near the surgical site in most cases. For this reason, there is concern of the operator having difficulty finding occurrence of an abnormality or finding it too late. In addition, because operators perform intricate tasks on which they should fully concentrate, there is concern of an operator having difficulty recognizing an abnormality or recognizing it too late with only the display of an abnormality occurring in an operative field on a monitor.

As described above, there is concern of occurrence of an abnormality being difficult to find, an abnormality being found too late, or an operator failing to perform proper treatment on an abnormality that has occurred.

The present technology takes the above circumstances into consideration, and therefore aims to enable an abnormality occurring in a region inside or outside the visual field of an endoscope to be ascertained more easily.

Solution to Problem

According to an embodiment of the present technology, there is provided a surgical system including: a monitoring sensor configured to sense a characteristic of a surgical site within a body, in a sensing region of the surgical site which includes at least a part of a region outside a display field of an endoscope; and circuitry configured to detect an occurrence of a medical abnormality in the region outside the display field of the endoscope based on a result of the sensing by the monitoring sensor, and generate notification information regarding the detected medical abnormality.

According to an embodiment of the present technology, there is provided an information processing device, including: circuitry configured to detect an occurrence of a medical abnormality in a region outside a display field of an endoscope based on a result of sensing by a monitoring sensor configured to sense a characteristic of a surgical site within a body, in a sensing region of the surgical site which includes at least a part of the region outside the display field of the endoscope, and generate notification information regarding the detected medical abnormality.

According to an embodiment of the present technology, there is provided an information processing method, including: detecting an occurrence of a medical abnormality in a region outside a display field of an endoscope based on a result of sensing by a monitoring sensor configured to sense a characteristic of a surgical site within a body, in a sensing region of the surgical site which includes at least a part of the region outside the display field of the endoscope, and generating notification information regarding the detected medical abnormality.

Advantageous Effects of Invention

According to an embodiment of the present technology, information can be processed. In addition, according to an embodiment of the present technology, an abnormality occurring in a region inside or outside the visual field of an endoscope can be ascertained more easily.

BRIEF DESCRIPTION OF DRAWINGS

FIG. 1 is a diagram showing an example of a main configuration of an endoscopic surgery support system.

FIG. 2 is a diagram for describing the range of the visual field of an endoscope.

FIG. 3 is a block diagram showing an example of a main configuration of a monitoring device and the like.

FIG. 4 is a functional block diagram showing an example of a main function of an abnormality detection unit.

FIG. 5 is a functional block diagram showing an example of a main function of a notification information generation unit.

FIG. 6 is a flowchart describing an example of the flow of an endoscope control process.

FIG. 7 is a flowchart describing an example of the flow of a monitoring process.

FIG. 8 is a flowchart describing an example of the flow of an abnormality detection process.

FIG. 9 is a flowchart describing an example of the flow of a notification information generation process.

FIG. 10 is a diagram for describing an example of a display image.

FIG. 11 is a block diagram showing another example of the main configuration of the monitoring device and the like.

FIG. 12 is a functional block diagram showing another example of the main function of the abnormality detection unit.

FIG. 13 is a flowchart describing another example of the flow of the abnormality detection process.

FIG. 14 is a block diagram showing still another example of the main configuration of the monitoring device and the like.

FIG. 15 is a functional block diagram showing another example of the main function of the notification information generation unit.

FIG. 16 is a flowchart describing another example of the flow of the endoscope control process.

FIG. 17 is a flowchart describing another example of the flow of the monitoring process.

FIG. 18 is a flowchart describing another example of the flow of the notification information generation process.

FIG. 19 is a flowchart describing an example of the flow of a notification information output process.

FIG. 20 is a diagram for describing an example of an image for monitoring.

FIG. 21 is a diagram for describing an example of a captured image, a display image, and a sensing range.

FIG. 22 is a diagram for describing another example of a captured image, a display image, and a sensing range.

FIG. 23 is a block diagram showing still another example of the main configuration of the monitoring device and the like.

FIG. 24 is a functional block diagram showing still another example of the main function of the abnormality detection unit.

FIG. 25 is a flowchart describing still another example of the flow of the endoscope control process.

FIG. 26 is a flowchart describing still another example of the flow of the monitoring process.

FIG. 27 is a flowchart describing still another example of the flow of the abnormality detection process.

FIG. 28 is a flowchart describing still another example of the flow of the notification information generation process.

FIG. 29 is a diagram for describing an example of a display image.

FIG. 30 is a diagram for describing an example of the range of an overhead-view image.

FIG. 31 is a flowchart describing still another example of the flow of the endoscope control process.

FIG. 32 is a block diagram showing an example of a main configuration of a computer.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted. Note that description will be provided in the following order.

1. First embodiment (endoscopic surgery support system)
2. Second embodiment (endoscopic surgery support system)
3. Third embodiment (endoscopic surgery support system)
4. Fourth embodiment (endoscopic surgery support system)
5. Fifth embodiment (endoscopic surgery support system)
6. Sixth embodiment (computer)

1. First Embodiment

<Occurrence of an Abnormality in the Periphery of a Surgical Site>

Endoscopic surgeries in which surgical operations are performed using endoscopes (for example, a laparoscopic surgery or the like) have been performed since the past. In an endoscopic surgery, an operator who conducts a surgical operation performs a task while checking an image of an operative field (the visual field which includes the surgical site that is the spot at which the task is performed) imaged by an endoscope from a monitor.

Monitoring occurrence of abnormalities, however, is not performed with endoscopes of the related art. For this reason, when an abnormality such as a hemorrhage occurs in the periphery of a surgical site, for example, an operator merely visually finds the occurrence of the abnormality on an image of the operative field displayed on the monitor.

In general, however, since surgical sites are very small and a task to be performed by an operator is intricate, there are many cases in which an image of an operative field imaged by an endoscope is enlarged and displayed on a monitor to help the operator perform the task more easily. Consequently, the range of the visual field of the operator through the endoscope is limited to a very narrow range near the surgical site in most cases. For this reason, there is concern of the operator having difficulty finding occurrence of an abnormality or finding it too late.

For example, an abnormality such as a hemorrhage may occur due to unnecessary contact of a surgical instrument with an organ or the like. With regard to this, since the range of the visual field of an operator through an endoscope is narrow as described above, it is difficult to position all surgical instruments within the range. In other words, there is a possibility of a hemorrhage occurring in other range due to unnecessary contact of a surgical instrument with an organ or the like. In such a case, the occurrence of a hemorrhage is not displayed on a monitor, and thus it is difficult for the operator to identify the hemorrhage.

A case in which, for example, blood being discharged flows in the range displayed on a monitor and an operator finds the hemorrhage is also considered, but in this case, there is also concern of a hemorrhage being found too late by the operator.

In addition, in such a case, there is concern that, after finding the hemorrhage, the operator should check the spot of the hemorrhage by moving the imaging range of the endoscope, which necessitates a complicated task and time for the checking. Furthermore, failure to check is also considered. Furthermore, while checking the spot of the hemorrhage, the operator should stop treating the surgical site.

Difficulty in finding occurrence of an abnormality, not finding an abnormality in time, and failure of an operator to perform proper treatment for an abnormality that has occurred are concerns.

Note that widening the angle of view of an endoscope has also been considered in order to enable operators to find occurrence of abnormalities in a wide range; however, there is concern in such a case of an image of a surgical site to which an operator wants to pay attention becoming small and hard to view, and as a result, a task becoming difficult (consequently, convenience of an endoscope deteriorates).

In addition, there are cases in which an operator performs intricate tasks on which he or she should fully concentrate. For this reason, even if the occurrence position of an abnormality is within a display range (i.e., even if an abnormality is displayed on a monitor), there is concern of the operator having difficulty recognizing the abnormality or finding the abnormality too late with only display of the abnormality on the monitor.

Therefore, it is desirable to enable abnormalities occurring in a region inside or outside the visual field of an endoscope to be ascertained more easily.

<Endoscopic Surgery Support System>

FIG. 1 is a diagram showing an example of a main configuration of an endoscopic surgery support system including a monitoring device which is an embodiment of an information processing device to which an embodiment of the present technology is applied.

In FIG. 1, the endoscopic surgery support system 100 is a system which is used by an operator and the like in endoscopic surgeries (for example, laparoscopic surgeries and the like) to support the surgeries. An endoscopic surgery is a surgical operation in which a few small holes are opened in the body (for example, the abdomen or the like) of a patient who is undergoing the operation, an endoscope or the like is inserted from the holes, and treatment is performed while a monitor is viewed. Such an endoscopic surgery has characteristics of being minimally invasive, lightening a burden on patients, enabling quicker recovery, and the like in comparison to laparotomies.

A state in which the patient 151 who is undergoing an endoscopic surgery lies on a patient bed 141, small holes are opened in the body surface of the patient 151 near a surgical site, and trocars which are hole-opening instruments are deployed to open each opening part is maintained. In the example of FIG. 1, five holes are opened in the body of the patient 151, and the trocars 131-1 to 131-5 are deployed therein. When it is not necessary to distinguish the trocars 131-1 to 131-5 from each other hereinbelow, they will be referred to as trocars 131.

In an endoscopic surgery, surgical instruments used in a surgical operation (for example, electrical scalpels, scissors, tweezers, forceps, and the like) are inserted through the holes opened by the trocars 131. In the example of FIG. 1, an endoscope 121, an energy device 122, forceps 123, a pneumoperitoneum needle 124, and a monitoring sensor 125 are used as surgical instruments.

The endoscope 121 is a device for imaging a surgical site and the like as described above. The endoscope 121 performs imaging using light supplied from a light source device 112 when the light is radiated inside the body of the patient 151 (the surgical site or the periphery). The endoscope 121 supplies information regarding a captured image obtained from imaging (for example, captured image data or the like) to a CCU 111. In the example of FIG. 1, the endoscope 121 is inserted into the body of the patient 151 through the hole opened by the trocar 131-1.

The energy device 122 is a surgical instrument, for example, an electric scalpel which uses electric energy. Like an electric scalpel, for example, the energy device 122 can generate Joule heat from a load or contact resistance when the device causes a high-frequency current to flow in a surgical site. The heat instantly heats up a cell to cause it to explode and transpire, resulting in an incision action. In addition, the heat evaporates moisture of the cell and coagulates protein, resulting in a coagulation action. In the example of FIG. 1, the energy device 122 is inserted into the body of the patient 151 through the hole that is opened by the trocar 131-2.

The forceps 123 is an instrument for grasping tissues. The forceps 123 resembles scissors, has stoppers that are held, and thus can hold an object interposed therebetween. The forceps can be used in various applications such as pinching, pulling, crushing, opening, picking up, blocking, and the like. In the example of FIG. 1, the forceps 123 is inserted into the body of the patient 151 through the hole opened by the trocar 131-3.

The pneumoperitoneum needle 124 sends a gas (carbon dioxide gas or the like) into the body of the patient or sucks a gas from inside the body of the patient 151. The pneumoperitoneum needle 124 is connected with a pneumoperitoneum device 116 via a predetermined tube, and a gas sent into the body of the patient 151 is supplied from, for example, the pneumoperitoneum device 116. In addition, a gas sucked from the inside of the body of the patient 151 is supplied to, for example, the pneumoperitoneum device 116. In the example of FIG. 1, the pneumoperitoneum needle 124 is inserted into the body of the patient 151 through the hole opened by the trocar 131-4.

The monitoring sensor 125 senses (detects) occurrence of an abnormality in a target region. Such a region in which this sensing is performed (target region) is also referred to as a sensing region. The monitoring sensor 125 supplies information regarding a result of the sensing (for example, data obtained from the sensing or the like) to a monitoring device 113. In the example of FIG. 1, the monitoring sensor 125 is inserted into the body of the patient 151 through the hole opened by the trocar 131-5. Hence, a predetermined range inside the body of the patient 151 (for example, the surgical site and the periphery thereof, and the like) is set as a target sensing region.

The type and number of sensors included in the monitoring sensor 125 are arbitrary. That is, the monitoring sensor 125 can sense occurrence of abnormalities with respect to arbitrary parameters. For example, the monitoring sensor 125 may be set to sense occurrence of abnormalities with respect to at least one of an image, light, electricity, sound, vibration, acceleration, speed, angular velocity, force, temperature, humidity, flow rate, magnetism, a chemical substance, and odor. In addition, the monitoring sensor 125 may perform sensing with a plurality of sensors for one parameter. Furthermore, the monitoring sensor 125 may be set to further sense an attitude of the monitoring sensor 125.

As illustrated in FIG. 1, the endoscopic surgery support system 100 has, for example, the camera control unit (CCU) 111, the light source device 112, the monitoring device 113, an output device 114, a surgical instrument control device 115, the pneumoperitoneum device 116, and the like.

The CCU 111 controls driving of the endoscope 121. For example, the CCU 111 supplies information regarding control to the endoscope 121, and controls driving of an observation optical system (for example, lenses, stops, image sensors, and the like) of the endoscope 121. In addition, the CCU 111 can also acquire information regarding captured images of the inside of the patient 151 (for example, the surgical site and the periphery thereof) imaged through the observation optical system of the endoscope 121. Furthermore, the CCU 111 can perform signal processing such as image processing and the like on captured image data included in the acquired information. For example, the CCU 111 and the endoscope 121 may be set such that they are electrically connected to each other via a predetermined cable to perform communication with each other via the cable (wired communication), thereby exchanging various kinds of information through the wired communication. In addition, the CCU 111 and the endoscope 121 may be set such that they perform wireless communication with each other and exchange various kinds of information through the wireless communication. In that case, the above-mentioned cable may be omitted, or both wired and wireless communication may be used.

The light source device 112 is connected to the endoscope 121 through a light guide cable to supply a light source that is necessary for imaging of the endoscope 121 to the endoscope 121 through the light guide cable.

The light source device 112 can switch and emit light of various wavelengths. In addition to normal light, for example, the light source device 112 can emit special light which can specifically identify a lesion (for example, narrow-band light, infrared light, or the like). Thus, the endoscope 121 can obtain image signals (captured images) of special light as well as image signals (captured images) of normal light.

The monitoring device 113 is a device which monitors occurrence of abnormalities inside the body of the patient 151. The monitoring device 113 detects occurrence of an abnormality in, for example, a region outside the visual field of the endoscope 121 based on the result of sensing of a sensing region including at least a part of the region outside the visual field, and generates notification information for performing notification regarding the detected abnormality. By generating and providing the notification information regarding the occurrence of the abnormality as described above, the monitoring device 113 can ascertain the abnormality occurring in the region inside and outside the visual field of the endoscope more easily. The region inside and outside the visual field will be described below.

The sensing is performed by, for example, the monitoring sensor 125. The monitoring device 113 acquires information regarding the result of the sensing from the monitoring sensor 125. In addition, the monitoring device 113 may be set to supply information regarding control to the monitoring sensor 125 to control sensing of the monitoring sensor 125.

The monitoring device 113 and the monitoring sensor 125 may be set such that, for example, they are electrically connected via a predetermined cable to perform communication with each other via the cable (wired communication) and to exchange various kinds of information through the wired communication. In addition, the monitoring device 113 and the monitoring sensor 125 may be set to perform wireless communication with each other and exchange various kinds of information through the wireless communication. In this case, the above-mentioned cable may be omitted, or both wired and wireless communication may be used.

In addition, for example, the endoscope 121 may also perform predetermined sensing and the monitoring device 113 may acquire information regarding a result of the sensing obtained by the endoscope 121. Furthermore, the monitoring device 113 may supply information regarding control to the endoscope 121 to be able to control sensing of the endoscope 121.

The monitoring device 113 and the endoscope 121 may be set such that, for example, they are electrically connected via a predetermined cable to perform communication with each other via the cable (wired communication) and exchange various kinds of information through the wired communication. In addition, the monitoring device 113 and the endoscope 121 may be set to perform wireless communication with each other to exchange various kinds of information through the wireless communication. In this case, the above-mentioned cable may be omitted, or both wired and wireless communication may be used.

The output device 114 outputs information supplied from other devices. For example, the output device 114 may be set to output notification information regarding occurrence of an abnormality supplied from the monitoring device 113. The output device 114, for example, may be set to include a monitor which is a display unit on which images are displayed to display an image of the notification information regarding occurrence of an abnormality supplied from the monitoring device 113 thereon. In addition, the output device 114 may be set to further display an image of a region inside the visual field supplied from the monitoring device 113 on the monitor. Furthermore, the output device 114 may be set to further display an image regarding a result of sensing supplied from the monitoring device 113 on the monitor.

The output device 114, for example, may be set to include a speaker which is a sound output unit that outputs sounds to output a sound of the notification information regarding occurrence of an abnormality supplied from the monitoring device 113 from the speaker. In addition, the output device 114 may be set to further output the sound relating to a result of sensing supplied from the monitoring device 113 from the speaker.

The surgical instrument control device 115 controls driving of the energy device 122. For example, the surgical instrument control device 115 and the energy device 122 are set to be electrically connected via a predetermined cable, the surgical instrument control device 115 causes a high-frequency current or the like to be supplied to the energy device 122 via the predetermined cable, and thus the energy device 122 is capable of excising a lesion with the electric heat.

The pneumoperitoneum device 116 supplies a gas (for example, carbon dioxide gas or the like) to the pneumoperitoneum needle 124 via the predetermined tube to supply (send) the gas from the pneumoperitoneum needle 124 into the body of the patient 151, thereby dilating the inside of the body (the periphery of the surgical site). Accordingly, a space in which a task can be performed can be secured inside the body (the periphery of the surgical site). In addition, the pneumoperitoneum device 116 can also suck (intake) a gas (for example, carbon dioxide gas or the like) from inside the body of the patient 151 from the pneumoperitoneum needle 124 via the predetermined tube.

Note that a surgical instrument used in an endoscopic surgery is arbitrary and is not limited to the above examples. In addition, some of the above-described surgical instruments may not be used. Furthermore, the number of surgical instruments to be used is also arbitrary. The same surgical instrument may be used a plurality of times.

A device constituting the endoscopic surgery support system 100 is also arbitrary, and is not limited to the above examples. In addition, some of the above-described devices may not be included. Furthermore, the number of devices is also arbitrary. The same device may be used a plurality of times.

<Visual Field of an Endoscope and Range of Sensing>

Next, the range of the visual field of the endoscope 121 and the range of sensing will be described. In an endoscopic surgery, an operator performs a surgical operation (task) while viewing images captured by an endoscope and displayed on a monitor. Thus, the images captured by (an imaging unit of) the endoscope and displayed on the monitor become the visual field of the operator through the endoscope (which will also be referred to as the visual field of the endoscope).

Thus, the range of the visual field of the endoscope is limited (equal to or narrower than the imaging range of the endoscope). For example, when the monitor displays an enlarged (digitally zoomed-in) partial image of a captured image, the range of the visual field of the endoscope is narrower than the imaging range. A region in the range of the visual field of the endoscope (which is the visual field of the endoscope), i.e., a region imaged by the endoscope and displayed on a monitor, is referred to as a region inside the visual field. In addition, a region other than the region inside the visual field is referred to as a region outside the visual field. For example, the region outside the visual field includes regions in the range imaged by (the imaging unit of) the endoscope (which is also referred to as an imaging region) but is not displayed on a monitor. In addition, when the radiation range of light to be radiated for imaging of the endoscope (which is also referred to as a light radiation region) also includes regions outside the imaging region, a region outside the visual field also includes a region outside the imaging region included in the light radiation region. Furthermore, the region outside the visual field also includes a region outside the regions (light radiation region and imaging region).

FIG. 2 is a diagram showing an example of a region inside the visual field and a region outside the visual field. In the example of FIG. 2, the region inside the visual field 162 is a region including a lesion 161 in which an operator performs a task and the periphery thereof, and the region outside the visual field 163 is a region other than the region inside the visual field 162. Since it is necessary to display a surgical site to be larger on a monitor as described above, the region inside the visual field 162 is set in a very narrow range as shown in the example of FIG. 2. In other words, as the region inside the visual field 162 becomes narrower, the region outside the visual field 163 becomes wider. Accordingly, there is a high possibility of a position in which an abnormality such as a hemorrhage occurs being located in the region outside the visual field 163, and therefore it becomes more difficult for an operator to visually detect the occurrence of the abnormality.

Thus, it is possible to set occurrence of an abnormality in the region outside the visual field 163 to be detected. That is, the monitoring device 113 is set to detect occurrence of an abnormality in the region outside the visual field based on a result of sensing of the sensing region which includes at least a part of the region outside the visual field of the endoscope 121 and to generate notification information for performing notification regarding the detected abnormality. Sensing in the region outside the visual field 163 is performed using, for example, the monitoring sensor 125.

Since the monitoring sensor 125 is used for detecting occurrence of abnormalities, it is not necessary that it be as highly accurate (have high resolution) as the imaging unit 171 of the endoscope 121. For this reason, the sensing range of the monitoring sensor 125 can be easily set to be a wider range than the imaging range of the imaging unit 171 by using, for example, a wide-angle lens or the like. In addition, a sensing region of the monitoring sensor 125 may include at least a part of the region outside the visual field of the endoscope 121, and the size, shape, and the like of the region are arbitrary. For example, the sensing region may be set to include a part of or the entire region inside the visual field of the endoscope 121. That is, sensing can be performed not only in the region outside the visual field 163 but also in the region inside the visual field 162. In other words, the sensing region of the monitoring sensor 125 may include a part of or the entire imaging region of the endoscope 121, or may include a part of or the entire light radiation region of the endoscope 121. Furthermore, the sensing region may include a part of or the entire region other than those regions (the region inside the visual field, the imaging region, the light radiation region, and the like).

Note that the size, shape, and the like of the region inside the visual field are arbitrary. Although the region inside the visual field 162 in the example of FIG. 2 appears as a circular region, the region may have, for example, a polygonal shape, an elliptical shape, or the like. In addition, the region inside the visual field may have, for example, a three-dimensional shape. Furthermore, for example, at least a part of the region inside the visual field may have a surface other than a plane such as a spherical surface, a curved surface, or the like. In addition, although illustrated in a circular shape in FIG. 2, the region outside the visual field is a region other than the region inside the visual field, and thus the size, shape, and the like thereof are arbitrary. Furthermore, the size, shape, and the like of the imaging region and the light radiation region are arbitrary.

Although the lesion 161 is positioned near the center of the region inside the visual field 162 in the example of FIG. 2, the endoscope 121 can perform imaging for an arbitrary position and direction. That is, the endoscope 121 can image a portion other than the lesion 161, and in that case, the lesion 161 can be positioned outside the region inside the visual field 162. In other words, by controlling a position and a direction of the endoscope 121, an operator or the like can set a portion other than the lesion 161 to be included within the region inside the visual field 162 and to be displayed on the monitor.

<Example of a Main Configuration of a Monitoring Device, Etc.>

FIG. 3 is a block diagram showing an example of a main configuration of the monitoring device 113 and the like. In the example of FIG. 3, the endoscope 121 has the imaging unit 171 and a gyro sensor 172.

The imaging unit 171 is a so-called image sensor and has a plurality of pixels which photoelectrically convert incident light. The endoscope 121 radiates light supplied from the light source device 112 on the light radiation region. The imaging unit 171 obtains an image of a subject (captured image of the imaging region) by photoelectrically converting radiation light reflected on the subject using the plurality of pixels. That is, the light radiation region and the imaging region are regions at substantially the same position. Of course, the sizes and shapes of the imaging region and the light radiation region may not coincide with each other. As described above, the imaging unit 171 images the subject and thereby obtains an image signal (captured image data) of the image of the subject. Information regarding the captured image obtained by the imaging unit 171 is supplied to the CCU 111 through communication between the endoscope 121 and the CCU 111. The imaging unit 171 is driven under control of the CCU 111 to perform such imaging.

The gyro sensor 172 performs sensing for information regarding an attitude of the endoscope 121. For example, the gyro sensor 172 senses a variation of an angular velocity or an angle of the endoscope 121 in each direction (i.e., a slope or a variation of the slope of the endoscope 121 in each direction). Information regarding the result of sensing performed by the gyro sensor 172 is supplied to the monitoring device 113 through communication between the endoscope 121 and the monitoring device 113. This information regarding the result of sensing is used to estimate a position of the region inside the visual field of the endoscope 121 as will be described below.

The gyro sensor 172 may be driven under control of, for example an external device (for example, the CCU 111 or the monitoring device 113), may be driven under control of an operator or the like, or may be driven without being controlled by them.

In the example of FIG. 3, the monitoring sensor 125 has a thermo sensor 181 and a gyro sensor 182.

The thermo sensor 181 performs sensing for information regarding a temperature of a sensing region. For example, the thermo sensor 181 senses temperature distribution in a sensing region. Note that the temperature may be an absolute value or a relative value to a predetermined reference. Information regarding the result of sensing obtained by the thermo sensor 181 is supplied to the monitoring device 113 through communication between the monitoring sensor 125 and the monitoring device 113.

The gyro sensor 182 performs sensing for information regarding an attitude of the monitoring sensor 125. Sensing in this case is the same as that of the gyro sensor 172. Information regarding the result of sensing performed by the gyro sensor 182 is supplied to the monitoring device 113 through communication between the monitoring sensor 125 and the monitoring device 113. As in the case of the gyro sensor 172, the information regarding the result of the sensing is used to estimate a position of the region inside the visual field of the endoscope 121.

The monitoring sensor 125 (the thermo sensor 181 and the gyro sensor 182) may be driven under control of, for example, an external device (for example, the monitoring device 113), may be driven under control of an operator or the like, or may be driven without being controlled by them.

Note that, when the information regarding an attitude of the endoscope 121 or the monitoring sensor 125 is not used in estimating a position of the region inside the visual field of the endoscope 121, or when a position of the region inside the visual field of the endoscope 121 is not estimated, the gyro sensor 172 or the gyro sensor 182 may be omitted.

In the example of FIG. 3, the monitoring device 113 has a visual field position estimation unit 191, an abnormality detection unit 192, a notification information generation unit 193, and an output control unit 194.

The visual field position estimation unit 191 estimates a position of the region inside the visual field of the endoscope 121. The visual field position estimation unit 191 acquires, for example, the information regarding the result of sensing performed by the thermo sensor 181 from the monitoring sensor 125, and estimates a position of the region inside the visual field based on the information. That is, in this case, the visual field position estimation unit 191 estimates the position of the region inside the visual field within the sensing region.

In such estimation of a position of the region inside the visual field within the sensing region, the visual field position estimation unit 191 first specifies the region inside the visual field based on a result of sensing. The visual field position estimation unit 191 specifies, for example, a region having a higher temperature than the periphery in temperature distribution obtained by the thermo sensor 181 as the region inside the visual field of the endoscope 121.

For example, the imaging unit 171 performs imaging using reflection light of light radiated by the endoscope 121 as described above. Thus, the position of the region inside the visual field and the position of the light radiation region substantially coincide and light from the endoscope 121 is radiated on the region inside the visual field. For this reason, the temperature of the region inside the visual field can be assumed to increase more than that of the region outside the visual field due to the heat of the radiated light. The visual field position estimation unit 191 specifies the region inside the visual field of the endoscope 121 using the increase. Note that, strictly speaking, only the light radiation region can be specified based on temperature distribution in this technique, and thus it is difficult to accurately specify the imaging region or the region inside the visual field; however, the visual field position estimation unit 191 may be set to accomplish such specification using an arbitrary technique so that the region inside the visual field can be specified more accurately. In addition, when the imaging region and the region inside the visual field do not coincide, for example, it is desirable to cause the visual field position estimation unit 191 to reflect the setting in specification of the region inside the visual field.

Note that temperature distribution of the region outside the visual field is not uniform at all times, and cases in which there are regions other than the region inside the visual field having a higher temperature than the peripheries (that is, there are a plurality of regions having a higher temperature than the peripheries and there are a plurality of candidates for the region inside the visual field) are also considered. With regard to this, the visual field position estimation unit 191 may be set to narrow down the candidates based on the characteristic of a temperature increase caused by light radiated from the endoscope 121.

For example, the visual field position estimation unit 191 may also be set to narrow down the candidates under the condition that a region having a higher temperature than the periphery is specified as a candidate for the region inside the visual field and further the size or shape of the region is equal or similar to the size or shape of the imaging range of the endoscope 121. In addition, for example, the visual field position estimation unit 191 may also be set to narrow down the candidates under the condition that a region having a higher temperature than the periphery is specified as a candidate for the region inside the visual field and further the temperature of the region is equal to or approximates the temperature of the imaging range of the endoscope 121 (that is, a predetermined temperature set as a temperature of a subject due to radiation light). By narrowing down the candidates in this manner, accuracy in specifying the region inside the visual field can be enhanced.

Note that a parameter used as a condition for narrowing down (a size, shape, temperature, or the like of the region inside the visual field of the endoscope 121) may be set in the visual field position estimation unit 191 in advance, can be appropriately set in the monitoring device 113, or may be appropriately supplied from the outside of the monitoring device 113 (for example, the endoscope 121, the CCU 111, the light source device 112, or the like). By making the setting of a parameter variable, the region inside the visual field 162 can be specified more accurately even when the setting of the endoscope 121 (for example, an angle of view of imaging, the type of radiation light, or the like) is variable.

In addition, conditions for narrowing down are arbitrary, and are not limited to the above-described examples. In addition, techniques for enhancing accuracy in specifying the region inside the visual field are also arbitrary, and are not limited to the above-described example.

When the region inside the visual field is specified based on the result of sensing, the visual field position estimation unit 191 estimates the position of the specified region inside the visual field, i.e., the position of the region inside the visual field in all regions including the region inside the visual field and the region outside the visual field (which may be the sensing region). In other words, the visual field position estimation unit 191 estimates the positional relation between the region inside the visual field and the region outside the visual field. That is, position comparison (matching) of the coordinates of the region inside the visual field and the coordinates of the region outside the visual field is performed.

Note that this "position comparison" may include not only position comparison of the coordinates but also matching (orienting) directions of the region inside the visual field and the region outside the visual field (directions of the coordinates). That is, the visual field position estimation unit 191 may be set to estimate the relation between the directions of the region inside the visual field and the region outside the visual field (i.e., matching of the directions of the coordinates of both regions).

Generally, the endoscope 121 and the monitoring sensor 125 can be installed in the inside of the body of the patient 151 in an arbitrary direction, and the top, bottom, left, and right (directions of the coordinates) of a captured image obtained by the endoscope 121 do not coincide with the top, bottom, left, and right (directions of the coordinates) of the result of sensing obtained by the monitoring sensor 125 at all times.

Thus, by matching not only the positions but also directions of the coordinates of the region inside the visual field and the region outside the visual field of the endoscope 121 for estimation of a position of the visual field, the visual field position estimation unit 191 can obtain the relative position (position or direction) of each location in the region outside the visual field to the region inside the visual field more accurately. Therefore, for example, the direction of the position of an abnormality occurring in the region outside the visual field can be notified of more accurately.

The visual field position estimation unit 191 obtains relative attitudes of the endoscope 121 and the monitoring sensor 125 (attitudes relative to each other) based on, for example, the result of sensing of the gyro sensor 172 and the result of sensing of the gyro sensor 182, and obtains the relation between the captured image and the results of sensing based on the relative attitudes (that is, estimates the relation between the directions of the region inside the visual field and the region outside the visual field).

The visual field position estimation unit 191 supplies information regarding the position of the region inside the visual field estimated as described above (also including the relation between the directions of the region inside the visual field and the region outside the visual field) to the notification information generation unit 193.

Note that methods for specifying the region inside the visual field or estimating the position thereof described above are arbitrary and are not limited to the above-described example. For example, the visual field position estimation unit 191 may specify the region inside the visual field or estimate a position thereof without using the results of sensing of the gyro sensor 172 and the gyro sensor 182.

For example, light from the endoscope 121 may be radiated on a subject (organ or the like) in a shape such as a triangle with which the direction (direction of the coordinates) of the endoscope 121 (region inside the visual field) can be identified, and the visual field position estimation unit 191 may be set to specify the shape in temperature distribution obtained by the monitoring sensor 125 and thus estimate the relation between the directions of the region inside the visual field and the region outside the visual field from the shape.

In addition, for example, the visual field position estimation unit 191 may be set to acquire information regarding a captured image obtained by the endoscope 121 from the CCU 111 and specify the region inside the visual field or estimate the position based on the foregoing information and information regarding a result of sensing supplied from the monitoring sensor 125. To be more specific, it may be possible, for example, to turn the result of sensing into an image, specify a region of the image which is the same as or similar to a captured image as the region inside the visual field, and estimate the position (including the direction) of the region.

The abnormality detection unit 192 detects occurrence of an abnormality in the region outside the visual field based on a result of sensing of a sensing region which includes at least a part of the region outside the visual field of the endoscope. For example, the abnormality detection unit 192 acquires information regarding a result of sensing performed by the thermo sensor 181 from the monitoring sensor 125, and based on this information, detects occurrence of an abnormality in the sensing region. Content of the abnormality detected by the abnormality detection unit 192 is arbitrary. The abnormality detection unit 192 supplies the information regarding the occurrence of the detected abnormality to the notification information generation unit 193. Note that the abnormality detection unit 192 may be set to further supply the information regarding the result of sensing to the notification information generation unit 193.

The notification information generation unit 193 generates notification information for performing notification regarding the abnormality detected by the abnormality detection unit 192. For example, the notification information generation unit 193 may be set to generate notification information for performing notification regarding detection of the abnormality by the abnormality detection unit 192 or notification information for performing notification regarding the position of the occurrence of the abnormality detected by the abnormality detection unit 192.

For example, the notification information generation unit 193 generates the notification information based on information supplied from the visual field position estimation unit 191 or the abnormality detection unit 192. The notification information generation unit 193, for example, may specify the position of the abnormality occurrence location as a relative position to one in the region inside the visual field of the endoscope 121 estimated by the visual field position estimation unit 191 and generate notification information for performing notification regarding the abnormality in a method according to the specified position of the abnormality occurrence location.

The notification information generation unit 193 supplies the generated notification information to the output control unit 194. Note that the notification information generation unit 193 may be set to further supply the information regarding the result of sensing to the output control unit 194.

The output control unit 194 controls output of information. For example, the output control unit 194 generates a display image (i.e., an image of the region inside the visual field) from a captured image supplied from the CCU 111, and supplies the display image to the output device 114 to display it. In addition, the output control unit 194, for example, supplies notification information (an image, a sound, or the like) supplied from the notification information generation unit 193 to the output device 114 to cause the information to be output. Note that the output control unit 194 may be set to further supply the information regarding the result of sensing (image, sound, or the like) supplied from the notification information generation unit 193 to the output device 114 to cause the information to be output.

A method for outputting information by the output control unit 194 is arbitrary, and is not limited to the above-described example. The output control unit 194, for example, may be set to supply an image of notification information supplied from the notification information generation unit 193 to the output device 114 by superimposing the image on a captured image supplied from the CCU 111 and to cause the image to be displayed. In addition, the output control unit 194 may be set to supply various kinds of information to a device other than the output device 114.

In the example of FIG. 3, the output device 114 has a monitor 201 and a speaker 202. The monitor 201 displays, for example, a display image (image of the region inside the visual field) supplied from the output control unit 194, an image of notification information, an image relating to a result of sensing, and the like. The speaker 202 outputs a sound of notification information supplied from the output control unit 194, a sound relating to a result of sensing, or the like.

A configuration of the output device 114 is arbitrary. For example, the monitor 201 or the speaker 202 may be omitted. In addition, the output device 114, for example, may include a plurality of monitors 201 or a plurality of speakers 202. Furthermore, the output device 114, for example, may include an output unit other than the monitor 201 and the speaker 202.

As described above, since the monitoring device 113 has the abnormality detection unit 192 and the notification information generation unit 193, an abnormality occurring in the region inside the visual field and the region outside the visual field of the endoscope can be ascertained more easily.

Note that the visual field position estimation unit 191 and the output control unit 194 may be omitted. In other words, by including the visual field position estimation unit 191, the monitoring device 113 can perform notification regarding an abnormality with various methods using information regarding the position of the region inside the visual field estimated by the visual field position estimation unit 191. In addition, by including the output control unit 194, the monitoring device 113 can output the notification information with various methods.

In addition, the endoscope 121 and the monitoring device 113 may be provided as one device. In this case, the endoscope 121 and the monitoring device 113 may be provided in one housing or in separate bodies. The monitoring sensor 125, the CCU 111, the light source device 112, and the output device 114 may each also be provided as one device together with the monitoring device 113 like the endoscope 121. Of course, multiple elements among the endoscope 121, the monitoring sensor 125, the CCU 111, the light source device 112, and the output device 114 may be set as one device together with the monitoring device 113. Furthermore, other devices may also be provided as one device together with the monitoring device 113.

<Abnormality Detection Unit>

FIG. 4 is a functional block diagram showing an example of a main function of the abnormality detection unit 192. In the example of FIG. 4, the abnormality detection unit 192 has a hemorrhage detection unit 211, a surgical instrument temperature abnormality detection unit 212, and an organ temperature abnormality detection unit 213.

The hemorrhage detection unit 211 detects occurrence of a hemorrhage as occurrence of an abnormality based on information regarding a result of sensing. For example, the hemorrhage detection unit 211 detects occurrence of a hemorrhage in a sensing region from temperature distribution of the sensing region obtained by the thermo sensor 181. To be more specific, the hemorrhage detection unit 211 detects that a hemorrhage has occurred and specifies the location of the occurrence in the result of sensing.

In an endoscopic surgery, blood in a blood vessel has a higher temperature than a surface of an organ (a surgical site or the periphery thereof) which is in contact with the air. That is, blood which has just flowed out has a higher temperature than the periphery. Then, the blood that has flowed out gradually spreads from the location of the hemorrhage to the periphery. For this reason, in the temperature distribution which is the result of sensing of the thermo sensor 181, points with higher temperatures than the periphery appear and a change in which the high temperature portions gradually spread to the periphery takes place. The hemorrhage detection unit 211 detects, for example, such a change from temperature distribution as occurrence of a hemorrhage, and specifies the location of such a point with high temperature as a location at which a hemorrhage has occurred. Of course, a method for detecting occurrence of a hemorrhage is arbitrary, and is not limited to the example.

Since the temperature of the blood that has flowed out gradually decreases immediately after a hemorrhage, the temperature of the location at which the hemorrhage occurred becomes higher than that of the blood which has flowed to the periphery. Thus, by detecting occurrence of the hemorrhage from the temperature distribution which is the result of sensing by the thermo sensor 181, the hemorrhage detection unit 211 can specify the location of the occurrence of a hemorrhage more accurately even when the location of the hemorrhage is concealed by the discharged blood.

Note that information that the hemorrhage detection unit 211 uses for detecting occurrence of a hemorrhage is arbitrary, and may be information other than temperature distribution. For example, the hemorrhage detection unit 211 may perform predetermined image analysis on a captured image to detect occurrence of a hemorrhage. That is, even when the monitoring sensor 125 has a sensor other than the thermo sensor 181 and thereby obtains a result of sensing other than temperature distribution, the hemorrhage detection unit 211 may detect occurrence of a hemorrhage based on the result of sensing obtained by the monitoring sensor 125. Note that when occurrence of a hemorrhage is not detected as occurrence of an abnormality, the hemorrhage detection unit 211 can be omitted.

The surgical instrument temperature abnormality detection unit 212 detects occurrence of a temperature abnormality of a surgical instrument as occurrence of abnormality based on information regarding a result of sensing. For example, the surgical instrument temperature abnormality detection unit 212 detects occurrence of a temperature abnormality of a surgical instrument positioned in a sensing region from temperature distribution of the sensing region obtained by the thermo sensor 181. To be more specific, the surgical instrument temperature abnormality detection unit 212 detects that a temperature abnormality has occurred in a surgical instrument and specifies the location of the occurrence in a result of sensing.

For example, when a temperature of the energy device 122 which is not being used in a task unnecessarily increases, there is concern that the energy device 122 has touched an organ and unintentionally damaged the organ. Particularly, since the region outside the visual field 163 is beyond the visual field of an operator, there is high concern of the energy device 122 being treated with insufficient caution and thus touching an organ.

Thus, the surgical instrument temperature abnormality detection unit 212 monitors temperatures of surgical instruments positioned in a sensing region and detects occurrence of a temperature abnormality. A method for detecting occurrence of a temperature abnormality is arbitrary. For example, it may be possible to detect a surgical instrument with a low temperature from temperature distribution and monitor whether the distal end thereof has a predetermined temperature or higher, or whether there is a part in a sensing region having a predetermined temperature or higher may simply be monitored.

Note that information that the surgical instrument temperature abnormality detection unit 212 uses for detecting occurrence of a temperature abnormality of a surgical instrument is arbitrary and may be information other than temperature distribution. That is, even when the monitoring sensor 125 has a sensor other than the thermo sensor 181 to obtain a result of sensing other than temperature distribution, the surgical instrument temperature abnormality detection unit 212 may detect occurrence of a temperature abnormality of a surgical instrument based on the result of sensing obtained by the monitoring sensor 125. Note that, when occurrence of a temperature abnormality of a surgical instrument is not detected as occurrence of an abnormality, the surgical instrument temperature abnormality detection unit 212 can be omitted.

The organ temperature abnormality detection unit 213 detects occurrence of a temperature abnormality of an organ as occurrence of abnormality based on information regarding a result of sensing. For example, the organ temperature abnormality detection unit 213 detects occurrence of a temperature abnormality of an organ positioned in a sensing region from temperature distribution of the sensing region obtained by the thermo sensor 181. To be more specific, the organ temperature abnormality detection unit 213 detects that a temperature abnormality has occurred in an organ and specifies the location of the occurrence in a result of sensing.

For example, when the energy device 122 touches an organ or the like, resulting in damage to the organ, the damaged part of the organ has a higher temperature than a peripheral part even if a hemorrhage does not occur. In addition, even when an operator is using the energy device 122 (when the operator intentionally touches an organ with the energy device 122), if the use (touch) is excessive, there is concern of the organ having a higher temperature than necessary or a part thereof with a high temperature widening further than necessary.

The organ temperature abnormality detection unit 213 detects occurrence of a temperature abnormality of an organ by monitoring a temperature of the organ. A method for detecting occurrence of a temperature abnormality is arbitrary. For example, whether there is a part in a sensing region having a predetermined temperature or higher may simply be monitored, and each organ may also be identified from temperature distribution or a positional relation between an organ and a surgical instrument may be considered. In addition, the type of an abnormality (for example, whether it is caused by a surgical instrument which has touched an organ, a change of a physical condition, or the like) may be further identified according to arbitrary information such as a temperature or an aspect of temperature distribution when it is detected as an abnormality.

Note that information that the organ temperature abnormality detection unit 213 uses for detecting occurrence of a temperature abnormality of an organ is arbitrary and may be information other than temperature distribution. That is, even when the monitoring sensor 125 has a sensor other than the thermo sensor 181 to obtain a result of sensing other than temperature distribution, the organ temperature abnormality detection unit 213 may detect occurrence of a temperature abnormality of an organ based on the result of sensing obtained by the monitoring sensor 125. Note that, when occurrence of a temperature abnormality of an organ is not detected as occurrence of an abnormality, the organ temperature abnormality detection unit 213 can be omitted.

The abnormality detection unit 192 supplies information regarding the detection result of each of the functional blocks to the notification information generation unit 193.

Note that a function realized by the abnormality detection unit 192 is arbitrary and is not limited to the example of FIG. 4. That is, the abnormality detection unit 192 may be set to have a functional block other than the functional blocks of the example of FIG. 4.

<Notification Information Generation Unit>

As described above, the notification information generation unit 193 generates notification information for performing notification regarding an abnormality. For example, as notification information for performing notification regarding an abnormality, the notification information generation unit 193 may be set to generate notification information for performing notification regarding detection of an abnormality by the abnormality detection unit 192.

FIG. 5 is a functional block diagram showing an example of a main function of the notification information generation unit 193. In the example of FIG. 5, the notification information generation unit 193 has an abnormality occurrence notification generation unit 221.

The abnormality occurrence notification generation unit 221 generates notification information for performing notification regarding detection of an abnormality by the abnormality detection unit 192 as the notification information for performing notification regarding an abnormality. For example, the abnormality occurrence notification generation unit 221 may be set to generate notification information for giving a notification that an abnormality has been detected. To be more specific, for example, the abnormality occurrence notification generation unit 221 may generate at least one of an image or a sound for giving a notification that the abnormality has occurred, as the notification information for performing notification regarding the occurrence of the abnormality. By performing such notification, a notified operator or the like can ascertain the fact that an abnormality has occurred more easily.

In addition, for example, the abnormality occurrence notification generation unit 221 may be set to generate notification information for performing notification regarding the content of the abnormality detected by the abnormality detection unit 192. To be more specific, the abnormality occurrence notification generation unit 221 may be set to generate, for example, at least one of an image and a sound for performing notification regarding the content of the abnormality as the notification information for performing notification regarding the content of an abnormality. The content of an abnormality is arbitrary and includes, for example, a hemorrhage, a temperature abnormality of a surgical instrument or an organ, or the like. By performing such notification, a notified operator or the like can ascertain the content of an abnormality more easily.

Note that when notification regarding detection of an abnormality or notification regarding the content of a detected abnormality described above is not performed, the abnormality occurrence notification generation unit 221 may be omitted from the notification information generation unit 193.

In addition, as such notification information for performing notification regarding an abnormality, the notification information generation unit 193 may be set to generate notification information for performing notification regarding a location of occurrence of an abnormality detected by the abnormality detection unit 192. At this time, the notification information generation unit 193 may be set to generate the notification information for performing notification regarding the location of the occurrence of the abnormality using a method decided based on the position of the abnormality occurrence location. For example, the notification information generation unit 193 may be set to generate the notification information for performing notification regarding the location of the occurrence of the abnormality using a method decided based on whether or not the position of the abnormality occurrence location is within the visual field of the endoscope 121.

For example, when the position of the abnormality occurrence location is within a region inside the visual field, the notification information generation unit 193 may be set to generate an image or a sound which indicates the location of the occurrence of the abnormality as notification information. In addition, when the position of the abnormality occurrence location is outside the region inside the visual field (in other words, within a region outside the visual field), for example, the notification information generation unit 193 may be set to generate an image or a sound which indicates the direction of the location of the occurrence of the abnormality as notification information.

In the example of FIG. 5, the notification information generation unit 193 further has an abnormality occurrence position specification unit 222, an abnormality occurrence location notification generation unit 223, and an abnormality occurrence direction notification generation unit 224.

The abnormality occurrence position specification unit 222 specifies the position of the abnormality occurrence location (within a sensing region) based on information supplied from the abnormality detection unit 192. For example, the abnormality occurrence position specification unit 222 may be further set to determine whether or not the specified position of the abnormality occurrence location is within the region inside the visual field of the endoscope 121.

Note that when the position of the abnormality occurrence location is specified, the abnormality occurrence position specification unit 222 may be set to specify the position of the abnormality occurrence location as the relative position to a position in the region inside the visual field of the endoscope 121. In this case, the abnormality occurrence position specification unit 222 may use a position estimated by the visual field position estimation unit 191 as the position of the region inside the visual field of the endoscope 121.

By specifying the position of the abnormality occurrence location as described above, the notification information generation unit 193 can generate notification information for performing notification using a method decided based on the position of the abnormality occurrence location.

The abnormality occurrence location notification generation unit 223 generates notification information for performing notification regarding the abnormality occurrence location when the position of the abnormality occurrence location specified by the abnormality occurrence position specification unit 222 is within the region of the visual field of the endoscope 121. To be more specific, for example, the abnormality occurrence location notification generation unit 223 may be set to generate an image which indicates the abnormality occurrence location as the notification information for performing notification regarding the abnormality occurrence location. The abnormality occurrence location notification generation unit 223 may be set to generate, for example, the image which indicates the abnormality occurrence location on an image of the region inside the visual field. In addition, for example, the abnormality occurrence location notification generation unit 223 may be set to generate a sound which indicates the abnormality occurrence location as the notification information for performing notification regarding the abnormality occurrence location.

By setting the notification information for performing notification regarding the abnormality occurrence location to be generated when the position of the abnormality occurrence location is within the region inside the visual field, the notification information generation unit 193 can cause an operator or the like who is notified of the notification information to ascertain the abnormality more easily when an abnormality has occurred within the region inside the visual field.

When the position of the abnormality occurrence location specified by the abnormality occurrence position specification unit 222 is outside the region inside the visual field (within the region outside the visual field) of the endoscope 121, the abnormality occurrence direction notification generation unit 224 generates notification information for performing notification regarding the direction of the abnormality occurrence location. To be more specific, for example, as the notification information for performing notification regarding the abnormality occurrence location, the abnormality occurrence direction notification generation unit 224 may be set to generate an image which indicates the direction of the abnormality occurrence location. The abnormality occurrence direction notification generation unit 224, for example, may be set to generate an image which indicates the direction of the abnormality occurrence location on an image of the region inside the visual field. In addition, as the notification information for performing notification regarding the abnormality occurrence location, for example, the abnormality occurrence direction notification generation unit 224 may be set to generate a sound which indicates the direction of the abnormality occurrence location.

By setting the notification information for performing notification regarding the direction of the abnormality occurrence location to be generated when the position of the abnormality occurrence location is within the region inside the visual field, the notification information generation unit 193 can generate the notification information to cause an operator or the like who is notified of the notification information to ascertain the abnormality more easily when an abnormality has occurred within the region inside the visual field.

Note that, when the position of an abnormality occurrence location is not specified, the abnormality occurrence position specification unit 222 can be omitted from the notification information generation unit 193. In addition, notification regarding an abnormality occurrence location is not performed, the abnormality occurrence location notification generation unit 223 can be omitted from the notification information generation unit 193. Furthermore, when notification regarding the direction of an abnormality occurrence location is not performed, the abnormality occurrence direction notification generation unit 224 can be omitted from the notification information generation unit 193.

<Flow of an Endoscope Control Process>

Next, processes executed in the endoscopic surgery support system 100 as described above will be described. With reference to the flowchart of FIG. 6, an example of the flow of an endoscope control process executed in the endoscopic surgery support system 100 will be described.

When the endoscope control process starts, the endoscope 121 drives the gyro sensor 172 and the monitoring sensor 125 drives the gyro sensor 182 in Step S101 to start sensing of each attitude.

In Step S102, the light source device 112 emits light to be radiated from the endoscope 121 (illumination light) to supply the light to the endoscope 121. Accordingly, light is radiated to the inner side of the angle of view (a subject) of imaging from the endoscope 121.

In Step S103, the imaging unit 171 of the endoscope 121 images an inside of the visual field (i.e., the region inside the visual field 162) of the endoscope 121.

In Step S104, the output control unit 194 acquires information regarding an image captured by the imaging unit 171 via the CCU 111 and supplies the information to the output device 114. The monitor 201 of the output device 114 displays the captured image as an endoscope in-visual-field image (an image of the inside of the visual field) based on the supplied information.

In Step S105, the monitoring device 113 monitors the inside of a sensing region of the monitoring sensor 125 (for example, the inner side of the visual field and the periphery of the visual field of the endoscope 121).

In Step S106, the monitoring device 113 determines whether the endoscope control process is to be ended. When the process is determined not to be ended, the process returns to Step S101, and execution of the step and succeeding steps is repeated. When the endoscope control process is determined to be ended in Step S106, the endoscope control process ends.

<Flow of a Monitoring Process>

Next, an example of the flow of the monitoring process executed in Step S105 of FIG. 6 will be described with reference to the flowchart of FIG. 7. When the monitoring process starts, the visual field position estimation unit 191 estimates the position of the visual field of the endoscope (the position of the region inside the visual field of the endoscope 121) in Step S121 based on information regarding a result of sensing or the like.

In Step S122, the monitoring device 113 controls the monitoring sensor 125 (thermo sensor 181) to perform sensing of the sensing region (targeting, for example, the inside and the periphery of the visual field of the endoscope 121). The thermo sensor 181 of the monitoring sensor 125 performs sensing of the sensing region (targeting, for example, the inside and the periphery of the visual field of the endoscope 121) under the control.

In Step S123, the abnormality detection unit 192 detects the occurrence of an abnormality based on information regarding a result of the sensing obtained from the process of Step S122.

In Step S124, the notification information generation unit 193 determines whether or not the abnormality has occurred based on the process result of Step S123. When it is determined that the occurrence of the abnormality has been detected (in other words, the abnormality has occurred), the process proceeds to Step S125.

In Step S125, the notification information generation unit 193 generates notification information for performing notification regarding the occurrence of the abnormality. In Step S126, the output control unit 194 supplies the notification information generated in Step S125 to the output device 114 to cause the information to be output.

The output device 114 outputs the supplied notification information. When the process of Step S126 ends, the process proceeds to Step S127. In addition, when it is determined that the occurrence of the abnormality has not been detected (in other words, the abnormality has not occurred) in Step S124, the process proceeds to Step S127.

In Step S127, the monitoring device 113 determines whether or not monitoring is to be ended. When monitoring is determined not to be ended, the process returns to Step S121, and execution of the step and succeeding steps is repeated.

When monitoring is determined to be ended in Step S127, the monitoring process ends, and the process returns to the process of FIG. 6.

<Flow of an Abnormality Detection Process>

Next, an example of the flow of the abnormality detection process executed in Step S123 of FIG. 7 will be described with reference to the flowchart of FIG. 8.

When the abnormality detection process starts, the hemorrhage detection unit 211 detects occurrence of a hemorrhage based on the result of sensing of the monitoring sensor 125 (thermo sensor 181) in Step S141.

In Step S142, the surgical instrument temperature abnormality detection unit 212 detects a temperature abnormality of a surgical instrument based on the result of sensing of the monitoring sensor 125 (thermo sensor 181).

In Step S143, the organ temperature abnormality detection unit 213 detects a temperature abnormality of an organ based on the result of sensing of the monitoring sensor 125 (thermo sensor 181).

When detection of an abnormality based on each parameter of the monitoring target ends, the abnormality detection process ends, and the process returns to the process of FIG. 7.

<Flow of a Notification Information Generation Process>

Next, an example of the flow of the notification information generation process executed in Step S125 of FIG. 7 will be described with reference to the flowchart of FIG. 9.

When the notification information generation process starts, the abnormality occurrence notification generation unit 221 of the notification information generation unit 193 generates an abnormality occurrence notification which is notification information for performing notification regarding detection of the abnormality by the abnormality detection unit 192 (giving a notification that the abnormality has been detected) in Step S161.

In Step S162, the abnormality occurrence position specification unit 222 specifies a relative position of the abnormality occurrence location to the region inside the visual field of the endoscope 121.

In Step S163, the abnormality occurrence position specification unit 222 determines whether or not the position of the abnormality occurrence location specified in Step S162 is within the region inside the visual field of the endoscope 121. When the position of the abnormality occurrence location is determined to be within the region inside the visual field 162, the process proceeds to Step S164.

In Step S164, the abnormality occurrence location notification generation unit 223 generates an abnormality occurrence location notification which is notification information for performing notification regarding the abnormality occurrence location. When the abnormality occurrence location notification is generated, the notification information generation process ends, and the process returns to the process of FIG. 7.

In addition, when the position of the abnormality occurrence location is determined to be within the region outside the visual field of the endoscope 121 in Step S163 of FIG. 9, the process proceeds to Step S165.

In Step S165, the abnormality occurrence direction notification generation unit 224 generates an abnormality occurrence direction notification which is notification information for performing notification regarding the direction of the abnormality occurrence location. When the abnormality occurrence direction notification is generated, the notification information generation process ends, and the process returns to the process of FIG. 7.

By executing the processes described above, the monitoring device 113 can ascertain the abnormality occurring in the region inside the visual field or outside the visual field of the endoscope more easily.

<Example of Output of Notification Information>

Next, FIG. 10 is a diagram for describing an example of a display image displayed on, for example, the monitor 201 of the output device 114. As illustrated in FIG. 10, an endoscope in-visual-field image 230 generated from an image captured by the imaging unit 171 of the endoscope 121 is displayed on the monitor 201. This endoscope in-visual-field image 230 is a captured image of the region inside the visual field of the endoscope 121, displaying a lesion 231 which is a surgical site, and the periphery.

In the example of FIG. 10A, a hemorrhage has occurred near the lesion 231 (i.e., within the region inside the visual field) and accumulation of blood 232 has formed.

In addition, an abnormality occurrence notification image 233 which is an image of an abnormality occurrence notification generated by the abnormality occurrence notification generation unit 221 is displayed on the upper right side of the screen, superimposed on the endoscope in-visual-field image 230. In the example of FIG. 10A, a message "warning" which is a notification that an abnormality has been detected is displayed as the abnormality occurrence notification image 233. Through such a notification, the operator or the like who receives the notification can more easily ascertain that the abnormality has been detected.

In addition, in the example of FIG. 10A, the message "hemorrhage has occurred" which is a notification regarding the content of the abnormality is displayed as the abnormality occurrence notification image 233. Through the notification, the operator or the like who receives the notification can also ascertain the content of the abnormality as well as the occurrence of the abnormality more easily.

Of course, only the notification that the abnormality has been detected may be given by only displaying the message "warning." In addition, only the display of the message "hemorrhage has occurred" may be set to function as both the notification regarding the occurrence of the abnormality and the notification regarding the content of the abnormality.

Furthermore, the abnormality occurrence notification image 233 may be set to flicker, move, or transform. Through such a setting, the operator or the like who is to be notified can pay more attention to the notification.

In addition, the abnormality occurrence notification image 233 described above may be displayed on the monitor 201 and a sound such as an alarm for giving the notification that the abnormality has occurred may be output from the speaker 202. With such a setting, the operator or the like who is to be notified can pay more attention to the notification. Furthermore, a sound for giving the notification regarding the content of the abnormality may also be set to be output. With the setting, the operator or the like who receives the notification can ascertain the content of the abnormality more easily.

In addition, an abnormality occurrence location notification image 234 which is an image of the abnormality occurrence location notification generated by the abnormality occurrence location notification generation unit 223 is displayed over the endoscope in-visual-field image 230. In the example of FIG. 10A, a point which indicates that the position thereof is the abnormality occurrence location is displayed at the location as the abnormality occurrence location notification image 234. With the display, the operator or the like who receives the notification can ascertain the abnormality occurrence location within the region inside the visual field more easily and accurately.

Of course, the abnormality occurrence location notification image 234 may be set to flicker, move, or transform. With such a setting, the operator or the like who is to be notified can pay more attention to the notification.

In addition, the abnormality occurrence location notification image 234 may be displayed on the monitor 201 and a sound for giving the notification regarding the abnormality occurrence location may also be output from the speaker 202. With such a setting, the operator or the like who receives the notification can ascertain the abnormality occurrence location within the visual field more easily and accurately.

Note that the design of the abnormality occurrence location notification image 234 is arbitrary and may be something other than a point. In addition, a method for indicating the position of the abnormality occurrence location in the abnormality occurrence location notification image 234 is arbitrary, and the abnormality occurrence location notification image 234 may be displayed in a location other than the abnormality occurrence location.

In the example of FIG. 10B, a temperature abnormality of an organ has occurred within the region outside the visual field of the endoscope 121.

In addition, in the example of FIG. 10B, the message "warning" which is a notification that an abnormality has occurred and the message "organ temperature abnormality has occurred" which is a notification regarding the content of the abnormality are displayed as the abnormality occurrence notification image 233 on the upper right side of the screen, being superimposed on the endoscope in-visual-field image 230. With the display, the operator or the like who receives the notifications can ascertain the occurrence and content of the abnormality more easily.

In addition, an abnormality occurrence direction notification image 235 which is an image of an abnormality occurrence direction notification generated by the abnormality occurrence direction notification generation unit 224 is displayed over the endoscope in-visual-field image 230. In the example of FIG. 10B, an arrow which indicates the direction in which the abnormality has occurred is displayed as the abnormality occurrence direction notification image 235. With the display, the operator or the like who receives the notification can ascertain the direction of the abnormality occurrence location within the region outside the visual field more easily and accurately.

Of course, the abnormality occurrence direction notification image 235 may be set to flicker, move, or transform. With such a setting, the operator or the like who is to be notified can pay more attention to the notification.

In addition, the abnormality occurrence direction notification image 235 may be displayed on the monitor 201 and a sound for giving the notification regarding the direction of the abnormality occurrence location may also be output from the speaker 202. With such a setting, the operator or the like who receives the notification can ascertain the direction of the abnormality occurrence location outside the visual field more easily and accurately.

Note that the design of the abnormality occurrence direction notification image 235 is arbitrary and may be a shape other than an arrow, for example, a triangle or the like. In addition, a display position of the abnormality occurrence direction notification image 235 is arbitrary. For example, a display position of the abnormality occurrence direction notification image 235 may change according to the direction of the occurrence location of an abnormality.

As described above, by outputting the abnormality occurrence notification, abnormality occurrence location notification, abnormality occurrence direction notification, and the like, the operator or the like who receives the notifications can be notified by presenting the endoscope in-visual-field image 230 (without changing the size of the image). Accordingly, notification can be performed while obstruction of an operative field is suppressed. Therefore, the operator can ascertain an abnormality which occurs in the region inside or outside the visual field of the endoscope more easily while performing a task.

2. Second Embodiment

<Example of a Main Configuration of a Monitoring Device, Etc.>

The content of an abnormality is arbitrary and is not limited to the above examples. For example, contact of a surgical instrument with an organ may be detected. In such a case, the contact may be detected from their positional relation by, for example, obtaining depth information of the surgical instrument or the organ from a stereoscopic camera image or the like.

FIG. 11 is a block diagram showing another example of the main configuration of the monitoring device 113 and the like which performs such detection. In this case, the monitoring sensor 125 further has a stereoscopic camera 241. The configuration other than the camera is the same as that of FIG. 3.

The stereoscopic camera 241 includes a plurality of image sensors, images the inside of a sensing region (for example, the region inside or outside the visual field), and thereby obtains a stereoscopic image of the sensing region. A stereoscopic image is a pair of captured images obtained by imaging substantially the same subject from different positions. That is, a stereoscopic image is constituted with two captured images having parallax. Such a stereoscopic image is used as, for example, an image for stereoscopic view. The captured images constituting the stereoscopic image may be a captured image obtained from the image sensors, or a virtual captured image generated from captured images obtained from the image sensors.

Since the stereoscopic image is used for detecting occurrence of an abnormality, the image does not have to be as highly accurate (have high resolution) as the imaging unit 171 of the endoscope 121. For this reason, the sensing range of the stereoscopic camera 241 can be easily set to a wider range than the imaging range of the imaging unit 171 by, for example, using a wide-angle lens or the like.

Information regarding a stereoscopic image obtained by the stereoscopic camera 241 is supplied to the monitoring device 113 through communication between the monitoring sensor 125 and the monitoring device 113.

The abnormality detection unit 192 of the monitoring device 113 detects occurrence of an abnormality based on information regarding the result of sensing of the thermo sensor 181 and the information regarding the stereoscopic image.

<Abnormality Detection Unit>

FIG. 12 is a functional block diagram showing another example of the main function of the abnormality detection unit 192. In the example of FIG. 12, the abnormality detection unit 192 further has a contact detection unit 251 in addition to the hemorrhage detection unit 211 to the organ temperature abnormality detection unit 213 in the example of FIG. 4.

The contact detection unit 251 detects occurrence of contact a surgical instrument with an organ as occurrence of an abnormality. For example, the contact detection unit 251 detects occurrence of contact a surgical instrument with an organ based on temperature distribution of a sensing region (for example, the region inside or outside the visual field) obtained by the thermo sensor 181 and an image for stereoscopic view (stereoscopic image) of the sensing region.

For example, the contact detection unit 251 specifies a surgical instrument and an organ using the temperature distribution, further obtains depth information of the surgical instrument and the organ based on the stereoscopic image, sets the range of sensing as a three-dimensional space, specifies the position of the surgical instrument and the organ in the three-dimensional space, and then detects contact of the surgical instrument with the organ. By using not only the temperature distribution but also the stereoscopic image, the contact detection unit 251 can detect contact of the surgical instrument with the organ more accurately.

The contact detection unit 251 detects that contact of a surgical instrument with an organ has occurred and specifies the location of the occurrence in the result of sensing.

<Flow of an Abnormality Detection Process>

An endoscope control process, a monitoring process, a notification information generation process, and the like of this case are executed in the same manner as those of the first embodiment. An example of the flow of the abnormality detection process of this case will be described with reference to the flowchart of FIG. 13.

In the abnormality detection process of this case, the processes of Steps S201 to S203 of FIG. 13 are executed the same as those of Steps S141 to S143 of FIG. 8.

In Step S204, the contact detection unit 251 detects contact of a surgical instrument with an organ based on the result of sensing of the monitoring sensor 125 (the thermo sensor 181 and the stereoscopic camera 241).

When detection of an abnormality based on each parameter of the monitoring target ends, the abnormality detection process ends, and the process returns to the process of FIG. 7.

By performing the abnormality detection process as described above, a stereoscopic image of a sensing region can be imaged by the monitoring sensor 125 and contact of the surgical instrument with the organ can be detected using the stereoscopic image. Accordingly, the abnormality detection unit 192 can detect the abnormality (contact of the surgical instrument with the organ) occurring in the region inside or outside the visual field of the endoscope more accurately.

3. Third Embodiment

<Example of a Main Configuration of a Monitoring Device, Etc.>

A notification regarding occurrence of an abnormality may be given to a person other than an operator who performs a task. For example, a supervisor who monitors occurrence of an abnormality as well as an operator may be set to use the endoscopic surgery support system 100 as a user to be notified of occurrence of an abnormality by the endoscopic surgery support system 100. Of course, the notification may be given to both the operator and the supervisor. In addition, in such a case, a notification method for the operator may be different from a notification method for the supervisor.

<Example of a Main Configuration of the Monitoring Device, Etc.>

FIG. 14 is a block diagram showing still another example of the main configuration of the monitoring device 113 and the like. In this case, the notification information generation unit 193 generates operator-dedicated notification information which is notification information for an operator or the like and supervisor-dedicated notification information which is notification information for a supervisor. In addition, in this case, an operator-dedicated output device 301 and a supervisor-dedicated output device 302 are provided in place of the output device 114.

The operator-dedicated output device 301 is a device which outputs information such as an image, a sound, or the like to the operator or the like, like the output device 114. For example, the operator-dedicated output device 301 outputs operator-dedicated notification information which is notification information for the operator or the like generated by the notification information generation unit 193. In the example of FIG. 14, the operator-dedicated output device 301 has a monitor 311 which displays (operator-dedicated) images to be presented to the operator or the like and a speaker 312 which outputs (operator-dedicated) sounds to be presented to the operator or the like.

For example, this monitor 311 may be set to display the operator-dedicated notification information. In addition, for example, the monitor 311 may be set to further display an image of the region inside the visual field of the endoscope 121. Furthermore, for example, the monitor 311 may be set to further display an image regarding an (operator-dedicated) result of sensing to be presented to the operator or the like.

In addition, for example, the speaker 312 may be set to output sounds of the operator-dedicated notification information. Furthermore, for example, the speaker 312 may be set to further output sounds regarding an (operator-dedicated) result of sensing to be presented to the operator or the like.

Of course, a configuration of the operator-dedicated output device 301 is arbitrary. For example, the monitor 311 or the speaker 312 may be omitted. In addition, for example, the operator-dedicated output device 301 may have a plurality of monitors 311 or a plurality of speakers 312. Furthermore, for example, the operator-dedicated output device 301 may include an output device other than the monitor 311 and the speaker 312.

The supervisor-dedicated output device 302 is a device which outputs information such as an image, a sound, or the like to the supervisor or the like, like the output device 114. For example, the supervisor-dedicated output device 302 outputs supervisor-dedicated notification information which is notification information for the supervisor or the like generated by the notification information generation unit 193. In the example of FIG. 14, the supervisor-dedicated output device 302 has a monitor 321 which displays (supervisor-dedicated) images to be presented to the supervisor or the like and a speaker 322 which outputs (supervisor-dedicated) sounds to be presented to the supervisor or the like.

For example, this monitor 321 may be set to display the supervisor-dedicated notification information. In addition, for example, the monitor 321 may be set to further display an image of the region inside the visual field of the endoscope 121. Furthermore, for example, the monitor 321 may be set to further display an image regarding an (supervisor-dedicated) result of sensing to be presented to the supervisor or the like.

In addition, for example, the speaker 322 may be set to output sounds of the supervisor-dedicated notification information. Furthermore, for example, the speaker 322 may be set to further output sounds regarding an (supervisor-dedicated) result of sensing to be presented to the supervisor or the like.

Of course, a configuration of the supervisor-dedicated output device 302 is arbitrary. For example, the monitor 321 or the speaker 322 may be omitted. In addition, for example, the supervisor-dedicated output device 302 may have a plurality of monitors 321 or a plurality of speakers 322. Furthermore, for example, the supervisor-dedicated output device 302 may include an output device other than the monitor 321 and the speaker 322.

In addition, in FIG. 14, the output control unit 194 of the monitoring device 113 outputs information of an image, a sound, or the like to both the operator-dedicated output device 301 and the supervisor-dedicated output device 302. For example, the output control unit 194 may supply an image of the region inside the visual field of the endoscope 121 to the operator-dedicated output device 301 and cause the monitor 311 to display the image. In addition, for example, the output control unit 194 may also supply the image of the region inside the visual field to the supervisor-dedicated output device 302 and cause the monitor 321 to display the image. Furthermore, for example, the output control unit 194 may supply notification information for performing notification regarding a result of sensing to the supervisor-dedicated output device 302 and cause the monitor 321 to display an image thereof or the speaker 322 to output a sound thereof.

<Notification Information Generation Unit>

FIG. 15 is a functional block diagram showing another example of the main function of the notification information generation unit 193 of this case. In this case, the notification information generation unit 193 generates the operator-dedicated notification information which is notification information for an operator and the supervisor-dedicated notification information which is notification information for notifying a supervisor other than the operator who performs a task within the region inside the visual field of the endoscope 121 of an abnormality detected by the abnormality detection unit 192. This supervisor-dedicated notification information may be notification information for performing notification regarding an abnormality using an image or a sound or both different from those of the operator-dedicated notification information.

In the example of FIG. 15, the notification information generation unit 193 has the abnormality occurrence notification generation unit 221 to the abnormality occurrence direction notification generation unit 224 and a sensing result notification generation unit 331.

The abnormality occurrence notification generation unit 221 generates at least any one of an image and a sound for notifying a supervisor or the like of the fact that an abnormality has been detected as the supervisor-dedicated notification information. In addition, the abnormality occurrence notification generation unit 221 generates at least any one of an image and a sound for notifying the supervisor or the like of the content of the abnormality as the supervisor-dedicated notification information. Furthermore, the abnormality occurrence notification generation unit 221 generates at least any one of an image and a sound for notifying an operator or the like of the fact that the abnormality has been detected as the operator-dedicated notification information. In addition, the abnormality occurrence notification generation unit 221 generates at least any one of an image and a sound for notifying the operator or the like of the content of the abnormality as the operator-dedicated notification information.

The abnormality occurrence position specification unit 222 performs the same process as in FIG. 5.

The abnormality occurrence location notification generation unit 223 generates at least any one of an image and a sound for notifying the supervisor or the like of the abnormality occurrence location as the supervisor-dedicated notification information. In addition, the abnormality occurrence location notification generation unit 223 generates at least any one of an image and a sound for notifying the operator or the like of the abnormality occurrence location as the operator-dedicated notification information.

Note that it is not necessary to display an image of the region inside the visual field 162 to the supervisor or the like who does not perform a task. In other words, presenting an image of the region outside the visual field to the supervisor seldom obstructs the task of the operator. Thus, an image of a sensing region may be set to be presented to the supervisor or the like. In addition, the supervisor or the like may be set to be notified of the abnormality occurrence location regardless of the position of the location and not to be notified of the direction of the abnormality occurrence location.

In this case, the abnormality occurrence direction notification generation unit 224 generates notification information for performing notification regarding the direction of the abnormality occurrence location only as the operator-dedicated notification information, like in the case of FIG. 5.

The sensing result notification generation unit 331 generates a sensing result notification which is notification information for notifying the supervisor or the like of the result of sensing. For example, the sensing result notification generation unit 331 generates at least any one of an image and a sound for performing notification regarding the result of sensing as the sensing result notification.

Note that, as in the case of FIG. 5, the abnormality occurrence notification generation unit 221 to the abnormality occurrence direction notification generation unit 224 can be appropriately omitted. In addition, when the supervisor or the like is not notified of the result of sensing, the sensing result notification generation unit 331 can be omitted from the notification information generation unit 193.

Note that notification to the operator may be omitted. In such a case, for example, the operator-dedicated output device 301 can be omitted. In addition, in this case, for example, the output control unit 194 only outputs information to the supervisor-dedicated output device 302. Furthermore, for example, the abnormality occurrence notification generation unit 221 and the abnormality occurrence location notification generation unit 223 of the notification information generation unit 193 can omit generation of the operator-dedicated notification information. In addition, for example, the abnormality occurrence direction notification generation unit 224 can also be omitted.

<Flow of an Endoscope Control Process>

Next, an example of the flow of an endoscope control process of this case will be described with reference to the flowchart of FIG. 16. In the endoscope control process of this case, the processes of Steps S301 to S303 of FIG. 16 are executed the same as those of Steps S101 to S103 of FIG. 6.

In Step S304, the output control unit 194 acquires information regarding an image captured by the imaging unit 171 via the CCU 111, and supplies the information to the operator-dedicated output device 301. The monitor 311 of the operator-dedicated output device 301 displays (to the operator or the like) the captured image as an endoscope in-visual-field image (an image of the inside the visual field) based on the supplied information.

In Step S305, the monitoring device 113 monitors the inside of a sensing region (for example, the inner side of the visual field and the periphery of the visual field of the endoscope 121).

In Step S306, the monitoring device 113 determines whether the endoscope control process is to be ended. When the process is determined not to be ended, the process returns to Step S301, and execution of the step and succeeding steps is repeated. When the endoscope control process is determined to be ended in Step S306, the endoscope control process ends.

<Flow of a Monitoring Process>

Next, an example of the flow of the monitoring process of this case executed in Step S305 of FIG. 16 will be described with reference to the flowchart of FIG. 17. In the monitoring process of this case, the processes of Steps S321 and S322 of FIG. 17 are executed the same as those of Steps S121 to S122 of FIG. 7.

In Step S323, the sensing result notification generation unit 331 generates a sensing result notification which is notification information for performing notification regarding the result of sensing performed in Step S322 (for example, an image, a sound, or the like which indicates temperature distribution of a sensing region which is the result of sensing obtained by the thermo sensor 181).

In Step S324, the output control unit 194 supplies information regarding an image captured by the imaging unit 171 to the supervisor-dedicated output device 302. The monitor 321 of the supervisor-dedicated output device 302 displays (to the supervisor or the like) the captured image as an endoscope in-visual-field image (an image of the inside the visual field) based on the supplied information.

In addition, in Step S325, the output control unit 194 supplies the sensing result notification generated in Step S323 to the supervisor-dedicated output device 302. The supervisor-dedicated output device 302 outputs the supplied sensing result notification (to the supervisor or the like). For example, the monitor 321 may display an image of the sensing result notification. In addition, for example, the speaker 322 may output a sound of the sensing result notification.

The processes of Steps S326 to S330 of FIG. 17 are executed the same as those of Steps S123 to S127 of FIG. 7. Details of the processes of Steps S328 and S329, however, will be described below.

When the monitoring is determined to be ended in Step S330, the process returns to Step S321, and execution of the step and succeeding steps is repeated. When the monitoring is determined not to be ended in Step S330, the monitoring process ends, and the process returns to the process of FIG. 16.

<Flow of a Notification Information Generation Process>

Next, an example of the flow of the notification information generation process of this case executed in Step S328 of FIG. 17 will be described with reference to the flowchart of FIG. 18.

When the notification information generation process of this case is started, the abnormality occurrence notification generation unit 221 of the notification information generation unit 193 generates a supervisor-dedicated abnormality occurrence notification in Step S351.

In Step S352, the abnormality occurrence location notification generation unit 223 generates a supervisor-dedicated abnormality occurrence location notification.

In Step S353, the abnormality occurrence notification generation unit 221 generates an operator-dedicated abnormality occurrence notification.

In Step S354, the abnormality occurrence position specification unit 222 specifies a relative position of the abnormality occurrence location to the region inside the visual field of the endoscope 121.

In Step S355, the abnormality occurrence position specification unit 222 determines whether or not the position of the abnormality occurrence location specified in Step S354 is within the region inside the visual field of the endoscope 121. When the position of the abnormality occurrence location is determined to be within the region inside the visual field, the process proceeds to Step S356.

In Step S356, the abnormality occurrence location notification generation unit 223 generates an operator-dedicated abnormality occurrence location notification. After the operator-dedicated abnormality occurrence location notification is generated, the notification information generation process ends, and the process returns to the process of FIG. 17.

In addition, when the position of the abnormality occurrence location is determined to be outside the region inside the visual field (i.e., within the region outside the visual field) of the endoscope 121 in Step S355 of FIG. 18, the process proceeds to Step S357.

In Step S357, the abnormality occurrence direction notification generation unit 224 generates an operator-dedicated abnormality occurrence direction notification. After the operator-dedicated abnormality occurrence direction notification is generated, the notification information generation process ends, and the process returns to the process of FIG. 17.

<Flow of a Notification Information Output Process>

Next, an example of the flow of a notification information output process of this case executed in Step S329 of FIG. 17 will be described with reference to the flowchart of FIG. 19.

When the notification information output process is started, the output control unit 194 acquires the supervisor-dedicated abnormality occurrence notification from the notification information generation unit 193 and supplies the notification to the supervisor-dedicated output device 302 in Step S371. The supervisor-dedicated output device 302 outputs the supplied supervisor-dedicated abnormality occurrence notification (to the supervisor or the like).

In Step S372, the output control unit 194 acquires the supervisor-dedicated abnormality occurrence location notification from the notification information generation unit 193 and supplies the notification to the supervisor-dedicated output device 302. The supervisor-dedicated output device 302 outputs the supplied supervisor-dedicated abnormality occurrence location notification (to the supervisor or the like).

In Step S373, the output control unit 194 acquires the operator-dedicated abnormality occurrence notification from the notification information generation unit 193 and supplies the notification to the operator-dedicated output device 301. The operator-dedicated output device 301 outputs the supplied operator-dedicated abnormality occurrence notification (to the operator or the like).

In Step S374, the output control unit 194 determines whether or not the abnormality occurrence position is within the region inside the visual field of the endoscope 121 based on the information supplied from the notification information generation unit 193. When the position is determined to be within the region inside the visual field, the process proceeds to Step S375.

In Step S375, the output control unit 194 acquires the operator-dedicated abnormality occurrence location notification from the notification information generation unit 193 and supplies the notification to the operator-dedicated output device 301. The operator-dedicated output device 301 outputs the supplied operator-dedicated abnormality occurrence location notification (to the operator or the like).

When the process of Step S375 ends, the notification information output process ends, and the process returns to the process of FIG. 17. When the abnormality occurrence position is determined to be within the region inside the visual field of the endoscope 121 in Step S374 of FIG. 19, the process proceeds to Step S376.

In Step S376, the output control unit 194 acquires the operator-dedicated abnormality occurrence direction notification from the notification information generation unit 193 and supplies the notification to the operator-dedicated output device 301. The operator-dedicated output device 301 outputs the supplied operator-dedicated abnormality occurrence direction notification (to the operator or the like).

By executing the processes described above, the monitoring device 113 can cause the supervisor or the like to ascertain the abnormality occurring in the region inside the visual field or outside the visual field of the endoscope more easily.

<Example of Output of Notification Information>

A method for displaying operator-dedicated information may be set to be the same as in the first embodiment. FIG. 20 is a diagram for describing an example of a display image (image for monitoring) displayed on the monitor 321 of the supervisor-dedicated output device 302. In the display image of the example of FIG. 20, an entire sensing region is displayed. This sensing region includes an entire region inside the visual field and part of a region outside the visual field of the endoscope. The region inside the visual field 342 is a region which includes a lesion 341 and the periphery thereof, and the region outside the visual field 343 is a region around the region inside the visual field 342.

With respect to the above-described sensing region, for example, a sensing result of the entire sensing region may be made into an image like, for example, a dotted-line frame 351 and the image may be displayed on the monitor 321 of the supervisor-dedicated output device 302 as an image for sensing result notification. Consequently, the sensing result of the entire sensing region is shown as an image in this case.

In addition, the sensing result of the entire region inside the visual field 342 and part of the region outside the visual field 343 may be made into an image like, for example, a dotted-line frame 352, and the image may be displayed on the monitor 321 of the supervisor-dedicated output device 302 as an image for sensing result notification. Consequently, the sensing result of the part of the sensing region including the entire region inside the visual field 342 is shown as an image in this case.

Furthermore, a sensing result of a partial region including an abnormality occurrence location and the periphery thereof may be made into an image like, for example, a dotted-line frame 353, and the image may be displayed on the monitor 321 of the supervisor-dedicated output device 302 as an image for sensing result notification. Consequently, the sensing result of the partial sensing region including a part of the region inside the visual field 342 which is independent from the region inside the visual field 342 and the region outside the visual field 343 is shown as an image in this case.

Note that the number of displayed images for sensing result notification may be plural. For example, a plurality of regions within a sensing range may be displayed as images for sensing result notification.

In addition, (the size, position, shape, number, and the like of) the range of an image for sensing result notification may be variable. For example, the range of an image for sensing result notification may be set to the dotted-line frame 351, the dotted-line frame 352, or the dotted-line frame 353.

In such a case, the range of an image for sensing result notification may be appropriately changed according to a situation or an instruction of a user or the like.

As shown in FIG. 20, an abnormality occurrence notification image 361 is displayed in the periphery of the abnormality (hemorrhage) occurrence location, and an abnormality occurrence location notification image 362 is displayed at the abnormality (hemorrhage) occurrence location. A display position and design of the abnormality occurrence notification image 361 and the abnormality occurrence location notification image 362 are arbitrary.

Of course, a sound pertaining to the abnormality occurrence notification, abnormality occurrence location notification, or the like may be output along with the display. In addition, a supervisor-dedicated image and an operator-dedicated image may be the same.

By performing various kinds of notification to the supervisor or the like as described above, it is possible to help the supervisor or the like in addition to the operator ascertain an abnormality occurring within and in the periphery of the visual field of an endoscope more easily.

4. Fourth Embodiment

<Sensing with an Endoscope>

Sensing for detecting occurrence of an abnormality can be performed by an arbitrary sensor. For example, such sensing may be performed using the imaging unit 171 of the endoscope 121.

For example, when the aspect ratio of a captured image 401 obtained by the imaging unit 171 is set to 4:3 and the aspect ratio of a display image displayed on the monitor 201 is set to 16:9, the monitor 201 can display only a partial region of the captured image 401 (for example, a region 402) as shown in FIG. 21A. In other words, a region 403 and a region 404 are not displayed.

Thus, the entire captured image 401 is set to a sensing region and the inside of a circle 405 which comes under the captured image 401 is set as a light radiation region as shown in FIG. 21A. In this case, the region inside the circle 405 of the region 402 which can be displayed on the monitor 201 is a region inside the visual field and the other regions (i.e., the regions 403 and 404 expressed with hatching and the region outside the circle 405 which is included in the region 402) are regions outside the visual field.

In addition, the entire captured image 401 may be set to a sensing region and the inside of the circle 405 including the entire region 402 which can be displayed on the monitor 201 may be set as a light radiation region as shown in FIG. 21B. In this case, the entire region 402 is set as a region inside the visual field and other regions (i.e., the regions 403 and 404 expressed with hatching) are set as regions outside the visual field.

Consequently, the entire region inside the visual field and the part of the regions outside the visual field of the endoscope 121 are included in the sensing region in this case. Thus, with the settings, the imaging unit 171 can not only generate an image inside the visual field but can also realize sensing of the inside and the periphery of the visual field of the endoscope 121.

In this case, the monitoring sensor 125 can be omitted.

In addition, the imaging unit 171 may be constituted by a plurality of image sensors. For example, the imaging unit 171 is constituted by three image sensors to image captured images 401-1 to 401-3 as in FIG. 22A. In addition, the inside of the circle 405 including the entire region 402 which can be displayed on the monitor 201 may be set as a light radiation region as in the case of FIG. 21B. In this case, the entire region 402 is set as a region inside the visual field, and regions of the regions 403 and 404 which are included inside the circle 405 and regions of the captured images 401-2 and 401-3 which are included inside the circle 405 are set as regions outside the visual field. Consequently, the regions outside the visual field are widened more than in the case of FIG. 21B (a wider range can be sensed).

Note that all regions inside the circle 405 may be set as the sensing region by appropriately disposing a plurality of image sensors.

In addition, an aspect ratio and size of the captured image 401 and the region 402 which can be displayed on the monitor 201 are arbitrary. In addition, they may be variable. For example, a narrower region (for example, a region 412) than the captured image 401 may be enlarged and displayed as in FIG. 22B. With this setting, for example, an enlarged image of a lesion can be displayed.

Note that description regarding the light radiation regions (inside the circle 405) will be omitted below for the sake of convenience. In other words, light is assumed to be radiated to an entire captured image. In addition, since information of sensing is image information in this case, a portion of a captured image displayed on the monitor 201 will also be referred to as a display image and an image which is a sensing target (i.e., an image of an entire sensing region) will also be referred to as a monitoring target image.

<Example of a Main Configuration of the Monitoring Device, Etc.>

FIG. 23 is a block diagram showing still another example of the main configuration of the monitoring device 113 and the like of this case. In the example of FIG. 23, the monitoring sensor 125 of the example of FIG. 3 is omitted. In addition, the gyro sensor 172 of the endoscope 121 is also omitted. Furthermore, the monitoring device 113 has an image generation unit 421 instead of the visual field position estimation unit 191.

The image generation unit 421 acquires a captured image imaged and obtained by the imaging unit 171 of the endoscope 121 via the CCU 111. Using the captured image, the image generation unit 421 generates a display image to be displayed on the monitor 201 as an image of a region inside the visual field of the endoscope 121 and a monitoring target image to be used in detection of occurrence of an abnormality by the abnormality detection unit 192 as a result of sensing.

For example, the image generation unit 421 may extract a part of the captured image to set it to be a display image. In addition, the image generation unit 421 may set the entire captured image to be a monitoring target image.

The image generation unit 421 supplies the generated display image to the output control unit 194. Note that this display image may also be supplied to the notification information generation unit 193. The image generation unit 421 also supplies the generated monitoring target image to the abnormality detection unit 192.

The abnormality detection unit 192 analyzes the monitoring target image supplied from the image generation unit 421 and detects occurrence of an abnormality in the image. The abnormality detection unit 192 supplies information regarding the detected occurrence of the abnormality to the notification information generation unit 193. Note that the abnormality detection unit 192 may further supply the monitoring target image to the notification information generation unit 193.

The notification information generation unit 193 generates notification information for performing notification regarding the abnormality detected by the abnormality detection unit 192. Note that the notification information generation unit 193 may generate notification information further using the monitoring target image supplied from the abnormality detection unit 192 and the display image supplied from the image generation unit 421.

The notification information generation unit 193 supplies the generated notification information to the output control unit 194. Note that the notification information generation unit 193 may further supply the monitoring target information to the output control unit 194. Note that, since functional blocks of the notification information generation unit 193 are the same as those in the example of FIG. 5, description thereof will be omitted.

The output control unit 194, for example, supplies the display image supplied from the image generation unit 421 to the output device 114 to cause the image to be displayed on the monitor 201. In addition, the output control unit 194 supplies, for example, the notification information (an image, a sound, or the like) supplied from the notification information generation unit 193 to the output device 114 to cause the information to be output. Note that the output control unit 194 may further supply the monitoring target image supplied from the notification information generation unit 193 to the output device 114 to cause the image to be displayed on the monitor 201.

Through the operation described above, both generation of images of the region inside the visual field of the endoscope 121 and sensing of the inside and the periphery of the visual field of the endoscope 121 can be realized using the imaging unit 171 of the endoscope 121.

Note that the imaging unit 171 may be constituted by a plurality of image sensors. In other words, the endoscope 121 may have a plurality of imaging units. In addition, captured images supplied to the image generation unit 421 may be a plurality of captured image imaged and obtained by the plurality of imaging units of the endoscope 121.

<Abnormality Detection Unit>

FIG. 24 is a functional block diagram showing another example of the main function of the abnormality detection unit 192 of this case. In the example of FIG. 12, the abnormality detection unit 192 has the hemorrhage detection unit 211 and the contact detection unit 251.

The hemorrhage detection unit 211 of this case detects occurrence of a hemorrhage by analyzing the monitoring target image. In addition, the contact detection unit 251 also detects contact of a surgical instrument with an organ by analyzing the monitoring target image.

Of course, the functional blocks described above are examples. A function that the abnormality detection unit 192 can have is arbitrary, and is not limited to the examples. For example, the abnormality detection unit 192 may have a functional block other than the hemorrhage detection unit 211 and the contact detection unit 251 to realize a function other than the functions realized by the hemorrhage detection unit 211 and the contact detection unit 251. In addition, for example, any one or both of the hemorrhage detection unit 211 and the contact detection unit 251 may be omitted.

<Flow of an Endoscope Control Process>

An example of the flow of an endoscope control process executed in the endoscopic surgery support system 100 of this case will be described with reference to the flowchart of FIG. 25.

When the endoscope control process is started, the light source device 112 emits light to be radiated from the endoscope 121 (illumination light) to supply the light to the endoscope 121 in Step S401. Accordingly, light is radiated from the endoscope 121 toward the inside of an angle of view (subject) for imaging.

In Step S402, the imaging unit 171 of the endoscope 121 captures an imaging region including a region inside the visual field of the endoscope 121.

In Step S403, the image generation unit 421 extracts a part of the captured image obtained in Step S402 as a display image and sets the entire captured image to be a monitoring target image.

In Step S404, the output control unit 194 supplies the display image obtained from the process of Step S403 to the output device 114. The monitor 201 of the output device 114 displays the display image as an endoscope in-visual-field image (image of the region inside the visual field).

In Step S405, the monitoring device 113 monitors the monitoring target image obtained from the process of Step S403.

In Step S406, the monitoring device 113 determines whether or not the endoscope control process is to be ended. When the process is determined not to be ended, the process returns to Step S401 and execution of the step and the succeeding steps is repeated. When the endoscope control process is determined to be ended in Step S406, the endoscope control process ends.

<Flow of a Monitoring Process>

Next, an example of the flow of a monitoring process of this case executed in Step S405 of FIG. 25 will be described with reference to the flowchart of FIG. 26. When the monitoring process is started, the abnormality detection unit 192 uses the monitoring target image to detect occurrence of an abnormality in the image in Step S421.

In Step S422, the notification information generation unit 193 determines whether or not the abnormality has occurred based on the process result of Step S421. When it is determined that the occurrence of the abnormality has been detected (in other words, the abnormality has occurred), the process proceeds to Step S423.

In Step S423, the notification information generation unit 193 generates notification information for performing notification regarding the occurrence of the abnormality. In Step S424, the output control unit 194 supplies the notification information generated in Step S423 to the output device 114 to cause the information to be output. The output device 114 outputs the supplied notification information.

When the process of Step S424 ends, the process proceeds to Step S425. In addition, when it is determined that the occurrence of an abnormality has not been detected (i.e., no abnormality has occurred) in Step S422, the process proceeds to Step S425.

In Step S425, the monitoring device 113 determines whether or not monitoring is to be ended. When monitoring is determined not to be ended, the process returns to Step S421, and execution of the step and succeeding steps is repeated.

When monitoring is determined to be ended in Step S425, the monitoring process ends, and the process returns to the process of FIG. 25.

<Flow of an Abnormality Detection Process>

Next, an example of the flow of an abnormality detection process of this case executed in Step S421 of FIG. 26 will be described with reference to the flowchart of FIG. 27.

When the abnormality detection process is started, the hemorrhage detection unit 211 analyzes the monitoring target image thereby to detect occurrence of a hemorrhage in Step S441.

In Step S442, the contact detection unit 251 analyzes the monitoring target image to detect contact of a surgical instrument with an organ.

When detection of an abnormality based on each parameter of the monitoring target ends, the abnormality detection process ends, and the process returns to the process of FIG. 26.

<Flow of a Notification Information Generation Process>

Next, an example of the flow of a notification information generation process of this case executed in Step S423 of FIG. 26 will be described with reference to the flowchart of FIG. 28.

When the notification information generation process is started, the abnormality occurrence notification generation unit 221 of the notification information generation unit 193 generates an abnormality occurrence notification in Step S461.

In Step S462, the abnormality occurrence position specification unit 222 specifies a relative position of the abnormality occurrence location to a position in the display image in the captured image (i.e., a position in the region inside the visual field).

In Step S463, the abnormality occurrence position specification unit 222 determines whether or not the position of the abnormality occurrence location specified in Step S462 is within the display image (i.e., within the region inside the visual field). When the position of the abnormality occurrence location is determined to be within the display image, the process proceeds to Step S464.

In Step S464, the abnormality occurrence location notification generation unit 223 generates an abnormality occurrence location notification. After the abnormality occurrence location notification is generated, the notification information generation process ends, and the process returns to the process of FIG. 26.

In addition, when the position of the abnormality occurrence location is determined to be out of the display image in Step S463 of FIG. 28, the process proceeds to Step S465.

In Step S465, the abnormality occurrence direction notification generation unit 224 generates an abnormality occurrence direction notification. After the abnormality occurrence direction notification is generated, the notification information generation process ends, and the process returns to the process of FIG. 26.

By executing the processes as described above, the monitoring device 113 can realize both display of an image of the inside of the visual field of the endoscope 121 and sensing of the inside and the periphery of the visual field of the endoscope 121 using the captured image obtained by the imaging unit 171 of the endoscope 121. That is, the monitoring device 113 can cause an abnormality occurring in the inside and the periphery of the visual field of the endoscope to be ascertained more easily.

5. Fifth Embodiment

<Display of an Enlarged Image and an Overhead-View Image>

Note that, although the case in which the partial region 412 of the captured image 401 is enlarged and displayed has been described in FIG. 22B, when such an enlarged image is displayed, an image of a region of a wider range than the region 412 of the enlarged image of the captured image 401 may be displayed as an overhead-view image, along with the enlarged image.

When an enlarged image and an overhead-view image are displayed as above, for example, the overhead-view image may be displayed in the form of picture-in-picture of the enlarged image.

FIG. 29 shows an example of a display image of this case. In the example of FIG. 29, an enlarged image 502 obtained by cutting out and enlarging a part of a captured image is displayed in an entire display image 501. An overhead-view image 503 is displayed in a picture-in-picture form in a lower right region of the display image 501.

When a lesion 512 is enlarged and displayed as in the example of FIG. 29, for example, the enlarged image 502 only displays a narrower range such as a part of an organ 511 or the like. By also displaying the overhead-view image 503 within the display image 501 as in the example of FIG. 29, an operator or the like can ascertain the position of the enlarged part and the position of a an abnormality occurrence location more accurately.

Note that a part of the overhead-view image 503 which corresponds to the enlarged image may be expressed using, for example, a dotted-line frame or highlight display. Due to such expression, an operator or the like can ascertain the position, size, and the like of an enlarged region more easily.

In addition, in the case of the display image 501, various notifications such as an abnormality occurrence notification, an abnormality occurrence location notification, and an abnormality occurrence direction notification may be displayed on the enlarged image 502 or the overhead-view image 503.

Note that the enlarged image 502 and the overhead-view image 503 may be displayed in different regions. For example, the enlarged image 502 and the overhead-view image 503 may be displayed on different monitors.

It is better for the overhead-view image 503 to be an image of a region of a wider range than the region of the enlarged image of the captured image. Thus, the image of the part cut out from the captured image may be set as the overhead-view image 503 or the entire captured image may be set as the overhead-view image 503. In addition, for example, an image of a maximum displayable range (non-enlarged image) of the captured image may be set as the overhead-view image. In a case such as the example of FIG. 21B, for example, the entire region 402 may be set as the overhead-view image 503.

For example, the range of the overhead-view image 503 may be set to be variable. The range of the overhead-view image 503 may be decided according to, for example, a position of a predetermined surgical instrument. The range of the overhead-view image 503 may be decided such that, for example, distal ends of forceps are included therein.

In the examples of FIGS. 30A to 30C, for example, image frames 531 to 533 of the overhead-view image 503 are set according to positions of forceps 521 and 522 such that distal ends of the forceps are included therein. When the overhead-view image 503 is displayed in the picture-in-picture form in the display image 501 as in the example of FIG. 29, the display region of the overhead-view image 503 is not wide, and thus if the range of the overhead-view image 503 is set to be excessively wide, an image reduction ratio becomes excessively high (an image becomes very small), and there is concern of the image being difficult for an operator to view or the like. Therefore, by allowing the operator to arbitrarily set the overhead-view image 503 with ease as in the examples of FIG. 30, the range of the overhead-view image 503 (image reduction ratio) in the display image 501 can be set more appropriately, and thereby the overhead-view image 503 can be more easily visible.

Note that, when the image frame 531 (range) of the overhead-view image 503 is set to be variable as described above, an aspect ratio thereof may be fixed as in the examples of FIGS. 30A and 30B. In addition, the aspect ratio thereof may be set to be variable as in the example of FIG. 30C.

<Example of a Main Configuration of a Monitoring Device, Etc.>

A configuration of a monitoring device and the like of this case is the same as the example of FIG. 23. For example, the monitoring device 113 has the image generation unit 421, and it is better for the image generation unit 421 to extract a part of a captured image and set the part as a display image of an enlarged image, to set a wider range than the display image of the enlarged image of the captured image as a display image of an overhead-view image, and to set the entire captured image as a monitoring target image. With these settings, not only the enlarged image 502 but also the overhead-view image 503 can be displayed.

For example, the image generation unit 421 may cause the region of the display image of the enlarged image 502 to be included in the captured image, set a region of a wider range than the region of the display image of the enlarged image 502 therein, and extract the set region as a display image of the overhead-view image 503. With this setting, the range of the overhead-view image 503 can be variable.

In addition, for example, the image generation unit 421 may set a region to be extracted as a display image of the overhead-view image 503 according to a position of a predetermined surgical instrument. For example, the image generation unit 421 may set the region to be extracted as a display image of the overhead-view image 503 such that distal ends of forceps are included therein. In addition, for example, the image generation unit 421 may set the region to be extracted as a display image of the overhead-view image 503 with an aspect ratio thereof fixed.

With the settings, the operator can set the range of the overhead-view image 503 more easily.

In addition, the output control unit 194 may cause the display image of the overhead-view image to be displayed over a part of the display image of the enlarged image (in a picture-in-picture form) as in the example of FIG. 29.

Note that, because the flow of each process of this case is the same as that described in the fourth embodiment except that, in the endoscope control process, the display image of the enlarged image and the display image of the overhead-view image are extracted from the captured image in Step S403 and the display image of the overhead-view image is combined with the display image of the enlarged image in the picture-in-picture form in Step S404, description thereof will be omitted.

In addition, the range of the overhead-view image 503 may be controlled by fixing the range of the overhead-view image 503 in the captured image and controlling the range of the captured image, i.e., the angle of view of imaging by the imaging unit 171. For example, the range of the display image of the overhead-view image 503 generated by the image generation unit 421 may be controlled as the CCU 111 controls the angle of view of imaging by the imaging unit 171.

In this case, the CCU 111 may control the angle of view of imaging by the imaging unit 171, for example, according to a position of a predetermined surgical instrument. In addition, the CCU 111 may control the angle of view of imaging by the imaging unit 171 such that, for example, distal ends of forceps are included in the overhead-view image 503. Furthermore, the CCU 111 may control the angle of view of imaging by the imaging unit 171 such that, for example, an aspect ratio of the range of the overhead-view image 503 is fixed.

<Example of a Main Configuration of a Monitoring Device, Etc.>

A configuration of a monitoring device and the like is the same as in the example of FIG. 23 even when the angle of view of imaging is controlled as described above.

<Flow of an Endoscope Control Process>

An example of the flow of an endoscope control process when the angle of view of imaging is controlled as described above will be described with reference to the flowchart of FIG. 31. For the sake of convenience in description, however, the range of an overhead-view image will be described on the assumption that the range is an entire captured image.

When the endoscope control process is started, the light source device 112 emits light to be radiated from the endoscope 121 (illumination light) to supply the light to the endoscope 121 in Step S501. Accordingly, light is radiated from the endoscope 121 toward the inside of an angle of view (subject) for imaging.

In Step S502, the CCU 111 controls the angle of view of the imaging unit 171 of the endoscope 121. In Step S503, the imaging unit 171 of the endoscope 121 images the inside of the visual field of the endoscope 121.

In Step S504, the image generation unit 421 extracts a part of the captured image obtained in Step S503 as the enlarged image 502, and further sets the entire captured image as the overhead-view image 503 and a monitoring target image.

In Step S505, the output control unit 194 generates a display image of the overhead-view image obtained from the process of Step S504 displayed in a picture-in-picture form in the enlarged image, and supplies the display image to the output device 114. The monitor 201 of the output device 114 displays this display image.

In Step S506, the monitoring device 113 monitors the monitoring target image obtained from the process of Step S504.

In Step S507, the monitoring device 113 determines whether or not the endoscope control process is to be ended. When the process is determined not to be ended, the process returns to Step S501 and execution of the step and the succeeding steps is repeated. When the endoscope control process is determined to be ended in Step S507, the endoscope control process ends.

Since other processes are the same as those described in the fourth embodiment, description thereof is omitted.

By executing the processes described above, the operator can set the range of the overhead-view image 503 more easily.

6. Sixth Embodiment

<Computer>

The above-described series of processes can be executed by hardware or software. When the series of processes are executed by software, a program constituting the software is installed in a computer. The computer referred to herein includes, for example, a computer incorporated with dedicated hardware or a general-purpose personal computer or the like which can execute various functions with various programs installed therein.

FIG. 32 is a block diagram showing a configuration example of hardware of a computer which executes the above-described series of processes in a program.

In the computer 900 shown in FIG. 32, a central processing unit (CPU) 901, a read only memory (ROM) 902, and a random access memory (RAM) 903 are connected to one another by a bus 904.

An input and output interface 910 is also connected with the bus 904. The input and output interface 910 is connected with an input unit 911, an output unit 912, a storage unit 913, a communication unit 914, and a drive 915.

The input unit 911 includes, for example, a keyboard, a mouse, a microphone, a touch panel, an input terminal, and the like. The output unit 912 includes, for example, a display, a speaker, an output terminal, and the like. The storage unit 913 includes, for example, a hard disk, a RAM disk, a nonvolatile memory, and the like. The communication unit 914 includes, for example, a network interface. The drive 915 drives a removable medium 921 such as a magnetic disk, an optical disc, a magneto-optical disc, or a semiconductor memory.

In the computer configured as described above, the CPU 901 performs the above-described series of processes by, for example, loading a program stored in the storage unit 913 in the RAM 903 via the input and output interface 910 and the bus 904 and executing the program. The RAM 903 also appropriately stores data and the like necessary for the CPU 901 executing various processes.

A program executed by the computer (CPU 901) can be recorded in, for example, the removable medium 921 that is a package medium or the like for application. In such a case, the program can be installed in the storage unit 913 via the input and output interface 910 by loading the removable medium 921 in the drive 915.

In addition, this program can also be provided through a wired or wireless transmission medium such as a local area network, the Internet, or digital satellite broadcasting. In this case, the program can be received by the communication unit 914 and installed in the storage unit 913.

In addition, this program can also be installed in advance in the ROM 902 or the storage unit 913.

Note that a program executed by the computer may be a program in which a process is chronologically performed in the order described in the present specification or a program in which a process is performed in parallel or at a necessary timing such as a timing at which a call is performed.

In addition, steps for describing a program recorded in a recording medium of course include processes chronologically performed in the described order, but are not necessarily chronologically performed and include processes executed in parallel or independently.

In addition, the process of each step described above can be executed by the respective device described above or an arbitrary device other than the device described above. In this case, it is better for the device which executes the process to have a function described above (a functional block or the like) necessary for executing the process. In addition, it is better for information necessary for the process to be appropriately transmitted to the device.

In addition, a system means a set of a plurality of constituent elements (devices, modules (components), etc.) in the present specification, regardless of whether all constituent elements are in a same housing. Therefore, a plurality of devices each are accommodated in an individual housing and connected to each other via a network and one device formed by accommodating a plurality of modules in one housing are both systems.

In addition, a configuration described as one device (or processing unit) in the above description may be divided to be configured as a plurality of devices (or processing units). Conversely, a configuration described as a plurality of devices (or processing units) above may be put together to configure them as one device (or processing unit). In addition, configurations other than those described above may of course be added to the configuration of each device (or each processing unit). Furthermore, a part of the configuration of a certain device (or processing unit) may be included in the configuration of another device (or another processing unit) as long as overall configurations and operations of a system are substantially the same.

Although exemplary embodiments of the present disclosure have been described so far in detail with reference to the accompanying drawings, the technical scope of the present disclosure is not limited thereto. It is obvious that a person who has general knowledge in the technical field of the present disclosure can attain various modified and altered examples within the scope of the technical gist described in the claims, and it is also understood that the examples of course come under the technical range of the present disclosure.

For example, the present technology can have a configuration of cloud computing in which one function is shared and processed by a plurality of devices through a network.

In addition, each step described in the above flowcharts can be executed by one device, and shared and executed by a plurality of devices.

Furthermore, when a plurality of processes are included in one step, the plurality of processes included in the one step can be executed in one device, or shared and executed by a plurality of devices.

In addition, the present technology is not limited to the above, and can be executed in any configuration adopted in such a device or devices which constitute a system, for example, a processor of system large scale integration (LSI) or the like, a module which uses a plurality of processors or the like, a unit which uses a plurality of modules or the like, a set obtained by further adding another function to the unit (i.e., a partial configuration of a device), or the like.

The present technology can be applied to, for example, an endoscope device, a surgery support device which is used along with an endoscope device, a computer which controls such devices, an information processing system which supports endoscopic surgeries, a software module thereof, and the like.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An information processing device including:
an abnormality detection unit configured to detect occurrence of an abnormality in a region outside a visual field of an endoscope based on a result of sensing of a sensing region which includes at least a part of the region outside the visual field; and
a notification information generation unit configured to generate notification information for performing notification regarding the abnormality detected by the abnormality detection unit.

(2) The information processing device according to (1) in which the notification information generation unit generates notification information for performing notification regarding an abnormality occurrence location detected by the abnormality detection unit.

(3) The information processing device according to (2),
in which the sensing region also includes at least a part of a region inside the visual field of the endoscope, and
in which the abnormality detection unit further detects occurrence of an abnormality in the region inside the visual field based on a result of sensing of the sensing region.

(4) The information processing device described in (3) in which the notification information generation unit generates notification information for performing notification regarding the abnormality occurrence location using a method according to the position of the abnormality occurrence location.

(5) The information processing device according to (4) in which the notification information generation unit generates the notification information for performing notification regarding the abnormality occurrence location using a method according to whether or not a position of the abnormality occurrence location is within the region inside the visual field.

(6) The information processing device described in (5) in which the notification information generation unit generates the notification information for performing notification regarding the abnormality occurrence location when the position of the abnormality occurrence location is within the region inside the visual field.

(7) The information processing device described in (6) in which the notification information generation unit generates an image which indicates the abnormality occurrence location on an image of the region inside the visual field as the notification information for performing notification regarding the abnormality occurrence location.

(8) The information processing device described in (6) in which the notification information generation unit generates a sound which indicates the abnormality occurrence location as the notification information for performing notification regarding the abnormality occurrence location.

(9) The information processing device described in (5) in which the notification information generation unit generates notification information for performing notification regarding a direction of the abnormality occurrence location when the position of the abnormality occurrence location is within the region outside the visual field.

(10) The information processing device described in (9) in which the notification information generation unit generates an image which indicates a direction of the abnormality occurrence location on an image of the region inside the visual field as the notification information for performing notification regarding the direction of the abnormality occurrence location.

(11) The information processing device described in (9) in which the notification information generation unit generates a sound which indicates the direction of the abnormality occurrence location as the notification information for performing notification regarding the direction of the abnormality occurrence location.

(12) The information processing device described in (4) in which the notification information generation unit specifies the position of the abnormality occurrence location, and generates the notification information for performing notification regarding the abnormality occurrence location using a method according to the specified position of the abnormality occurrence location.

(13) The information processing device described in (12) in which the notification information generation unit determines whether or not the specified position of the abnormality occurrence location is within the region inside the visual field, and generates the notification information for performing notification regarding the abnormality occurrence location using a method according to a result of the determination.

(14) The information processing device described in (12) in which the notification information generation unit specifies the position of the abnormality occurrence location as a relative position to a position in the region inside the visual field.

(15) The information processing device described in (1) in which the notification information generation unit generates notification information for performing notification regarding detection of an abnormality by the abnormality detection unit.

(16) The information processing device described in (15) in which the notification information generation unit generates notification information for giving a notification that the abnormality has been detected.

(17) The information processing device described in (16) in which the notification information generation unit generates an image for giving the notification that the abnormality has been detected as the notification information for giving the notification that the abnormality has been detected.

(18) The information processing device described in (16) in which the notification information generation unit generates a sound for giving the notification that the abnormality has been detected as the notification information for giving the notification that the abnormality has been detected.

(19) The information processing device described in (15) in which the notification information generation unit generates notification information for performing notification regarding content of the detected abnormality.

(20) The information processing device described in (19) in which the notification information generation unit generates an image for performing notification regarding the content of the abnormality as the notification information for performing notification regarding the content of the abnormality.

(21) The information processing device described in (19) in which the notification information generation unit generates a sound for performing notification regarding the content of the abnormality as the notification information for performing notification regarding the content of the abnormality.

(22) The information processing device described in (1) in which the abnormality detection unit detects occurrence of a hemorrhage as occurrence of the abnormality.

(23) The information processing device described in (22) in which the abnormality detection unit detects the occurrence of the hemorrhage based on temperature distribution of the sensing region obtained as a result of the sensing.

(24) The information processing device described in (1) in which the abnormality detection unit detects occurrence of a temperature abnormality of a surgical instrument as occurrence of the abnormality.

(25) The information processing device described in (24) in which the abnormality detection unit detects the occurrence of the temperature abnormality of the surgical instrument based on temperature distribution of the sensing region obtained as a result of the sensing.

(26) The information processing device described in (1) in which the abnormality detection unit detects occurrence of a temperature abnormality of an organ as occurrence of the abnormality.

(27) The information processing device described in (26) in which the abnormality detection unit detects the occurrence of the temperature abnormality of the organ based on temperature distribution of the sensing region obtained as a result of the sensing.

(28) The information processing device described in (1) which further includes a visual field position estimation unit configured to estimate a position of the region inside the visual field.

(29) The information processing device described in (28) in which the visual field position estimation unit estimates the position of the region inside the visual field based on a result of the sensing.

(30) The information processing device described in (29) in which the visual field position estimation unit estimates the position of the region inside the visual field based further on an attitude of the endoscope or an attitude of a sensor unit which performs the sensing.

(31) The information processing device described in (29) in which the visual field position estimation unit estimates the position of the region inside the visual field based further on an image of the region inside the visual field.

(32) The information processing device described in (28) in which the notification information generation unit specifies a position of an abnormality occurrence location as a relative position to a position in the region inside the visual field estimated by the visual field position estimation unit, and generates notification information for performing notification regarding the abnormality using a method according to the specified position of the abnormality occurrence location.

(33) The information processing device according to (1), further including: an output unit configured to output the notification information generated by the notification information generation unit.

(34) The information processing device described in (33) in which the output unit includes a display unit configured to display an image of the notification information.

(35) The information processing device described in (34) in which the display unit further displays an image of the region inside the visual field.

(36) The information processing device described in (34) in which the display unit further displays an image relating to a result of the sensing.

(37) The information processing device described in (33) in which the output unit includes a sound output unit configured to output a sound of the notification information.

(38) The information processing device described in (36) in which the sound output unit further outputs a sound relating to a result of the sensing.

(39) The information processing device described in (1) which further includes a sensor unit configured to perform the sensing on the sensing region, and in which the abnormality detection unit detects occurrence of the abnormality based on a result of the sensing by the sensor unit.

(40) The information processing device described in (39) in which the sensor unit senses at least one of an image, light, electricity, sound, vibration, acceleration, speed, angular velocity, attitude, force, temperature, humidity, flow rate, magnetism, a chemical substance, and odor.

(41) The information processing device described in (40) in which the sensor unit further senses an attitude of the sensor unit.

(42) The information processing device described in (1) which further includes the endoscope.

(43) The information processing device described in (1) in which the abnormality detection unit detects occurrence of contact of a surgical instrument with an organ as occurrence of the abnormality.

(44) The information processing device described in (43) in which the abnormality detection unit detects the occurrence of the contact based on temperature distribution of the sensing region obtained as a result of the sensing and a stereoscopic image of the sensing region.

(45) The information processing device according to (1) in which the notification information generation unit further generates supervisor-dedicated notification information for performing notification regarding an abnormality detected by the abnormality detection unit to a supervisor other than an operator who performs a task in a region inside the visual field.

(46) The information processing device described in (45) in which the supervisor-dedicated notification information is information for performing notification regarding the abnormality detected by the abnormality detection unit using an image or a sound or both different from the notification information.

(47) The information processing device described in (45) in which the notification information generation unit generates an image for giving the notification that the abnormality has been detected as the supervisor-dedicated notification information.

(48) The information processing device described in (45) in which the notification information generation unit generates a sound for giving the notification that the abnormality has been detected as the supervisor-dedicated notification information.

(49) The information processing device described in (45) in which the notification information generation unit generates an image for performing notification regarding the content of the abnormality as the supervisor-dedicated notification information.

(50) The information processing device described in (45) in which the notification information generation unit generates a sound for performing notification regarding the content of the abnormality as the supervisor-dedicated notification information.

(51) The information processing device according to (45) in which the notification information generation unit generates, as the supervisor-dedicated notification information, an image for performing notification regarding the abnormality occurrence location.

(52) The information processing device according to (45) in which the notification information generation unit generates, as the supervisor-dedicated notification information, a sound for performing notification regarding the abnormality occurrence location.

(53) The information processing device described in (45) which further includes a supervisor-dedicated output unit configured to output the supervisor-dedicated notification information generated by the notification information generation unit.

(54) The information processing device described in (53) in which the supervisor-dedicated output unit includes a display unit configured to display an image of the supervisor-dedicated notification information.

(55) The information processing device described in (54) in which the display unit further displays an image of the region inside the visual field and an image relating to a result of the sensing.

(56) The information processing device described in (53) in which the supervisor-dedicated output unit includes a sound output unit configured to output a sound of the supervisor-dedicated notification information.

(57) The information processing device described in (56) in which the sound output unit further outputs a sound relating to a result of the sensing.

(58) The information processing device described in (1) which further includes an image generation unit configured to generate a display image and a monitoring target image which is used in detecting occurrence of the abnormality by the abnormality detection unit as a result of the sensing using a captured image obtained through imaging by an imaging unit of the endoscope.

(59) The information processing device described in (58) in which the image generation unit extracts a part of the captured image and sets the image as the display image.

(60) The information processing device described in (58) in which the image generation unit sets the entire captured image as the monitoring target image.

(61) The information processing device described in (58) in which the captured image is constituted by a plurality of captured images imaged and obtained by a plurality of imaging units of the endoscope.

(62) The information processing device described in (58) in which the abnormality detection unit detects occurrence of a hemorrhage as occurrence of the abnormality by analyzing the monitoring target image generated by the image generation unit.

(63) The information processing device described in (58) in which the abnormality detection unit detects occurrence of contact of a surgical instrument with an organ as occurrence of the abnormality by analyzing the monitoring target image generated by the image generation unit.

(64) The information processing device described in (58) in which the image generation unit extracts a part of the captured image, sets the image as a display image of an enlarged image, sets a wider range than the display image of the enlarged image of the captured image as a display image of an overhead-view image, and sets the entire captured image as the monitoring target image.

(65) The information processing device described in (64) in which the image generation unit causes a region of the display image of the enlarged image to be included in the captured image, sets a region of a wider range than the region of the display image of the enlarged image in the captured image, and extracts the set region as a display image of the overhead-view image.

(66) The information processing device described in (65) in which the image generation unit sets the region according to a position of a predetermined surgical instrument.

(67) The information processing device described in (65) in which the image generation unit sets the region to include distal ends of a forceps.

(68) The information processing device described in (65) in which the image generation unit sets the region with an aspect ratio fixed.

(69) The information processing device described in (64) which further includes an output control unit configured to cause the display image of the overhead-view image to be superimposed on a part of the display image of the enlarged image and displayed.

(70) The information processing device according to (64), further including: an angle-of-view control unit configured to control an angle of view of the display image of the overhead-view image generated by the image generation unit by controlling an angle of view of imaging by the imaging unit.

(71) The information processing device described in (70) in which the angle-of-view control unit controls the angle of view of imaging by the imaging unit according to a position of a predetermined surgical instrument.

(72) The information processing device described in (70) in which the angle-of-view control unit controls the angle of view of imaging by the imaging unit such that distal ends of a forceps are imaged.

(73) The information processing device described in (70) in which the angle-of-view control unit controls the angle of view of imaging by the imaging unit with an aspect ratio fixed.

(74) An information processing method including:
detecting occurrence of an abnormality in a region outside a visual field of an endoscope based on a result of sensing of a sensing region which includes at least a part of the region outside the visual field; and
generating notification information for performing notification regarding the detected abnormality.

(75) A surgical system including:
a monitoring sensor configured to sense a characteristic of a surgical site within a body, in a sensing region of the surgical site which includes at least a part of a region outside a display field of an endoscope; and
circuitry configured to
detect an occurrence of a medical abnormality in the region outside the display field of the endoscope based on a result of the sensing by the monitoring sensor, and generate notification information regarding the detected medical abnormality.

(76) The surgical system described in (75), wherein the monitoring sensor is a device separated from the endoscope.

(77) The surgical system described in (75), wherein the monitoring sensor is incorporated into the endoscope.

(78) The surgical system described in (77), wherein the endoscope includes at least one imaging sensor, and
wherein the monitoring sensor includes the at least one imaging sensor.

(79) The surgical system described in (75), wherein the notification information further includes information regarding an occurrence location of the medical abnormality.

(80) The surgical system described in (79), wherein the sensing region of the surgical site also includes at least a part of a region inside the display field of the endoscope, and wherein the circuitry is further configured to detect an occurrence of a medical abnormality in the region inside the display field of the endoscope based on a result of the sensing by the monitoring sensor.

(81) The surgical system described in (80), wherein the circuitry is further configured to generate the notification information regarding the occurrence location of the medical abnormality based on whether or not the occurrence location of the medical abnormality is within the region inside the display field of the endoscope.

(82) The surgical system described in (81), wherein, when the occurrence location is within the region inside the display field of the endoscope, the circuitry is configured to generate, as the notification information, an image that indicates the occurrence location on an image of the region inside the display field of the endoscope and/or a sound that indicates the occurrence location.

(83) The surgical system described in (81), wherein, when the occurrence location is within the region outside the display field of the endoscope, the circuitry is further configured to generate, as the notification information, an image that indicates the direction of the occurrence location on an image of the region inside the display field of the endoscope and/or a sound that indicates the direction of the occurrence location.

(84) The surgical system described in (81), wherein the circuitry is further configured to specify the occurrence location as a relative position to a position in the region inside the display field of the endoscope, determine whether or not the specified position of the occurrence location is within the region inside the display field of the endoscope, and generate the notification information for performing notification regarding the occurrence location based on a result of the determination.

(85) The surgical system described in (84), wherein the circuitry is further configured to estimate a position of the region inside the display field of the endoscope, and specify the occurrence location as the relative position to the position in the region inside the display field of the endoscope.

(86) The surgical system described in (75), wherein the circuitry is further configured to generate, as the notification information, a first notification that the medical abnormality has been detected, a second notification regarding content of the detected medical abnormality, with or without an image or a sound corresponding to the notifications.

(87) The surgical system described in (75), wherein the occurrence of the medical abnormality is an occurrence of a hemorrhage, an occurrence of a temperature abnormality of a surgical instrument, an occurrence of a temperature abnormality of an organ, or an occurrence of contact of a surgical instrument with an organ.

(88) The surgical system described in (75), wherein the circuitry is further configured to generate supervisor-dedicated notification information used for performing a notification regarding the detected medical abnormality to a supervisor other than an operator who performs a task in a region inside the display field of the endoscope.

(89) The surgical system described in (75), wherein the circuitry is configured to extract a part of a captured image obtained by the endoscope, set the part of the captured image as a display image, and set an entire of the captured image as a monitoring target image to be used in detection of the occurrence of the medical abnormality.

(90) The surgical system described in (89), wherein the circuitry is further configured to set the part of the captured image as an enlarged image, set a wider range than the enlarged image of the captured image as an overhead-view image to be displayed by being superimposed on a part of the enlarged image, and set the entire of the captured image as the monitoring target image to be used in detection of the occurrence of the medical abnormality.

(91) The surgical system described in (90), wherein the circuitry is further configured to control an angle of view of the overhead-view image by controlling an angle of view of imaging according to a position of a predetermined surgical instrument.

(92) The surgical system described in (75), wherein the characteristic of a surgical site is at least one of an image, light, electricity, sound, vibration, acceleration, speed, angular velocity, attitude, force, temperature, humidity, flow rate, magnetism, a chemical substance, and odor.

(93) An information processing device, including: circuitry configured to detect an occurrence of a medical abnormality in a region outside a display field of an endoscope based on a result of sensing by a monitoring sensor configured to sense a characteristic of a surgical site within a body, in a sensing region of the surgical site which includes at least a part of the region outside the display field of the endoscope, and generate notification information regarding the detected medical abnormality.

(94) The information processing device described in (93), wherein the notification information further includes information regarding an occurrence location of the medical abnormality.

(95) The information processing device described in (94), wherein the sensing region of the surgical site also includes at least a part of a region inside the display field of the endoscope, and wherein the circuitry is further configured to detect an occurrence of a medical abnormality in the region inside the display field of the endoscope based on a result of the sensing by the monitoring sensor.

(96) The information processing described in (95), wherein the circuitry is further configured to generate the notification information regarding the occurrence location of the medical abnormality based on whether or not the occurrence location of the medical abnormality is within the region inside the display field of the endoscope.

(97) The information processing device described in (96), wherein, when the occurrence location is within the region inside the display field of the endoscope, the circuitry is configured to generate, as the notification information, an image that indicates the occurrence location on an image of the region inside the display field of the endoscope and/or a sound that indicates the occurrence location.

(98) The information processing device described in (96), wherein, when the occurrence location is within the region outside the display field of the endoscope, the circuitry is further configured to generate, as the notification information, an image that indicates the direction of the occurrence location on an image of the region inside the display field of the endoscope and/or a sound that indicates the direction of the occurrence location.

(99) The information processing device described in (96), wherein the circuitry is further configured to specify the occurrence location as a relative position to a position in the region inside the display field of the endoscope, determine whether or not the specified position of the occurrence location is within the region inside the display field of the endoscope, and generate the notification information for performing notification regarding the occurrence location based on a result of the determination.

(100) The information processing device described in (99), wherein the circuitry is further configured to estimate a position of the region inside the display field of the endoscope, and specify the occurrence location as the relative position to the position in the region inside the display field of the endoscope.

(101) The information processing device described in (93), wherein the circuitry is further configured to generate, as the notification information, a first notification that the medical abnormality has been detected, a second notification regarding content of the detected medical abnormality, with or without an image or a sound corresponding to the notifications.

(102) The information processing device described in (93), wherein the occurrence of the medical abnormality is an occurrence of a hemorrhage, an occurrence of a temperature abnormality of a surgical instrument, an occurrence of a temperature abnormality of an organ, or an occurrence of contact of a surgical instrument with an organ.

(103) The information processing device described in (93), wherein the circuitry is further configured to generate supervisor-dedicated notification information used for performing a notification regarding the detected medical abnormality to a supervisor other than an operator who performs a task in a region inside the display field of the endoscope.

(104) The information processing device described in (93), wherein the circuitry is configured to extract a part of a captured image obtained by the endoscope, set the part of the captured image as a display image, and set an entire of the captured image as a monitoring target image to be used in detection of the occurrence of the medical abnormality.

(105) The information processing device described in (104), wherein the circuitry is further configured to set the part of the captured image as an enlarged image, set a wider range than the enlarged image of the captured image as an overhead-view image to be displayed by being superimposed on a part of the enlarged image, and set the entire of the captured image as the monitoring target image to be used in detection of the occurrence of the medical abnormality.

(106) The information processing device described in (105), wherein the circuitry is further configured to control an angle of view of the overhead-view image by controlling an angle of view of imaging according to a position of a predetermined surgical instrument.

(107) The information processing device described in (93), wherein the characteristic of a surgical site is at least one of an image, light, electricity, sound, vibration, acceleration, speed, angular velocity, attitude, force, temperature, humidity, flow rate, magnetism, a chemical substance, and odor.

(108) An information processing method, including:

detecting an occurrence of a medical abnormality in a region outside a display field of an endoscope based on a result of sensing by a monitoring sensor configured to sense a characteristic of a surgical site within a body, in a sensing region of the surgical site which includes at least a part of the region outside the display field of the endoscope, and generating notification information regarding the detected medical abnormality.

REFERENCE SIGNS LIST 100 endoscopic surgery support system
111 CCU
112 light source device
113 monitoring device
114 output device
115 surgical instrument control device
116 pneumoperitoneum device
121 endoscope
122 energy device
123 forceps
124 pneumoperitoneum needle
125 monitoring sensor
131 trocar
141 patient bed
151 patient
161 lesion
162 region inside visual field
163 region outside visual field
171 imaging unit
172 gyro sensor
181 thermo sensor
182 gyro sensor
191 visual field position estimation unit
192 abnormality detection unit
193 notification information generation unit
194 output control unit
201 monitor
202 speaker
211 hemorrhage detection unit
212 surgical instrument temperature abnormality detection unit
213 organ temperature abnormality detection unit
221 abnormality occurrence notification generation unit
222 abnormality occurrence position specification unit
223 abnormality occurrence location notification generation unit
224 abnormality occurrence direction notification generation unit
230 endoscope in-visual-field image
231 lesion
232 accumulation of blood
233 abnormality occurrence notification image
234 abnormality occurrence location notification image
235 abnormality occurrence direction notification image
241 stereoscopic camera
251 contact detection unit
301 operator-dedicated output device
302 supervisor-dedicated output device
311 monitor
312 speaker
321 monitor
322 speaker
331 sensing result notification generation unit
341 lesion
342 region inside visual field
343 region outside visual field
361 abnormality occurrence notification image
362 abnormality occurrence location notification image
401 captured image
421 image generation unit 501 display image
502 enlarged image
503 overhead-view image
511 organ
512 lesion
521, 522 forceps
531 to 533 image frame
900 computer

The invention claimed is:

1. A surgical system comprising:
an endoscope having a single visual field at a time, wherein a first area of a surgical site occupies an entirety of the single visual field;
a monitor that displays the single visual field of the first area;
a monitoring sensor configured to sense a characteristic of the surgical site in a sensing region including a second area of the surgical site outside the first area of the surgical site imaged by the endoscope and displayed on the monitor; and
circuitry configured to
detect an occurrence of a medical abnormality in the second area based on a result of the sensing by the monitoring sensor, and
generate notification information regarding the detected result wherein,
the sensing region of the surgical site also includes at least a part of the first area imaged by the endoscope, and
the circuitry is further configured to
detect an occurrence of a medical abnormality in the region inside the first area imaged by the endoscope based on a result of the sensing by the monitoring sensor, and
generate the notification information based on whether or not an occurrence location of the medical abnormality is within the first area imaged by the endoscope.

2. The surgical system according to claim 1, wherein the monitoring sensor is a device separated from the endoscope.

3. The surgical system according to claim 1, wherein the monitoring sensor is incorporated into the endoscope.

4. The surgical system according to claim 3, wherein the endoscope includes at least one imaging sensor, and
wherein the monitoring sensor includes the at least one imaging sensor.

5. The surgical system according to claim 1, wherein, when the occurrence location is within the first area imaged by the endoscope, the circuitry is configured to generate, as the notification information, an image that indicates the occurrence location on an image of the region inside the first area of the endoscope and/or a sound that indicates the occurrence location.

6. The surgical system according to claim 1, wherein, when the occurrence location is within the second area, the circuitry is further configured to generate, as the notification information, an image that indicates the direction of the occurrence location of the medical abnormality and display the notification information in the first area on the monitor.

7. The surgical system according to claim 1, wherein the circuitry is further configured to
specify the occurrence location as a relative position to a position in the first area imaged by the endoscope,
determine whether or not the specified position of the occurrence location is within the first area imaged by the endoscope, and
generate the notification information for performing notification regarding the occurrence location based on a result of the determination.

8. The surgical system according to claim 7, wherein the circuitry is further configured to estimate a position of the first area imaged by the endoscope, and specify the occurrence location as the relative position to the position in the first area imaged by the endoscope.

9. The surgical system according to claim 1, wherein the circuitry is further configured to generate, as the notification information, a first notification that the medical abnormality has been detected, a second notification regarding content of the detected medical abnormality, with or without an image or a sound corresponding to the notifications.

10. The surgical system according to claim 1, wherein the occurrence of the medical abnormality is an occurrence of a hemorrhage, an occurrence of a temperature abnormality of a surgical instrument, an occurrence of a temperature abnormality of an organ, or an occurrence of contact of a surgical instrument with an organ.

11. The surgical system according to claim 1, wherein the circuitry is further configured to generate supervisor-dedicated notification information used for performing a notification regarding the detected medical abnormality to a supervisor other than an operator who performs the task in a first area imaged by the endoscope.

12. The surgical system according to claim 1, wherein the circuitry is configured to
extract a part of a captured image obtained by the endoscope, set the part of the captured image as a display image, and set an entire of the captured image as a monitoring target image to be used in detection of the occurrence of the medical abnormality.

13. The surgical system according to claim 12, wherein the circuitry is further configured to
set the part of the captured image as an enlarged image,
set a wider range than the enlarged image of the captured image as an overhead-view image to be displayed by being superimposed on a part of the enlarged image, and
set the entire of the captured image as the monitoring target image to be used in detection of the occurrence of the medical abnormality.

14. The surgical system according to claim 13, wherein the circuitry is further configured to control an angle of view of the overhead-view image by controlling an angle of view of imaging according to a position of a predetermined surgical instrument.

15. The surgical system according to claim 1, wherein the characteristic of a surgical site is at least one of an image, light, electricity, sound, vibration, acceleration, speed, angular velocity, attitude, force, temperature, humidity, flow rate, magnetism, a chemical substance, and odor.

16. An information processing device, comprising:
circuitry configured to
receive an image from an endoscope having a single visual field at a time, wherein a first area of a surgical site occupies an entirety of the single visual field;
display the single visual field of the first area on a monitor;
detect an occurrence of a medical abnormality in a sensing region including a second area of the surgical site outside the first area of the surgical site imaged by the endoscope and displayed on the monitor based on a result of sensing by a monitoring sensor configured to sense a characteristic of Flail the surgical site; and
generate notification information regarding the detected medical abnormality wherein,
the sensing region of the surgical site also includes at least a part of the first area imaged by the endoscope, and the circuitry is further configured to
detect an occurrence of a medical abnormality in the region inside the first area imaged by the endoscope based on a result of the sensing by the monitoring sensor, and
generate the notification information based on whether or not the occurrence location of the medical abnormality is within the first area imaged by the endoscope.

17. The information processing device according to claim 16, wherein, when the occurrence location is within the second area, the circuitry is configured to generate, as the notification information, an image that indicates the occurrence location of the medical abnormality and display the notification information in the first area on the monitor.

18. The information processing device according to claim 16, wherein, when the occurrence location is within the first area imaged by the endoscope, the circuitry is further configured to generate, as the notification information, an image that indicates the direction of the occurrence location on an image of the first area imaged by the endoscope and/or a sound that indicates the direction of the occurrence location.

19. The information processing device according to claim 16, wherein the circuitry is further configured to
specify the occurrence location as a relative position to a position in the first area imaged by the endoscope,
determine whether or not the specified position of the occurrence location is within the first area imaged by the endoscope, and
generate the notification information for performing notification regarding the occurrence location based on a result of the determination.

20. The information processing device according to claim 19, wherein the circuitry is further configured to
estimate a position of the first area imaged by the endoscope, and
specify the occurrence location as the relative position to the position in the first area imaged by the endoscope.

21. The information processing device according to claim 16, wherein the circuitry is further configured to generate, as the notification information, a first notification that the medical abnormality has been detected, a second notification regarding content of the detected medical abnormality, with or without an image or a sound corresponding to the notifications.

22. The information processing device according to claim 16, wherein the occurrence of the medical abnormality is an occurrence of a hemorrhage, an occurrence of a temperature abnormality of a surgical instrument, an occurrence of a temperature abnormality of an organ, or an occurrence of contact of a surgical instrument with an organ.

23. The information processing device according to claim 16, wherein the circuitry is further configured to generate supervisor-dedicated notification information used for performing a notification regarding the detected medical abnormality to a supervisor other than an operator who performs a task in the first area imaged by the endoscope.

24. The information processing device according to claim 16, wherein the circuitry is configured to
extract a part of a captured image obtained by the endoscope,
set the part of the captured image as a display image, and
set an entire of the captured image as a monitoring target image to be used in detection of the occurrence of the medical abnormality.

25. The information processing device according to claim 24, wherein the circuitry is further configured to
set the part of the captured image as an enlarged image,
set a wider range than the enlarged image of the captured image as an overhead-view image to be displayed by being superimposed on a part of the enlarged image, and
set the entire of the captured image as the monitoring target image to be used in detection of the occurrence of the medical abnormality.

26. The information processing device according to claim 25, wherein the circuitry is further configured to control an angle of view of the overhead-view image by controlling an angle of view of imaging according to a position of a predetermined surgical instrument.

27. The information processing device according to claim 16, wherein the characteristic of a surgical site is at least one of an image, light, electricity, sound, vibration, acceleration, speed, angular velocity, attitude, force, temperature, humidity, flow rate, magnetism, a chemical substance, and odor.

* * * * *